(12) United States Patent
Swayze et al.

(10) Patent No.: US 7,244,847 B2
(45) Date of Patent: Jul. 17, 2007

(54) BENZIMIDAZOLE COMPOUNDS

(75) Inventors: Eric E. Swayze, Carlsbad, CA (US); Yun He, Carlsbad, CA (US); Punit P. Seth, Carlsbad, CA (US); Elizabeth Anne Jefferson, La Jolla, CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 83 days.

(21) Appl. No.: 10/071,978

(22) Filed: Feb. 6, 2002

(65) Prior Publication Data

US 2003/0187258 A1 Oct. 2, 2003

(51) Int. Cl.
*C07D 401/04* (2006.01)
*C07D 401/14* (2006.01)
*C07D 403/06* (2006.01)
*A61K 31/454* (2006.01)
*A61P 31/04* (2006.01)

(52) U.S. Cl. .................. 546/187; 544/139; 544/333; 544/370; 544/264; 548/307.4; 548/309.7; 548/310.4; 548/306.1; 548/310.7; 548/305.4; 546/193

(58) Field of Classification Search ................ 546/194, 546/193, 187; 544/139, 333, 370, 264; 548/307.4, 548/309.7, 310.4, 306.1, 310.7, 305.4
See application file for complete search history.

(56) References Cited

U.S. PATENT DOCUMENTS 3,864,490 A 2/1975 Daum et al.

FOREIGN PATENT DOCUMENTS

| DE | 888032 | * | 8/1953 |
| DE | 19916460 A1 | * | 10/2000 |
| GB | 1354554 | * | 5/1974 |
| WO | WO00/56712 | | 9/2000 |
| WO | WO 01/00615 | * | 1/2001 |
| WO | WO 01/70705 | | 9/2001 |

OTHER PUBLICATIONS

Ogura et al. (Journal of Medicinal Chemistry, 1972, vol. 15, No. 9, pp. 923–926).*
Vlaovic et al. (Bioscience, Biotechnology, and Biochemistry, 1992, 56(2), 199–206).*
Chernova et al. {Khimiko–Farmasevticheski Zhurnai (1991), 25(1), pp. 50–52}.*
Hofstadler, S.A. et al., "Mass spectrometry as a drug discovery platform against RNA targets", *Curr. Opin. Drug iscovery Dev.*, 2000, 3, 423–431.
Hofstadler, S.A. et al., "Analysis of Noncovalent Complexes of DNA and RNA by Mass Spectrometry", *Chem. Rev. (Washington, D.C.)* 2001, 101, 377–390.

Griffey, R.H. et al., "Targeted Site–Specific Gas–Phase Cleavage of Oligoribonucleotides. Application in Mass Spectrometry–Based Identification of Ligand Binding Sites", *J. Am. Chem. Soc.*, 1999, 121, 474–475.
Sannes–Lowery, K.A. et al., "Measuring Dissociation Constants of RNA and Aminoglycoside Antibiotics by Electrospray Ionization Mass Spectrometry", *Analytical Biochemistry*, 2000, 280, 264–271.
Griffey, R.H. et al., "Characterization of Low–Affinity Complezes between RNA and Small Molecules Using Electrospray Ionization Mass Spectrometry", *J. Am. Chem. Soc.*, 2000, 122(41), 9933–9938.
Griffey, R.H. et al., "Determinants of aminoglycoside-binding specificity for rRNA by using mass spectrometry", *Proc. Natl. Acad. Sci. USA*, Aug. 1999, 96, 10129–10133.
International Search Report dated Dec. 1, 2004 for International Application No. PCT/US03/38417.
International Search Report dated Jul. 28, 2004 for International Application No. PCT/US03/38093.
Freter et al., Database Caplus on STN(Columbus, OH, USA), No. 98:160710, "Substituted n–(4–idolylpiperidinoalkyl) benzimidazolones and their use as pharmaceutical preparations," 1983, abstract, EP 58975, see RN 84461–75–6.
Fonquerna et al., Database Capluse on STN (Columbus, OH, USA), No. 136:369609, "Preparation of indolylpiperidines as antihistaminic and antiallergic agents," 2002, WO 2002–036589, see RN 423174–70–3 etc.
Edwards, Database Caplus on STN (Columbus, OH, USA), No. 79:18714, "Imidazole derivatives," 1973, abstract, DE 2259345, see RN 42032–10–0 and 42032–11–1.
Teuber et al., Database Caplus on STN (Columbus, OH, USA), No. 132:93320, "Preparation of aminobenzimidazoles and guanidines as novel potassium channel blocking agents," 2000, WO 2000–001676, see RN 83750–38–3 etc.
Agai et al., Database Caplus on STN (Columbus, OH, USA), No. 85:78096, "Condensed 1,3,5,–triazepines, III Derivatives of 4,5–dihydro–[1,3,5]triazepino1,2–a benzimidazole," *Tetrahedron* 1976, vol. 32, No. 7, pp. 839–842, abstract, see RN 60078–74–2 and 60078–75–3 etc.
Ogrua et al., Database Caplus on STN (Columbus, OH, USA), No. 77:160002, "Heterocyclic Compounds 10. Synthesis of some imidazo[1,2–a]benzimidazoles with potent analgetic activities," *Journal of Medicinal Chemistry*, 1972, vol. 15, No. 9, pp. 923–926, abstract, see RN 38652–78–7 etc.

(Continued)

*Primary Examiner*—Kahsay Habte
(74) *Attorney, Agent, or Firm*—Cozen O'Connor; Isis Pharmaceuticals Inc. Patent Department

(57) ABSTRACT

The present invention is directed to novel benzimidazoles according to representative structures I and II, and their derivatives that possess antibacterial activity. This invention is also directed to compositions including the benzimidazole derivatives, and methods for using the same.

29 Claims, 3 Drawing Sheets

OTHER PUBLICATIONS

Sarett et al., Database Caplus on STN (Columbus, OH, USA), No. 56:79451, "Benzimidazoles carrying thiazolyl, thiadiazolyl, and Isothiazolyl substituents in the 2-position," 1962, US 3017415, abstract, see RN 91843-61-7.

Merck & Co., Database Caplus on STN (Columbus, OH, USA), No. 62:15351, "Substituted Benzimidazoles," 1964, GB 866796, abstract, see RN 4048-07-1.

E.R. Squibb and Sons, Inc., Database Caplus on STN (Columbus, OH, USA), No. 82:156304, "Pridyl-1H-Benzimidazolc N-Oxide," 1975, abstract, US 3864350, see RN 55396-67-3.

Warner Lambert Co., Database Caplus on STN (Columbus, OH, USA), No. 108:131822, "Preparation and testing of antiarteriosclerotic substituted benzimidazol-2-yl-and 3H-imidazo[4,5-b]pyridine-2-ylphenoxyalkanoic acids and their salts and esters," 1988, US 4714762, abstract, see RN 113561-63-0.

Aventis Pharmaceuticals Products Inc., Database Caplus on STN (Columbus, OH, USA), No. 135:3443381, "Preparation of 1-aroyl-piperidinyl benzamidines as inhibitors of factor Xa or tryptase," 2001, WO 2001-081310, abstract, see RN 370864-68-9.

* cited by examiner

Figure 1

Minimal Inhibitory Concentrations (MIC, mM) of Benzimidazoles against Bacteria and Yeast

| Compound | Gram+ | | | | Gram- | | | | Yeast |
|---|---|---|---|---|---|---|---|---|---|
| | SA1 | EH2 | SP4 | SP6 | EC2 | VP8 | KP1 | PA2 | CA1 |
| 7a | 6-12 | 1-3 | 3-6 | 12-25 | 12-26 | 25-50 | 6-12 | 25-50 | 50-100 |
| 7b | 3-6 | 1-3 | 3-6 | 6-12 | 6-12 | 12-25 | 6-12 | 25-50 | 25-50 |
| 7c | 6-12 | 3-6 | 6-12 | 12-25 | 12-25 | 25-50 | 12-25 | 12-25 | >100 |
| 7d | 12-25 | 6-12 | 6-12 | 25-50 | 50-100 | NT | 25-50 | 25-50 | >100 |
| 7e | 6-12 | 3-6 | 6-12 | 25-50 | 25-50 | NT | 25-50 | 25-50 | >100 |
| 7g | 6-12 | 1-3 | 3-6 | 12-25 | 12-25 | 25-50 | 12-25 | 25-50 | >100 |
| 7i | 6-12 | 1-3 | 3-6 | 6-12 | 6-12 | 12-25 | 6-12 | 25-50 | >100 |
| 7j | 6-12 | 1-3 | 6-12 | 12-35 | 50-100 | 50-100 | 12-25 | 12-25 | 50-100 |
| 7k | 3-6 | 1-3 | 6-12 | 6-12 | 25-50 | >100 | 12-25 | 25-50 | 25-50 |
| 7l | 3-6 | 3-6 | 3-6 | 6-12 | 12-25 | 25-50 | 12-25 | 12-25 | >100 |
| 7m | 6-12 | 3-6 | 6-12 | 12-25 | 12-25 | 25-50 | 12-25 | 12-25 | 50-100 |
| 7o | 6-12 | 3-6 | 6-12 | 12-25 | 12-25 | 25-50 | 12-25 | 12-25 | >100 |
| 7r | 6-12 | 3-6 | 6-12 | 12-25 | 12-25 | 12-25 | 6-12 | 12-25 | 50-100 |
| 7s | 6-12 | 3-6 | 6-12 | 12-25 | 12-25 | 25-50 | 12-25 | 25-50 | >100 |
| 7t | 6-12 | 3-6 | 6-12 | 25-50 | 50-100 | 25-50 | 25-50 | 12-25 | 50-100 |
| 7u | 6-12 | 3-6 | 6-12 | 12-25 | 25-50 | 25-50 | 12-25 | 25-50 | >100 |
| 7x | 6-12 | 3-6 | 12-25 | 6-12 | 6-12 | 25-50 | 25-50 | 12-25 | 50-100 |
| 10b | 3-7 | 0.75-1.5 | 25-50 | 6-12 | 12-26 | 25-50 | 25-50 | 6-12 | 6-12 |
| 10c | 6-12 | 1-3 | 3-6 | 6-12 | 12-25 | NT | 6-12 | 12-25 | 12-25 |
| 12 | 3-6 | 1-3 | 3-6 | 6-12 | 6-12 | NT | 6-12 | 12-25 | 50-100 |

<sup>a</sup>SA1: S. aureus 13709; EH2: E. hirae 29212; SP4: S. pyogenes 49399; SP6: S. pneumoniae 6303; EC2: E. coli 25922; PV8: P. vulgaris 8427; KP1: K. pneumoniae 13383; PA2: P. aeruginosa 25416; CA1: C. albicans 10231, NT: Not tested.

Figure 2

Minimal Inhibitory Concentrations (MIC, mM) of Benzimidazoles against *Enterococcus*

| Compound | E.FAECALIS ATCC_11823 | E.FAECALIS ATCC_232 41 | E.FAECALI ATCC_420 0 | E.FAECALI ATCC_49757 | E.FAECALI ATCC_828 | E.FAECALIS ATCC_656 9 | E.FAECIUM ATCC_882 | E.HIRAE ATCC_292 12 |
|---|---|---|---|---|---|---|---|---|
| 7a | 3-6 | 6-12 | 6-12 | 6-12 | 6-12 | 3-6 | 6-12 | 1-3 |
| 7b | 3-6 | 3-6 | 3-6 | 3-6 | 3-6 | 3-6 | 3-6 | 1-3 |
| 7c | 6-12 | 12-25 | 12-25 | 12-25 | 12-25 | 6-12 | 12-25 | 3-6 |
| 7d | 12-25 | 25-50 | 25-50 | 12-25 | 12-25 | 12-25 | 25-50 | 6-12 |
| 7e | 12-25 | 12-25 | 12-25 | 12-25 | 12-25 | 12-25 | 12-25 | 3-6 |
| 7i | 6-12 | NT | NT | 50-100 | 50-100 | 50-100 | NT | 1-3 |
| 7k | NT | NT | NT | 25-50 | NT | 12-25 | NT | 1-3 |
| 7m | 12-25 | 12-25 | 12-25 | 12-25 | 12-25 | 6-12 | 12-25 | 3-6 |
| 7p | 6-12 | 12-25 | 12-25 | 12-25 | 6-12 | 6-12 | 6-12 | 3-6 |
| 7r | 12-25 | 6-12 | 12-25 | 6-12 | 6-12 | 6-12 | 12-25 | 3-6 |
| 7s | 12-25 | 12-25 | 12-25 | 12-25 | 12-25 | 6-12 | 12-25 | 3-6 |
| 7t | 12-25 | 12-25 | 12-25 | 12-25 | 12-25 | 6-12 | 12-25 | 3-6 |
| 7u | 12-25 | 12-26 | 12-25 | 12-26 | 12-26 | 6-12 | 12-25 | 3-6 |
| 7x | 3-6 | 6-12 | 6-12 | 6-12 | 6-12 | 3-6 | 6-12 | 3-6 |
| 10b | 3-6 | 6-12 | 6-12 | 6-12 | 6-12 | 3-6 | 6-12 | 0.7-1.5 |
| 10c | 3-6 | 3-6 | 6-12 | 3-6 | 6-12 | 3-6 | 3-6 | 1-3 |
| 12 | 6-12 | 6-12 | 6-12 | 6-12 | 3-6 | 3-6 | 6-12 | 1-3 |

NT: Not tested.

Figure 3

Minimal Inhibitory Concentrations (MIC) of Selected Benzimidazoles against Bacteria and Yeast[a]

| Compound | Gram + | | | | Gram - | | | | Yeast |
|---|---|---|---|---|---|---|---|---|---|
| | SA1 | EH2 | SP4 | SP6 | EC2 | PV8 | KP1 | PA2 | CA1 |
| 14a | 6-12 | 25-50 | 25-50 | 12-25 | 25-50 | 25-50 | 25-50 | 50-100 | 12-25 |
| 14b | 6-12 | 25-50 | 25-50 | 6-12 | >100 | >100 | 50-100 | >100 | >100 |
| 19f | 6-12 | 3-6 | 6-12 | 12-25 | 12-25 | 12-25 | 12-25 | 25-50 | 25-50 |
| 17g | 6-12 | 3-6 | 6-12 | 12-25 | 12-25 | 25-50 | 6-12 | 25-50 | 12-25 |
| 17h | 6-12 | 1-3 | 6-12 | 12-25 | 25-50 | >100 | 12-25 | >100 | >100 |
| 18j | 3-6 | 3-6 | 6-12 | 12-25 | >100 | 50-100 | 6-12 | 50-100 | >100 |
| 18m | 6-12 | 1-3 | 6-12 | 12-25 | >100 | 25-50 | 25-50 | 50-100 | 25-50 |

[a] SA1: S. aureus 13709; EH2: E. hirae 29212; SP4: S. pyogenes 49399; SP6: S. pneumoniae 6303; EC2: E. coli 25922; PV8: P. vulgaris 8427; KP1: K. pneumoniae 13383; PA2: P. aeruginosa 25416; CA1: C. albicans 10231.

BENZIMIDAZOLE COMPOUNDS

FIELD OF INVENTION

The present invention is directed to novel benzimidazole derivatives that possess antibacterial activity. The invention also is directed to compositions including the benzimidazole derivatives, and methods for using the same.

BACKGROUND OF THE INVENTION

Almost all the major classes of antibiotics have encountered resistances in clinical applications. The emergence of bacterial resistance to β-lactam antibiotics, macrolides, quinolones, and vancomycin is becoming a major worldwide health problem. The spread of antibiotic resistance among pathogenic bacteria imposes another serious problem for the clinical management of infectious diseases. Particularly, antibiotic resistance among Gram-positive bacteria (staphylococci, enterococci, and streptococci) is becoming increasingly serious. Entercococci, which are generally resistant to most antibiotics including penicillin, cephalosporin and aminoglycosides, used to be treated with either a combination of two antibiotics or vancomycin. However, with the recent increased use of vancomycin in methicillin-resistance *Staphylococcus aureus* (MRSA) infections and colitis due to colstridium fifficile, multiple resistant entercocccus faecium has been spreading. As such, the last resort for anti-infective diseases, the Vancomycin family of antibiotics, has now been gravely challenged in recent years due to the emergence of MRSA strains in clinical practice. There is an urgent need to discover novel antibacterial agents other than analogues of existing antibiotics.

A considerable amount of attention has focused recently on new RNA-binding molecules for drug discovery. The interactions between RNA and biological macromolecules are clearly essential fore many vital processes in molecular biology. In addition, the excitement over RNA-based viruses has fueled an interest in the development of potential RNA inhibitors. RNA offers several selective advantages over DNA as a therapeutic agent. First, chromosomal DNA is packaged extensively, significantly limiting its accessibility to small molecule regents. Second, DNA repair systems are available in the cell, whereas analogous enzymes for RNA repair are virtually unknown. Finally, RNA exhibits a high level of diversity in terms of tertiary folding, and therefore will likely have a greater potential for selective targeting based on structure rather than sequence.

Historically, however, RNA-based drug discovery has proved to be extremely difficult, and only a few classes of compounds are known to bind RNA with SAR information, for example aminoglycosides and cationic peptides. Discovery of RNA binders using traditional high throughput assays such as fluorescence, filter binding, SPA, SPR, etc. has proved to be equally unsuccessful.

Recently, a MS-based high throughput-screening assay has been developed. See, Hofstadler, S. A.; Griffey, R. H. *Curr. Opin. Drug Discovery Dev.* 2000, 3, 423–431; Hofstadler, S. A.; Griffey, R. H. *Chem. Rev.* (Washington, D.C.) 2001, 101, 377–390; Griffey, R. H.; Greig, M. J.; An, H.; Sasmor, H.; Manalili, S. *J. Am. Chem. Soc.* 1999, 121, 474–475; Sannes-Lowery, K. A.; Griffey, R. H.; Hofstadler, S. A. *Anal. Biochem.* 2000, 280, 264–271; Griffey, R. H.; Sannes-Lowery, K. A.; Drader, J. J.; Mohan, V.; Swayze, E. E.; Hofstadler, S. A. *J. Am. Chem. Soc.* 2000, 122, 9933–9938, and Griffey, R. H.; Hofstadler, S. A.; Sannes-Lowery, K. A.; Ecker, D. J.; Crooke, S. T. *Proc. Natl. Acad. Sci. U.S.A.* 1999, 96, 10129–10133, each of which is incorporated herein by reference in its entirety.

This assay is extremely sensitive and could detect RNA binders with Kd values ranging from nanomolar to minimolar. Coupled with mass assays to carry out competition experiments and determine the binding locations, such assays can be used to discover of novel compounds that bind to bacterial ribosomal RNA.

In view of the great importance of antibacterial compounds in animal, and particularly human health, it can be seen that there is a need for novel antibacterial agents. The present invention is therefore directed to, inter alia, such compounds and their uses, as well as other important ends.

SUMMARY OF THE INVENTION

The present invention also provides compositions containing the subject compounds, and methods for using the subject compounds. Methodologies for making the compounds of the invention are also disclosed. Other useful methodologies will be apparent to those skilled in the art, once armed with the present disclosure. These and other features of the compounds of the subject invention are set forth in more detail below.

In some embodiments, compounds are provided having the formula:

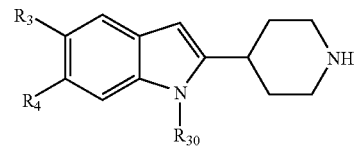

wherein:

$R_3$ and $R_4$ are independently each H, halogen, $C_1$–$C_6$ alkyl, $C_1$–$C_6$ alkoxy, trihaloalkyl, alkoxycarbonyl, alkoxy, $NR_{15}R_{16}$, or $NO_2$;

$R_{30}$ is $C_{1-6}$ alkyl, heteroarylalkyl, arylalkyl, or heteroaryl, wherein each of said heteroarylalkyl, arylalkyl, or heteroaryl groups each can be optionally substituted with up to three substitutents selected from haloegn, $NO_2$, and mono-, di-, or trihaloalkyl;

or $R_{30}$ has the structure XX:

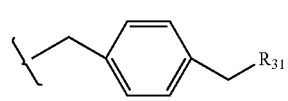

wherein $R_{31}$ is alkylamino, aminoalkylamino, poly(alkylamino)amino, heterocycloalkylamino, heterocycloalkyl, —NH—$(CHOH)_4$—$CH_2OH$, —NH—$(CH_2)_{1-12}$-heteroaryl or —NH—$(CH_2)_{1-12}$-heterocycloalkyl.

In a further aspect, the present invention provides dimeric benzimidazole compounds having the structure:

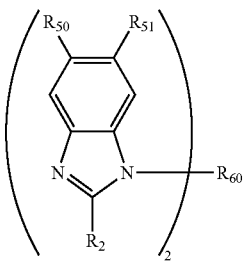

wherein:

$R_2$ is $NH_2$ or piperidin-4-yl;

$R_{50}$ and $R_{51}$ are each independently selected from H, halogen, $C_1$–$C_6$ alkyl, trihaloalkyl, alkoxycarbonyl, alkoxy, $NR_{15}R_{16}$, and $NO_2$, wherein said $C_1$–$C_6$ alkyl, alkoxycarbonyl, and alkoxy groups can each be optionally substituted with $NR_{15}R_{16}$;

$R_{15}$ is H, halogen, $C_{1-12}$ alkyl, methylcarbonyl, heterocycloalkyl, arylsulfonyl, heteroarylalkyl, aminoalkyl, arylcarbonyl, branched and straight chain polyaminoalkyl, or a group of formula $CH_2(CHOH)_4CH_2OH$, wherein said methylcarbonyl, heterocycloalkyl, arylsulfonyl, heteroarylalkyl, aminoalkyl, arylcarbonyl, and branched and straight chain polyaminoalkyl groups can be substituted by up to 3 OH groups;

$R_{16}$ is H, halogen, or $C_1$–$C_6$ alkyl;

or $R_{15}$ and $R_{16}$ together with the nitrogen atom to which they are attached can form a succinimido or phthalimido group or a fused ring derivative thereof, wherein said succinimido or phthalimido group or fused ring derivative thereof can be optionally substituted by up to three substituents independently selected from $NO_2$ and halogen;

$R_{60}$ is alkylene having from 1 to 18 carbons, or —$R_9$—X—$R_{10}$—)H;

$R_9$ and $R_{10}$ are each independently alkylene having from 1 to about 20 carbons;

X is —$N(R_{12})$—, —$C(R_{13})(R_{14})$— or O; and $R_{12}$, $R_{13}$ and $R_{14}$ are each independently H or $C_1$–$C_6$ alkyl.

In a further aspect, the present invention provides compounds of formula:

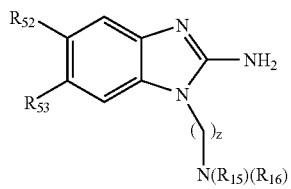

wherein:

$R_{52}$ and $R_{53}$ are each independently selected from H, halogen, $C_1$–$C_6$ alkyl, trihaloalkyl, alkoxycarbonyl, alkoxy, $NR_{15}R_{16}$, and $NO_2$, wherein said $C_1$–$C_6$ alkyl, alkoxycarbonyl, and alkoxy groups can each be optionally substituted with $NR_{15}R_{16}$; $R_{15}$ is H, halogen, $C_{1-12}$ alkyl, methylcarbonyl, heterocycloalkyl, arylsulfonyl, heteroarylalkyl, aminoalkyl, arylcarbonyl, branched and straight chain polyaminoalkyl, or a group of formula $CH_2(CHOH)_4CH_2OH$;

wherein said methylcarbonyl, heterocycloalkyl, arylsulfonyl, heteroarylalkyl, aminoalkyl, arylcarbonyl, and branched and straight chain polyaminoalkyl groups can be substituted by up to 3 OH groups;

$R_{16}$ is H, halogen, or $C_1$–$C_6$ alkyl;

or $R_{15}$ and $R_{16}$ together with the nitrogen atom to which they are attached can form a succinimido or phthalimido group or a fused ring derivative thereof, wherein said succinimido or phthalimido group or fused ring derivative thereof can be optionally substituted by up to three substituents independently selected from $NO_2$ and halogen; and z is 1 to 6.

Also provided by the present invention are compounds having the Formula:

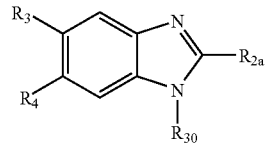

wherein:

$R_{2a}$ is amino, phenyl, mono- or bicyclic heterocycloalkyl having 1 or 2 ring nitrogen atoms, mono- or bicyclic heteroaryl having 1 or 2 ring nitrogen atoms, cycloalkyl; halogen, heterocycloalkylalkyl (i.e., alkyl sub w' heterocycloalkyl) having 1 or 2 ring nitrogen atoms, mono- or bicyclic heterocycloalkylamino having 1 or 2 ring nitrogen atoms or a group of formula —S-alkylene-$L_1$ where $L_1$ is mono- or bicyclic -heteroaryl having 1 or 2 ring nitrogen atoms;

wherein each of said amino, phenyl, heterocycloalkyl, heteroaryl, cycloalkyl, heterocycloalkylalkyl, or heterocycloalkylamino groups can be optionally substituted with a group selected from amino, OH, $C_1$–$C_{12}$ alkyl, a structure of formula —C(=O)CH($NH_2$)—$L_2$ where $L_2$ is the side chain of a naturally occurring alpha amino acid, —C($NH_2$)=NH, $C_1$–$C_{12}$ alkylcarbonyl, mono- or bicyclic heteroaryl having 1 or 2 ring nitrogen atoms, mono- or bicyclic heteroarylalkyl having 1 or 2 ring nitrogen atoms, or S-alkyl-heteroaryl where said heteroaryl is mono- or bicyclic having 1 or 2 ring nitrogen atoms; and $R_3$ and $R_4$ are each independently halogen, amino, $NO_2$, CN, $C_{1-6}$ alkoxy or $C_{1-6}$ alkyl optionally substituted with up to 3 halogen atoms; and $R_{30}$ is H, alkyl, aryl, arylalkyl, heteroaryl; heteroarylalkyl, heterocycloalkyl, arylsulfonyl, aryloxycarbonyl, alkoxyalkoxyalkyl, alkyl-S—$R_7$, alkyl-NH—C(=O)—$R_8$ or —$R_9$—X—$R_{10}$-$R_{11}$)H;

wherein each of the alkyl, aryl, arylalkyl heteroaryl, heteroarylalkyl, heterocycloalkyl, arylsulfonyl, aryloxycarbonyl and alkoxyalkoxyalkyl moieties in each of the foregoing $R_1$ groups can be optionally substituted with up to 3 groups independently selected from the group consisting of $C_1$–$C_6$ alkyl, OH, hydroxyalkyl, —C(=O)—$R_5$; CN, aryl, alkoxycarbonyl, alkylaryl, arylalkyl, heteroaryl, S-heteroaryl optionally substituted with halogen, heteroarylalkyl optionally substituted with halogen, heterocycloalkyl optionally substituted with amino, $NO_2$, halogen, monohaloalkyl, dihaloalkyl, trihaloalkyl, perhaloaryl, perhaloalkylaryl, alkyl-$NR_{15}R_{16}$ and $NR_{15}R_{16}$;

or one of said alkyl, aryl, arylalkyl heteroaryl, heteroarylalkyl, heterocycloalkyl, arylsulfonyl, aryloxycarbonyl or alkoxyalkoxyalkyl moieties of one of said $R_1$ groups can be attached to a structure of Formula I at position $R_1$ thereof;

$R_5$ is H, —$NHNHR_6$, —NH=CH—$R_6$, heteroaryl, heterocycloalkyl, wherein said hereteroaryl group can be optionally substituted with an aryl or heteroaryl group, $R_6$ is aryl, heteroaryl; arylsulfonyl, heteroarylsulfonyl, —C(=S)—NH—aryl, —C(=S)—NH-arylcarbonyl, —C(=S)—NH-heteroarylcarbonyl, —C(=S)—NH-alkylene-$R_{21}$, —C(=O)—NH-aryl, —C(=O)—NH-arylcarbonyl, —C(=O)—NH-heteroarylcarbonyl, or —C(=O)—NH-alkylene-$R_{21}$ where $R_{21}$ is carboxy, alkoxycarbonyl, aryl, heteroaryl, heterocycloalkyl, arylaminocarbonyl, cycloalkylaminocarbonyl, or a saturated hydrocarbon fused ring system optionally having an aryl ring fused thereto, said ring system being optionally substituted with up to three alkyl groups on the alkyl or aryl rings thereof;

wherein any of said $R_6$ groups can be optionally substituted with up to 3 groups selected from $NR_{15}R_{16}$, alkyl, hydroxy, halogen, aryl, alkoxy, trihaloalkoxy, arylalkyloxy, $NO_2$, —SH, —S-alkyl, heteroarylcarbonyl, heteroaryl, alkylheteroaryl, or a moiety of formula —$OC_2CH_2$—O— attached to adjacent atoms of said $R_6$ group;

$R_7$ is heteroaryl or heterocycloalkyl;

$R_8$ is aryl;

$R_9$ and $R_{10}$ are each independently alkylene having from 1 to about 20 carbons;

X is —N($R_{12}$)—, —C($R_{13}$)($R_{14}$)— or O;

$R_{11}$ is H, heterocycloaryl or alkoxy, wherein said heterocycloaryl or alkoxy group can be optionally substituted with up to four groups independently selected from halogen, amino, trihaloalkyl, alkoxycarbonyl, and CN;

$R_{12}$ is H or $C_1$–$C_6$ alkyl; and $R_{13}$ and $R_{14}$ are each independently H or $C_1$–$C_6$ alkyl;

$R_{15}$ is H, halogen, $C_{1-12}$ alkyl, methylcarbonyl, heterocycloalkyl, arylsulfonyl, heteroarylalkyl, aminoalkyl, arylcarbonyl, branched and straight chain polyaminoalkyl, or a group of formula $CH_2(CHOH)_4CH_2OH$, wherein said methylcarbonyl, heterocycloalkyl, arylsulfonyl, heteroarylalkyl, aminoalkyl, arylcarbonyl, and branched and straight chain polyaminoalkyl groups can be substituted by up to 3 OH groups;

$R_{16}$ is H, halogen, or $C_1$–$C_6$ alkyl;

or $R_{15}$ and $R_{16}$ together with the nitrogen atom to which they are attached can form a succinimido or phthalimido group or a fused ring derivative thereof, wherein said succinimido or phthalimido group or fused ring derivative thereof can be optionally substituted by up to three substituents independently selected from $NO_2$ and halogen, or a group of Formula I at position $R_1$ thereof;

or $R_{15}$ and $R_{16}$ together with the nitrogen atom to which they are attached can form a group of Formula I wherein said nitrogen atom is $Q_4$ thereof;

Also provided by the present invention are compounds of Formula:

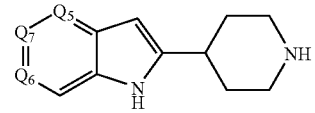

wherein:

$Q_5$ is CH or N;

$Q_6$ is C—$R_{61}$ or N;

$Q_7$ is C—$R_{60}$ or N;

$R_{60}$ and $R_{61}$ are each independently H, halogen, $C_{1-6}$ alkyl, trihaloalkyl, or $C_{1-6}$ alkoxy;

provided that when $Q_6$ is C—$R_{61}$, $Q_7$ is C—$R_{60}$ and $Q_5$ is CH, then $R_{60}$ and $R_{61}$ are not both H.

The present invention provides methods for treating a patient having a bacterial infection comprising administering to said patient a compound of the invention. Preferably, said patient is a human. Also provided are methods for inhibiting bacterial growth comprising contacting a bacterium with a compound of the invention. In some preferred embodiments, said bacterium a gram-positive bacteria, preferably from among staphylococci, enterococci, and streptococci. In some embodiments the bacterium is *S. aureus, E. hirae, S. pyogenes, S. pneumoniae, E. coli, P. vulgaris, K. pneumoniae, P. aeruginosa, C. albicans, E.faecalis, E.faecali,* or *E.faecium.*

The present invention also provides compositions that include at least one compound of the invention.

BRIEF DESCRIPTION OF THE DRAWINGS

FIG. 1 is a table showing activity of benzimidazoles of Examples 11 and 12 against four strains of Gram positive and four strains of gram negative bacteria.

FIG. 2 is a table showing activity of benzimidazoles of Examples 11 and 12 against seven clinically important strains of entercocccus.

FIG. 3 shows the in vitro inhibitorial activity of selected benzimidazoles of Example 16 against four Gram positive bacterial strains, four gram negative bacterial strains and one yeast strain.

DETAILED DESCRIPTION

The present invention also provides compositions containing the subject compounds, and methods for using the subject compounds. Methodologies for making the compounds of the invention are also disclosed. Other useful methodologies will be apparent to those skilled in the art, once armed with the present disclosure. These and other features of the compounds of the subject invention are set forth in more detail below.

In some embodiments, compounds are provided having the formula:

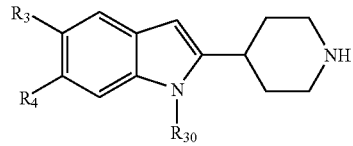

wherein:

$R_3$ and $R_4$ are independently each H, halogen, $C_1$–$C_6$ alkyl, $C_1$–$C_6$ alkoxy, trihaloalkyl, alkoxycarbonyl, alkoxy, $NR_{15}R_{16}$, or $NO_2$;

$R_{30}$ is $C_{1-6}$ alkyl, heteroarylalkyl, arylalkyl, or heteroaryl, wherein each of said heteroarylalkyl, arylalkyl, or heteroaryl groups each can be optionally substituted with up to three substituents selected from halogen, $NO_2$, and mono-, di-, or trihaloalkyl;

or $R_{30}$ has the structure XX:

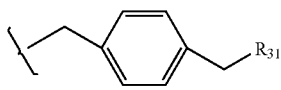

XX wherein $R_{31}$ is alkylamino, aminoalkylamino, poly(alkylamino)amino, heterocycloalkylamino, heterocycloalkyl, $-NH-(CHOH)_4-CH_2OH$, $-NH-(CH_2)_{1-12}$-heteroaryl or $-NH-(CH_2)_{1-12}$-heterocycloalkyl.

In some embodiments, $R_{30}$ has the structure XX. In some such embodiments, $R_{31}$ has the structure of any of the radicals shown in Example 11, infra, designated for compounds 7a–x.

In further embodiments, $R_1$ is pyridin-4-yl-methyl, pyridin-3yl-methyl, 4-fluorophen-1-yl-methyl, 4-nitrophen-1-yl-methyl, 4-(bromomethyl)phen-1-yl-methyl, pyrimidine-2-yl, or 2,4-dinitrophen-1-yl.

In a further aspect, the present invention provides dimeric benzimidazole compounds having the structure:

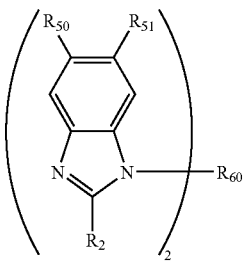

wherein:

$R_2$ is $NH_2$ or piperidin-4-yl;

$R_{50}$ and $R_{51}$ are each independently selected from H, halogen, $C_1-C_6$ alkyl, trihaloalkyl, alkoxycarbonyl, alkoxy, $NR_{15}R_{16}$, and $NO_2$ wherein said $C_1-C_6$ alkyl, alkoxycarbonyl, and alkoxy groups can each be optionally substituted with $NR_{15}R_{16}$; $R_{15}$ is H, halogen, $C_{1-12}$ alkyl, methylcarbonyl, heterocycloalkyl, arylsulfonyl, heteroarylalkyl, aminoalkyl, arylcarbonyl, branched and straight chain polyaminoalkyl, or a group of formula $CH_2(CHOH)_4CH_2OH$, wherein said methylcarbonyl, heterocycloalkyl, arylsulfonyl, heteroarylalkyl, aminoalkyl, arylcarbonyl, and branched and straight chain polyaminoalkyl groups can be substituted by up to 3 OH groups;

$R_{16}$ is H, halogen, or $C_1-C_6$ alkyl;

or $R_{15}$ and $R_{16}$ together with the nitrogen atom to which they are attached can form a succinimido or phthalimido group or a fused ring derivative thereof, wherein said succinimido or phthalimido group or fused ring derivative thereof can be optionally substituted by up to three substituents independently selected from $NO_2$ and halogen;

$R_{60}$ is alkylene having from 1 to 18 carbons, or $-R_9-X-R_{10}-)H$;

$R_9$ and $R_{10}$ are each independently alkylene having from 1 to about 20 carbons;

X is $-N(R_{12})-$, $-C(R_{13})(R_{14})-$ or O; and $R_{12}$, $R_{13}$ and $R_{14}$ are each independently H or $C_1-C_6$ alkyl.

In some embodiments if the dimeric compounds, $R_2$ is piperidin-4-yl. In further embodiments, $R_{50}$ and $R_{51}$ are each halogen, preferably chlorine.

In some embodiments, $R_{60}$ is alkylene having from 1 to 6 carbons or from 1 to 4 carbons. In some embodiments, $R_{60}$ is $-CH_2-C_6H_4-CH_2-$, preferably where $-CH_2-C_6H_4-CH_2-$ is a para-α,α-xylene radical.

In some of the foregoing embodiments, $R_2$ is $NH_2$. I further embodiments, $R_{50}$ and $R_{51}$ are each independently selected from H, halogen, methyl, $COOCH_3$, CN and $CF_3$.

In some embodiments, $R_{60}$ is $-R_9-X-R_{10}-$. In further embodiments, X is $-N(R_{12})-$. In some embodiments, $R_{12}$ is methyl and $R_9$ and $R_{10}$ are each $(CH_2)_2$ or $(CH_2)_3$, preferably wherein $R_{50}$ and $R_{51}$ are each halogen, or where $R_{50}$ and $R_{51}$ are each H, or where $R_{50}$ is Br and $R_{51}$ is H, or where $R_{50}$ is $CH_3$ and $R_{51}$ is H, or where $COOCH_3$ and $R_{51}$ is H, or where $CF_3$ and $R_{51}$ is H, or where $R_{50}$ is CN and $R_{51}$ is H.

In some embodiments, X is O. In some such embodiments, $R_9$ and $R_{10}$ are each $(CH_2)_2$ or $(CH_2)_3$, preferably where $R_{50}$ and $R_{51}$ are each halogen, or where $R_{50}$ and $R_{51}$ are each H, or where Br and $R_{51}$ is H, or where $R_{50}$ is $CH_3$ and $R_{51}$ is H, or where $R_{50}$ is $COOCH_3$ and $R_{51}$ is H, or where $R_{50}$ is $CF_3$ and $R_{51}$ is H, or where $R_{50}$ is CN and $R_{51}$ is H.

In a further aspect, the present invention provides compounds of formula:

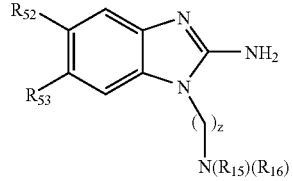

wherein:

$R_{52}$ and $R_{53}$ are each independently selected from H, halogen, $C_1-C_6$ alkyl, trihaloalkyl, alkoxycarbonyl, alkoxy, $NR_{15}R_{16}$, and $NO_2$, wherein said $C_1-C_6$ alkyl, alkoxycarbonyl, and alkoxy groups can each be optionally substituted with $NR_{15}R_{16}$;

$R_{15}$ is H, halogen, $C_{1-12}$ alkyl, methylcarbonyl, heterocycloalkyl, arylsulfonyl, heteroarylalkyl, aminoalkyl, arylcarbonyl, branched and straight chain polyaminoalkyl, or a group of formula $CH_2(CHOH)_4CH_2OH$;

wherein said methylcarbonyl, heterocycloalkyl, arylsulfonyl, heteroarylalkyl, aminoalkyl, arylcarbonyl, and branched and straight chain polyaminoalkyl groups can be substituted by up to 3 OH groups;

$R_{16}$ is H, halogen, or $C_1-C_6$ alkyl;

or $R_{15}$ and $R_{16}$ together with the nitrogen atom to which they are attached can form a succinimido or phthalimido group or a fused ring derivative thereof, wherein said succinimido or phthalimido group or fused ring derivative thereof can be optionally substituted by up to three substituents independently selected from $NO_2$ and halogen; and z is 1 to 6.

In some embodiments, $R_{15}$ and $R_{16}$ are each methyl, preferably wherein z is 2 or 3, further preferably where $R_{52}$ and $R_{53}$ are each independently H, $C_{1-6}$ alkyl, alkoxy optionally substituted with dialkylamino, or alkylamino. In further embodiments, $R_{52}$ is H, preferably where $R_{53}$ is methyl, methoxy, alkoxy optionally substituted with dialkylamino, or alkylamino, preferably wherein $R_{53}$ is $OCH_3$ or $O(CH_2)_3N(CH_3)_2$.

In some embodiments, where $R_{15}$ and $R_{16}$ are each methyl, z is 2 or 3 and $R_{52}$ is H, $C_{1-6}$ alkyl, alkoxy optionally substituted with dialkylamino, or alkylamino, $R_{53}$ is H. In some such embodiments, $R_{52}$ is methyl, methoxy, alkoxy optionally substituted with dialkylamino, or alkylamino. In further embodiments, $R_{52}$ is $OCH_3$ or $O(CH_2)_3N(CH_3)_2$.

Also provided by the present invention are compounds having the Formula:

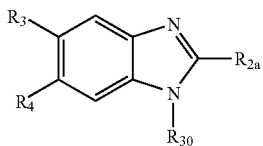

wherein:
$R_{2a}$ is amino, phenyl, mono- or bicyclic heterocycloalkyl having 1 or 2 ring nitrogen atoms, mono- or bicyclic heteroaryl having 1 or 2 ring nitrogen atoms, cycloalkyl, halogen, heterocycloalkylalkyl (i.e., alkyl sub w' heterocycloalkyl) having 1 or 2 ring nitrogen atoms, mono- or bicyclic heterocycloalkylamino having 1 or 2 ring nitrogen atoms or a group of formula —S-alkylene-$L_1$ where $L_1$ is mono- or bicyclic-heteroaryl having 1 or 2 ring nitrogen atoms;
wherein each of said amino, phenyl, heterocycloalkyl, heteroaryl, cycloalkyl, heterocycloalkylalkyl, or heterocycloalkylamino groups can be optionally substituted with a group selected from amino, OH, $C_1$–$C_{12}$ alkyl, a structure of formula —C(=O)CH($NH_2$)—$L_2$ where $L_2$ is the side chain of a naturally occurring alpha amino acid, —C($NH_2$)=NH, $C_1$–$C_{12}$ alkylcarbonyl, mono- or bicyclic heteroaryl having 1 or 2 ring nitrogen atoms, mono- or bicyclic heteroarylalkyl having 1 or 2 ring nitrogen atoms, or S-alkyl-heteroaryl where said heteroaryl is mono- or bicyclic having 1 or 2 ring nitrogen atoms; and $R_3$ and $R_4$ are each independently halogen, amino, $NO_2$, CN, $C_{1-6}$ alkoxy or $C_{1-6}$ alkyl optionally substituted with up to 3 halogen atoms; and $R_{30}$ is H, alkyl, aryl, arylalkyl, heteroaryl; heteroarylalkyl, heterocycloalkyl, arylsulfonyl, aryloxycarbonyl, alkoxyalkoxyalkyl, alkyl-S—$R_7$, alkyl-NH—C(=O)—$R_8$ or $R_9$—X—$R_{10}$—$R_{11}$)H;
wherein each of the alkyl, aryl, arylalkyl heteroaryl, heteroarylalkyl, heterocycloalkyl, arylsulfonyl, aryloxycarbonyl and alkoxyalkoxyalkyl moieties in each of the foregoing $R_1$ groups can be optionally substituted with up to 3 groups independently selected from the group consisting of $C_1$–$C_6$ alkyl, OH, hydroxyalkyl, —C(=O)—$R_5$; CN, aryl, alkoxycarbonyl, alkylaryl, arylalkyl, heteroaryl, S-heteroaryl optionally substituted with halogen, heteroarylalkyl optionally substituted with halogen, heterocycloalkyl optionally substituted with amino, $NO_2$, halogen, monohaloalkyl, dihaloalkyl, trihaloalkyl, perhaloaryl, perhaloalkylaryl, alkyl-$NR_{15}R_{16}$ and $NR_{15}R_{16}$;
or one of said alkyl, aryl, arylalkyl heteroaryl, heteroarylalkyl, heterocycloalkyl, arylsulfonyl, aryloxycarbonyl or alkoxyalkoxyalkyl moieties of one of said $R_1$ groups can be attached to a structure of Formula I at position $R_1$ thereof;

$R_5$ is H, —$NHNHR_6$, —NHN=CH—$R_6$, heteroaryl, heterocycloalkyl, wherein said hereteroaryl group can be optionally substituted with an aryl or heteroaryl group;

$R_6$ is aryl, heteroaryl; arylsulfonyl, heteroarylsulfonyl, —C(=S)—NH-aryl, —C(=S)—NH-arylcarbonyl, —C(=S)—NH-heteroarylcarbonyl, —C(=S)—NH-alkylene-$R_{21}$, —C(=O)—NH-aryl, —C(=O)—NH-arylcarbonyl, —C(=O)—NH-heteroarylcarbonyl, or —C(=O)—NH-alkylene-$R_{21}$ where $R_{21}$ is carboxy, alkoxycarbonyl, aryl, heteroaryl, heterocycloalkyl, arylaminocarbonyl, cycloalkylaminocarbonyl, or a saturated hydrocarbon, fused ring system optionally having an aryl ring fused thereto, said ring system being optionally substituted with up to three alkyl groups on the alkyl or aryl rings thereof;
wherein any of said $R_6$ groups can be optionally substituted with up to 3 groups selected from $NR_{15}R_{16}$, alkyl, hydroxy, halogen, aryl, alkoxy, trihaloalkoxy, arylalkyloxy, $NO_2$, —SH, —S-alkyl, heteroarylcarbonyl, heteroaryl, alkylheteroaryl, or a moiety of formula —$OC_2H_2$—O— attached to adjacent atoms of said $R_6$ group;

$R_7$ is heteroaryl or heterocycloalkyl;
$R_8$ is aryl;
$R_9$ and $R_{10}$ are each independently alkylene having from 1 to about 20 carbons;
X is —N($R_{12}$)—, —C($R_{13}$)($R_{14}$)— or O;
$R_{11}$ is H, heterocycloaryl or alkoxy, wherein said heterocycloaryl or alkoxy group can be optionally substituted with up to four groups independently selected from halogen, amino, trihaloalkyl, alkoxycarbonyl, and CN;
$R_{12}$ is H or $C_1$–$C_6$ alkyl; and
$R_{13}$ and $R_{14}$ are each independently H or $C_1$–$C_6$ alkyl;
$R_{15}$ is H, halogen, $C_{1-12}$ alkyl, methylcarbonyl, heterocycloalkyl, arylsulfonyl, heteroarylalkyl, aminoalkyl, arylcarbonyl, branched and straight chain polyaminoalkyl, or a group of formula $CH_2(CHOH)_4CH_2OH$,
wherein said methylcarbonyl, heterocycloalkyl, arylsulfonyl, heteroarylalkyl, aminoalkyl, arylcarbonyl, and branched and straight chain polyaminoalkyl groups can be substituted by up to 3 OH groups;
$R_{16}$ is H, halogen, or $C_1$–$C_6$ alkyl;
or $R_{15}$ and $R_{16}$ together with the nitrogen atom to which they are attached can form a succinimido or phthalimido group or a fused ring derivative thereof, wherein said succinimido or phthalimido group or fused ring derivative thereof can be optionally substituted by up to three substituents independently selected from $NO_2$ and halogen, or a group of Formula I at position $R_1$ thereof;
or $R_{15}$ and $R_{16}$ together with the nitrogen atom to which they are attached can form a group of Formula I wherein said nitrogen atom is $Q_4$ thereof;

In some such embodiments, $R_3$ and $R_4$ are each halogen, preferably chlorine. In further embodiments, $R_{2a}$ is amino, Cl, phenyl, monocyclic heterocycloalkyl having 1 or 2 ring nitrogen atoms, monocyclic heteroaryl having 1 ring nitrogen atom, cyclopenyl, cyclohexyl, heterocycloalkyl-methyl, piperidine-4yl amino or a group of formula —S—($C_{2-4}$ alkylene)—N-phthalimido; wherein each of said phenyl, heterocycloalkyl heteroaryl, cyclopenyl, cyclohexyl, heterocycloalkyl-methyl, and piperidine-4-yl amino groups can be optionally substituted with a group selected from NH$_2$, OH, CH$_3$, COOCH$_3$, a structure of formula —C(=O)CH(NH$_2$)—L$_2$ where L$_2$ is a serine or threonine side chain, —C(NH$_2$)=NH, benzimidazolyl, or benzimidazolemethylyl.

In further embodiments, R$_{2a}$ is amino, Cl, piperidinyl, pyridinyl, phenyl, cyclopentyl, cyclohexyl, pyrrolidinyl, piperazinyl, —CH$_2$-piperazinyl, piperidine-4-yl-amino or S-alkyl-phthalyl, wherein said piperidinyl, pyridinyl, phenyl, cyclopentyl, cyclohexyl, pyrrolidinyl, piperazinyl, —CH$_2$-piperazinyl, or S-alkyl-phthalyl groups can be optionally substituted with a group selected from NH$_2$, methylcarbonyl, —C(=O)CH(NH$_2$)—CH$_2$OH, methyl, OH, —C(NH$_2$)=NH, OH, benzimidazole-2-yl, and —CH$_2$-benzimidazole-2-yl.

In still further embodiments, R$_{2a}$ is amino, Cl, piperidinyl, pyridinyl, phenyl, cyclopentyl, cyclohexyl, pyrrolidinyl, piperazinyl, —CH$_2$-piperazinyl, piperidine-4-yl-amino or S-alkyl-phthalyl, wherein said piperidinyl, pyridinyl, phenyl, cyclopentyl, cyclohexyl, pyrrolidinyl, piperazinyl, —CH$_2$-piperazinyl, or S-alkyl-phthalyl groups can be optionally substituted with a group selected from NH$_2$, methylcarbonyl, —C(=O)CH(NH$_2$)—CH$_2$OH, methyl, OH, —C(NH$_2$)=NH, OH, benzimidazole-2-yl, and —CH$_2$-benzimidazole-2-yl.

In further embodiments, R$_{2a}$ is amino, Cl, pyridin-4-yl, phenyl substituted with amino, cyclopentyl substituted with amino, cyclohexyl optionally substituted with amino, pyrrolidin-2-yl optionally substituted by hydroxy, piperazin-1-yl optionally substituted at the 4-yl position by benzimidazole-2-yl, piperazin-1-yl-methyl optionally substituted at the 4-yl position by —CH$_2$-benzimidazole-2-yl, piperidine-4-yl-amino, piperidin-1-yl substituted by amino, S-alkyl-phthalyl, or said R$_2$ is piperidin-4-yl optionally substituted at the 1-yl position with —C(=O)CH$_3$, —C(=O)CH(NH$_2$)—CH$_2$OH, —C(NH$_2$)=NH, or CH$_3$.

In still further embodiments, R$_{2a}$ is amino, piperidin-4-yl-amino, piperiazine-1-yl optionally substituted with benzimidazole-2-yl, pyridin-4-yl, piperidin-4-yl optionally substituted at the 1-yl position with —C(=O)CH$_3$, —C(=O)CH(NH$_2$)—CH$_2$OH, —C(NH$_2$)=NH, or CH$_3$, 4-amino-piperdin-1-yl, 3-amino-phen-1-yl, 3-amino-cyclopent-1-yl, cyclohexyl optionally substituted at the 3-yl or 4-yl position with NH$_2$, 4-hydroxypyrrolidin-2-yl, piperazin-1-yl-methyl, 4-(benzimidazole-2-yl-methyl) piperazin-1-yl-methyl, or S-alkyl-phthalyl where said alkyl has from 2 to 4 carbons.

In still further embodiments, R$_{2a}$ is piperidin4-yl optionally substituted at the 1-yl position with —C(=O)CH$_3$, —C(=O)CH(NH$_2$)—CH$_2$OH, —C(NH$_2$)=NH, or CH$_3$.

In further embodiments where R$_3$ and R$_4$ are each chlorine, R$_{2a}$ is piperidin-4-yl optionally substituted at the 1-yl position with —C(=O)CH$_3$, —C(=O)CH(NH$_2$)—CH$_2$OH, —C(NH$_2$)=NH, or CH$_3$.

In some embodiments, R$_{2a}$ is piperidin-4-yl, and, preferably R$_3$ and R$_4$ are each chlorine. In some embodiments, R$_{2a}$ is NH$_2$, preferably wherein R$_3$ and R$_4$ are each chlorine.

In some embodiments where R$_3$ and R$_4$ are each chlorine and R$_{2a}$ is piperidin-4-yl, R$_{30}$ is alkyl substituted with —C(=O)—R$_5$, preferably wherein R$_5$ is —NHNHR$_6$, or —NHN=CH—R$_6$.

In some such embodiments, R$_5$ is —NHNHR$_6$ where R$_6$ is —C(=O)—NH-aryl, —C(=O)—NH-cycloalkyl, —C(=S)—NH-aryl, arylsulfonyl, heteroarylsulfonyl, heterocycloalkyl, arylaminocarbonyl, cycloalkylaminocarbonyl, —C(=S)—NH-alkylene-R$_{21}$ where R$_{21}$ is heteroaryl or heterocycloaryl, or a saturated hydrocarbon fused ring system optionally having an aryl ring fused thereto, said ring system being optionally substituted with up to three alkyl groups on the alkyl or aryl rings thereof;

wherein any of said R$_6$ groups can be optionally substituted with up to 3 groups selected from NR$_{15}$R$_{16}$, NO$_2$, a moiety of formula —OC$_2$CH$_2$—O— attached to adjacent atoms of said R$_6$ group, aryl, C$_{1-6}$ alkoxy, carboxy, or C$_{1-6}$ trihaloalkoxy.

In some embodiments, R$_5$ is —NHN=CH—R$_6$. In some such embodiments, R$_6$ is aryl or heteroaryl optionally substituted with up to 3 groups selected from OH, C$_{1-6}$ alkoxy, NO$_2$, C$_{1-6}$ trihaloalkoxy, C$_{1-6}$ trihaloalkyl, aryl, arylalkyloxy, and a moiety of formula —OC$_2$CH$_2$—O— attached to adjacent atoms of said R$_6$ group.

In some embodiments wherein R$_{2a}$ is piperidin-4-yl, R$_{30}$ has the formula —(CH$_2$)$_q$—L$_4$ where q is 0 to 6 and L$_4$ is aryl, heteroaryl or heterocycloalkyl, arylsulfonamino, arylcarboxyamino or —S-heteroaryl, where each of said L$_4$ is optionally substituted with up to three substituents selected from halogen and NO$_2$. Preferably, said L$_4$ is maleimido, succinimido, phthalimido, naphthalimido, pyromellitic diimido, phenylsulfonamido, phenylcarboxamido, benzopyrrolidine, benzimidazole, triazole, or —S-benzimidazole.

Also provided by the present invention are compounds of Formula:

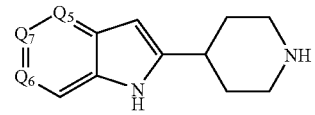

wherein:
Q$_5$ is CH or N;
Q$_6$ is C—R$_{61}$ or N;
Q$_7$ is C—R$_{60}$ or N;
R$_{60}$ and R$_{61}$ are each independently H, halogen, C$_{1-6}$ alkyl, trihaloalkyl, or C$_{1-6}$ alkoxy, provided that when Q$_6$ is C—R$_{61}$, Q$_7$ is C—R$_{60}$ and Q$_5$ is CH, then R$_{60}$ and R$_{61}$ are not both H.

In some embodiments, Q$_5$ is N. In further embodiments, Q$_6$ is N.

In some embodiments, Q$_7$ is N. In further embodiments, Q$_5$ is N, Q$_6$ is C—R$_{61}$ and Q$_7$ is C—R$_{60}$. In further embodiments, Q$_7$ is N, Q$_6$ is C—R$_{61}$ and Q$_5$ is CH. In further embodiments, Q$_5$ is N, Q$_6$ is N and Q$_7$ is C—R$_{60}$. In further embodiments, Q$_5$ is CH, Q$_6$ is R$_{61}$ and Q$_7$ is C—R$_{60}$.

In some embodiments where Q$_5$ is CH, Q$_6$ is R$_{61}$ and Q$_7$ is C—R$_{60}$, R$_{60}$ and R$_{61}$ are each independently H, Br, Cl, methoxy, methyl or trifluoromethyl. In further such embodiments, R$_{60}$ is OCH$_3$ and R$_{61}$ is H, or R$_{60}$ is CH$_3$ and R$_{61}$ is H, or R$_{60}$ is Br and R$_{61}$ is H, or R$_{60}$ is Cl and R$_{61}$ is H, or R$_{60}$ is CF$_3$ and R$_{61}$ is H, or R$_{60}$ is Cl and R$_{61}$ is CH$_3$, or R$_{60}$ and R$_{61}$ are both Cl.

The present invention provides methods for treating a patient having a bacterial infection comprising administering to said patient a compound of claim 1. Preferably, said patient is a human. Also provided are methods for inhibiting bacterial growth comprising contacting a bacterium with a compound of the invention. In some preferred embodiments, said bacterium is S. aureus, E. hirae, S. pyogenes, S. pneumoniae, E. coli, P. vulgaris, K. pneumoniae, P. aeruginosa, C. albicans, E. faecalis, E. faecali, or E. faecium.

The present invention also provides compositions that include at least one compound of the invention.

As used herein the term alkyl is intended to have it accustomed meaning of a straight or branched chain hydrocarbon, for example, methyl, ethyl, n-propyl, isopropyl, n-butyl, sec-butyl, t-butyl, n-pentyl, sec-pentyl, t-pentyl, neopentyl, and the like.

As used herein the term aryl is intended to mean an aromatic hydrocarbon system for example phenyl, naphthyl, phenanthrenyl, anthracenyl, pyrenyl, and the like. In some embodiments, aryl groups have from 6 to 10 carbon atoms.

As used herein, the term arylalkyl (or "aralkyl") is intended to mean an alkyl group that has an aryl group appended thereto, for example benzyl and naphthylmethyl groups. In some embodiments, arylalkyl groups have from 7 to 11 carbon atoms.

As used herein, the term alkylaryl (or "alkaryl") is intended to mean an aryl group that has one or more alkyl groups appended thereto, for example a 4-methylphen-1-yl group, or a xylyl group attached through the phenyl ring thereof.

As used herein, the term heteroaryl means an aryl group that contains one or more ring hetero (i.e., non-carbon) atoms, which are preferably O, N or S, more preferably N. In some embodiments, heteroaryl groups are monocyclic or bicyclic, and have up to four ring nitrogen atoms. Examples of some preferred heteroaryl groups include radicals derived from pyrrole, pyrazole, imidazole, triazoles, tetrazole, pyridine, pyrazine, pyridazine, pyrimidine, triazines, quinolines, indoles, benzimidazoles, and the like.

As used herein, the term heteroarylalkyl is intended to mean an alkylene group that has a heteroaryl group appended thereto, for example a group of formula —CH$_2$-benzimidazol-2-yl.

As used herein, the term cycloalkyl refers to nonaromatic hydrocarbon ring systems, for example cyclopropyl, cyclobutyl, cyclopentyl, cyclohexyl, including multiple ring systems such as decahydronaphthalene and adamantane. Cycloalkyl groups can also include points of unsaturation, and therefor also include cyclopentenyl, and cyclohexenyl groups.

As used herein, the term heterocycloalkyl is intended to mean a group that contains a nonaromatic ring which contains one or more ring hetero (i.e., non-carbon) atoms which are preferably O, N or S, more preferably N. Also included in the definition of heterocycloalkyl are moieties that contain exocyclic heteroatoms, for example a cycloalkyl ring having a ring carbon attached to an exocyclic O or S atom through a double bond. Also included in the definition of heterocycloalkyl are moieties that having one or more aromatic rings fused (i.e., having a bond in common with) to the nonaromatic heterocyclic ring, for example phthalimidyl, naphthalimidyl pyromellitic diimidyl, phthalanyl, and benzo derivatives of saturated heterocycles such as indolene and isoindolene groups.

As used herein, the term arylsulfonyl is intended to mean a moiety of formula —S(=O)$_2$-aryl, for example phenylsulfonyl. The term heteroarylsulfonyl means a moiety of formula —S(=O)$_2$-heteroaryl, for example pyridinesulfonyl.

As used herein the term aryloxy is intended to mean an aryl group attached through an oxygen atom, for example phenoxy.

As used herein, the term aryloxycarbonyl is intended to mean a moiety of formula —C(=O)—O-aryl, for example phenoxycarbonyl.

As used herein, the term alkoxyalkoxyalkyl is intended to mean a moiety of formula -alkylene-O-alkylene-O-alkyl.

As used herein, the term hydroxyalkyl is intended to mean an alkyl group that has a hydrogen atom thereof replaced with OH.

As used herein, the term alkoxycarbonyl is intended to mean a moiety of formula —C(=O)—O-alkyl.

As used herein, the term amino refers to NH$_2$. The term halogen includes F, Cl, Br and I. The prefix "halo" is intended to denote a halogen atom. The term "perhalo" is intended to refer to the substitution of all hydrogen atoms for halogen atoms. Thus, the term "perhaloaryl" indicated a fully halogenated moiety, for example a pentafouorophenyl radical, and the term "perhaloalkylaryl" would be understood to indicate a full halogenated alkylaryl group, for example a 2,3,5,6, tetrafluoro-4-trifluoromethyl-phenyl radical.

In one aspect, the present invention provides dimeric compounds wherein two benzimidazole core structures are joined, preferably at the 1-position, by a tether. Thus, in certain embodiments, various moieties appended to the 1-position of the benzimidazole core can be appended to a benzimidazole core structure at the 1-position thereof.

As used herein, the term alkoxy means moieties of formula —O-alkyl. The term arylcarbonyl means a moiety of formula —C(=O)-aryl. The term heteroarylcarbonyl means a moiety of formula —C(=O)-heteroaryl.

The term arylaminocarbonyl means a moiety of formula —C(=O)—NH-aryl. The term cycloalkylaminocarbonyl means a moiety of formula —C(=O)—NH-cycloalkyl.

The phrase "saturated hydrocarbon fused ring system optionally having an aryl ring fused thereto" is intended to denote saturated hydrocarbon ring systems having up to three fused rings, for example decalin, which can optionally have an aryl ring fused thereto, for example benzo derivatives of cycloalkyl groups.

The term arylalkyloxy denotes a group of formula —O-alkyl-aryl, for example a benzyloxy group. The term alkylheteroaryl denotes a group of formula -heteroaryl-alkyl, for example a 4-methyl-pyrid-2-yl group.

The phrase "moiety of formula —OCH$_2$CH$_2$—O— attached to adjacent atoms of" is intended to mean that the —OCH$_2$CH$_2$—O— oxygen atoms are attached to adjacent atoms an indicated moiety (which preferably is a cyclic group) to form a 6 membered fused ring comprising the —OCH$_2$CH$_2$—O— group and the two atoms to which it is attached.

The term methylcarbonyl is intended to denote an acetoyl (i.e., CH$_3$C(=O)—) group. The term aminoalkyl denotes a group of formula —alkyl—NH$_2$.

The phrase "branched and straight chain polyaminoalkyl" is intended to mean a group of formula —((CH$_2$)$_n$—NH)$_m$—H wherein n can be from 1 to 6 and m can be from 2 to about 12, in any one or more of the hydrogens attached to nitrogen can be replaced with a group of formula —((CH$_2$)$_p$—NH)$_q$—H where p is 1 to 6 and q is 1 to 12.

In some embodiments, compounds of the invention contain simple polyalchol moieties of formula —CH$_2$(CHOH)$_4$CH$_2$OH. It is intended that each such group specifically include each individual stereoisomer of such formula, as well as racemic forms of the same.

In certain embodiments, variables $R_{15}$ and $R_{16}$ together with the nitrogen atom to which they are attached can form a nitrogen heterocycle which can be aromatic or aliphatic, or aliphatic having one or more aromatic rings fused thereto (i.e., a fused ring derivative). Thus, in some embodiments, $R_{15}$ and $R_{16}$ together with the nitrogen atom to which they are attached can form, for example, an N-maleimidyl, N-succinimidyl, N-phthalimidyl, N-naphthalimidyl, N-pyromellitic diimidyl, N-benzopyrrolidinyl, or benzimidazol-1-yl group.

The term alkylamino is intended to denote a group of formula —NH-alkyl. The term aminoalkylamino is intended to denote a group of formula —NH-alkyl-NH$_2$. The term poly(aminoalkyl)amino is intended to denote a group of formula —NH—(alkyl-NH)$_x$—H where x is from 2 to about 12, and wherein any one or more of the hydrogens attached to nitrogen can be replaced with a group of formula —((CH$_2$)$_p$—NH)$_q$—H where p is 1 to 6 and q is 1 to 12.

The term heterocycloalkylamino is intended to denote a group of formula -NH-heterocycloalkyl. The term heterocycloalkylalkyl is intended to denote a group of formula alkyl-heterocycloalkyl).

The term "side chain of a naturally occurring alpha amino acid" is intended to mean the side chain of naturally occurring alpha amino acids, with the exception of glycine, that are known to have the formula H$_2$N—CHR—COOH, where R is the side chain. Examples of such naturally occurring amino acids include the 20 so called "essential" amino acids, for example serine and threonine. Further side chains of naturally occurring alpha amino acids can be found in Biochemistry, 3rd Edition, Matthews, Van Holde, and Ahern, Addison Wesley Longman, San Francisco, Calif., incorporated by reference herein in its entirety.

As used herein, the term alkoxyalkoxyalkyl is intended to denote a group of formula alkyl —O-alkyl-O-alkyl. The term hydroxyalkyl is intended to mean a hydroxy group that is substituted with up to 3 hydroxy groups. The term heteroarylcarbonyl denotes a moiety of formula —C(=O)-heteroaryl. The term arylaminocarbonyl denotes a moiety of formula —C(=O)—NH-aryl. The term cycloalkylaminocarbonyl denotes a moiety of formula —C(=O)—NH-cycloalkyl.

The compounds of the present invention and their pharmaceutically acceptable salts are useful in for the treatment of bacterial infections in animal and human subjects. The compounds of the invention can be used alone, or in a pharmaceutical composition containing one or more compounds of the invention, in combination with one or more pharmaceutically acceptable carriers. Thus, in further aspects, the present invention includes pharmaceutical compositions and methods of treating bacterial infections utilizing as an active ingredient the novel compounds described herein.

In some embodiments, the compounds of the invention can be prepared as amine salts, which can contain any of a variety of pharmaceutically acceptable counterions. Suitable counterions include acetate, adipate, aminosalicylate, anhydromethylenecitrate, ascorbate, aspartate, benzoate, benzenesulfonate, bromide, citrate, camphorate, camphorsulfonate, chloride, estolate, ethanesulfonate, fumarate, glucoheptanoate, gluconate, glutamate, lactobionate, malate, maleate, mandelate, methanesulfonate, pantothenate, pectinate, phosphate/diphosphate, polygalacturonate, propionate, salicylate, stearate, succinate, sulfate, tartrate and tosylate. Other suitable anionic species will be apparent to the skilled practitioner.

Representative examples of compounds of the invention are shown below. It is contemplated that the present invention include all possible protonated and unprotonated forms of the compounds disclosed herein.

The compounds of the invention can be formulated in pharmaceutical compositions which can include one or more compounds of the invention and one or more pharmaceutically acceptable carriers. The compounds of the invention can be administered in powder or crystalline form, in liquid solution, or in suspension. They may be administered by a variety of means known to be efficacious for the administration of antibiotics, including without limitation topically, orally and parenterally by injection (e.g., intravenously or intramuscularly).

When administered by injection, a preferred route of delivery for compounds of the invention is a unit dosage form in ampules, or in multidose containers. The injectable compositions may take such forms as suspensions, solutions, or emulsions in oily or aqueous vehicles, and may contain various formulating agents. Alternatively, the active ingredient may be in powder (lyophillized or non-lyophillized) form for reconstitution at the time of delivery with a suitable vehicle, such as sterile water. In injectable compositions, the carrier is typically comprised of sterile water, saline or another injectable liquid, e.g., peanut oil for intramuscular injections. Also, various buffering agents, preservatives and the like can be included.

Topical applications may be formulated in carriers such as hydrophobic or hydrophilic bases to form ointments, creams, lotions, in aqueous, oleaginous or alcoholic liquids to form paints or in dry diluents to form powders.

Oral compositions may take such forms as tablets, capsules, oral suspensions and oral solutions. The oral compositions may utilize carriers such as conventional formulating agents, and may include sustained release properties as well as rapid delivery forms.

The dosage to be administered depends to a large extent upon the condition and size of the subject being treated, the route and frequency of administration, the sensitivity of the pathogen to the particular compound selected, the virulence of the infection and other factors. Such matters, however, are left to the routine discretion of the physician according to principles of treatment well known in the antibacterial arts. Another factor influencing the precise dosage regimen, apart from the nature of the infection and peculiar identity of the individual being treated, is the molecular weight of the compound.

The compositions for human delivery per unit dosage, whether liquid or solid, may contain from about 0.01% to as high as about 99% of active material, the preferred range being from about 10–60%. The composition will generally contain from about 15 mg to about 2.5 g of the active ingredient; however, in general, it is preferable to employ dosage amounts in the range of from about 250 mg to 1000 mg. In parenteral administration, the unit dosage will typically include the pure compound in sterile water solution or in the form of a soluble powder intended for solution, which can be adjusted to neutral pH and isotonic.

The invention described herein also includes a method of treating a bacterial infection in a mammal in need of such treatment comprising administering to said mammal a compound of the invention in an amount effective to treat said infection. One preferred method of administration of the antibacterial compounds of the invention include oral and parenteral, e.g., i.v. infusion, i.v. bolus and i.m. injection.

Compounds provided herein can be formulated into pharmaceutical compositions by admixture with pharmaceutically acceptable nontoxic excipients and carriers. As noted above, such compositions may be prepared for use in parenteral administration, particularly in the form of liquid solutions or suspensions; or oral administration, particularly in the form of tablets or capsules; or intranasally, particularly in the form of powders, nasal drops, or aerosols; or dermally, via, for example, transdermal patches; or prepared in other suitable fashions for these and other forms of administration as will be apparent to those skilled in the art.

The composition may conveniently be administered in unit dosage form and may be prepared by any of the methods well known in the pharmaceutical art, for example, as described in *Remington's Pharmaceutical Sciences* (Mack Pub. Co., Easton, Pa., 1980). Formulations for parenteral administration may contain as common excipients sterile water or saline, polyalkylene glycols such as polyethylene glycol, oils and vegetable origin, hydrogenated naphthalenes and the like. In particular, biocompatible, biodegradable lactide polymer, lactide/glycolide copolymer, or polyoxyethylene-polyoxypropylene copolymers may be useful excipients to control the release of the active compounds. Other potentially useful parenteral delivery systems for these active compounds include ethylene-vinyl acetate copolymer particles, osmotic pumps, implantable infusion systems, and liposomes. Formulations for inhalation administration contain as excipients, for example, lactose, or may be aqueous solutions containing, for example, polyoxyethylene-9-lauryl ether, glycocholate and deoxycholate, or oily solutions for administration in the form of nasal drops, or as a gel to be applied intranasally. Formulations for parenteral administration may also include glycocholate for buccal administration, a salicylate for rectal administration, or citric acid for vaginal administration. Formulations for transdermal patches are preferably lipophilic emulsions.

The materials of this invention can be employed as the sole active agent in a pharmaceutical or can be used in combination with other active ingredients, e.g., other growth factors which could facilitate neuronal survival or axonal regeneration in diseases or disorders.

The concentrations of the compounds described herein in a therapeutic composition will vary depending upon a number of factors, including the dosage of the drug to be administered, the chemical characteristics (e.g., hydrophobicity) of the compounds employed, and the route of administration. In general terms, the compounds of this invention may be provided in effective inhibitory amounts in an aqueous physiological buffer solution containing about 0.1 to 10% w/v compound for parenteral administration. Typical dose ranges are from about 1 mg/kg to about 1 g/kg of body weight per day; a preferred dose range is from about 0.01 mg/kg to 100 mg/kg of body weight per day. Such formulations typically provide inhibitory amounts of the compound of the invention. The preferred dosage of drug to be administered is likely, however, to depend, on such variables as the type and extent of progression of the disease or disorder, the overall health status of the particular patient, the relative biological efficacy of the compound selected, and formulation of the compound excipient, and its route of administration.

As used herein, the term "contacting" means directly or indirectly causing at least two moieties to come into physical association with each other. Contacting thus includes physical acts such as placing the moieties together in a container, or administering moieties to a patient. Thus, for example administering a compound of the invention to a human patient evidencing a disease or disorder associated with abnormal and/or aberrant activity of such proteases falls within the scope of the definition of the term "contacting".

Compounds of the invention also are useful for in silico studies to determine potential binding to binding pockets present in a variety of bacteria, including those disclosed in the Examples herein. Thus, the present invention further provides methods for determining binding affinities for classes of compounds in silico. In the methods, representations of the compounds of the invention can be used in molecular modeling studies to determine such binding affinities, and therefore aid in the design of therapeutics.

While the present invention has been described with specificity in accordance with certain of its preferred embodiments, the following examples serve only to illustrate the invention and are not intended to limit the same.

EXAMPLES

Example 1

General Procedure for Preparation of Benzimidazoles Having Modification to the Phenyl (B) Ring The general procedure for preparation of benzimidazoles having modification to the phenyl (B) ring is shown in Scheme 1, below:

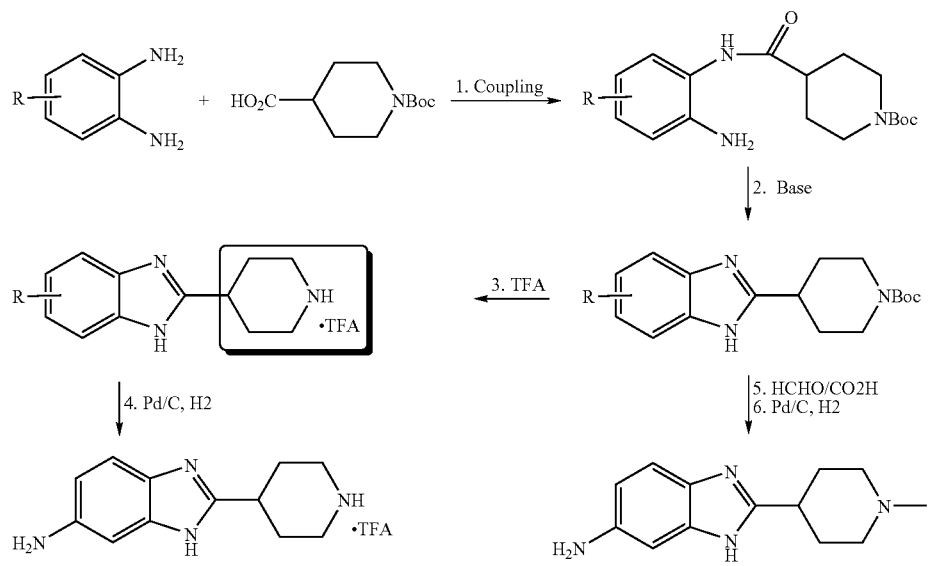

Generally, the steps of the synthesis are:

(1) N-Boc isonipecotic acid (25 g, 109 mmol) was dissolved in DMF (500 mL). HATU (49.5 g, 130 mmol) was added, followed by DMAP (16.0 g, 150 mmol) and DIEA (45 mL, 260 mmol). After the mixture was stirred for 30 minutes, diamine (105 mmol) was added and the resulting reaction mixture stirred overnight. The mixture was concentrated to one fourth of the volume, and poured into brine, extracted with dichloromethane (3×150 mL). The combined organic solution was dried over magnesium sulfate and concentrated too give black oil.

(2) The black oil was dissolved in ethanol (250 mL) and 2 M sodium hydroxide (250 mL). The mixture was refluxed overnight, cooled to room temperature and poured into saturated citric acid solution. The resulting mixture was extracted with dichloromethane (4×150 mL), and the combined organic solution was dried over magnesium sulfate and concentrated too give a black oil, which was purified on silica gel with ethyl acetate and dichloromethane to give the desired product.

(3) N-Boc compound (0.02 mmol) was placed in a 2-drum vial with a stirbar, and hydrochloric acid in dioxane (6.0 M, 500 L) was added. The mixture was stirred at room temperature for 30 minutes to give the corresponding product as precipitate (hydrochloride salt). The mixture was centrifuged, the solution removed using a pipette, and the solid salt was dried under vacuum overnight.

(4) 4-Nitro Benzimidazole hydrochloride salt (0.02 mmol), prepared by the procedure above was dissolved in methanol (2.0 mL), followed by the addition of palladium on carbon (10%, 5 mg). The resulting mixture was hydrogenated with a hydrogen balloon at room temperature for two hours. The catalyst was filtered off and washed with methanol (3×1.0 mL). The combined methanol solution was concentrated and dried under vacuum overnight.

(5) N-Boc benzimidazole (0.04 mmol) was dissolved in formic acid (1.0 mL) and formaldehyde (1.0 mL, 37%), and the mixture was heated at 120° C. with an oil bath for 3 hours. Ethyl acetate (5.0 mL) was added, followed by excess solid sodium bicarbonate to neutralize the acid. The mixture was extracted with ethyl acetate (4×5 mL), and the combined organic solution was dried over magnesium sulfate and concentrated too give the crude product, which was purified on silica gel with methanol in chloroform (5%, 10% and 20%, 20%) and 2% $NH_3 \blacksquare H_2O$ and 20% MeOH in $CHCl_3$. (1694–5)

[1] H NMR (200 MHz, $CDCl_3$): 8.44 (s, 1H), 8.12 (d, J=9.0 Hz, 1H), 7.56 (d, J=9.0 Hz, 1H) 3.60–3.40 (m, 1H), 3.20–2.90 (m, 2.H), 2.35 (s, 3H), 2.30–2.00 (m, 5H) LC/MS: $M+H^{3o}$=261

(6) 4-Nitro Benzimidazole from step (4) (0.02 mmol) was dissolved in methanol (2.0 mL), followed by the addition of palladium on carbon (10%, 5 mg). The resulting mixture was hydrogenated with a hydrogen balloon at room temperature for two hours. The catalyst was filtered off and washed with methanol (3×1.0 mL). The combined methanol solution was concentrated and dried under vacuum overnight.

Example 2

General Procedure for Synthesis of Benzimidazoles Having Modification to the Imidazole (A) Ring The general procedure for preparation of benzimidazoles having modification to the imidazole (A) ring is shown in Schemes 2 and 3, below:

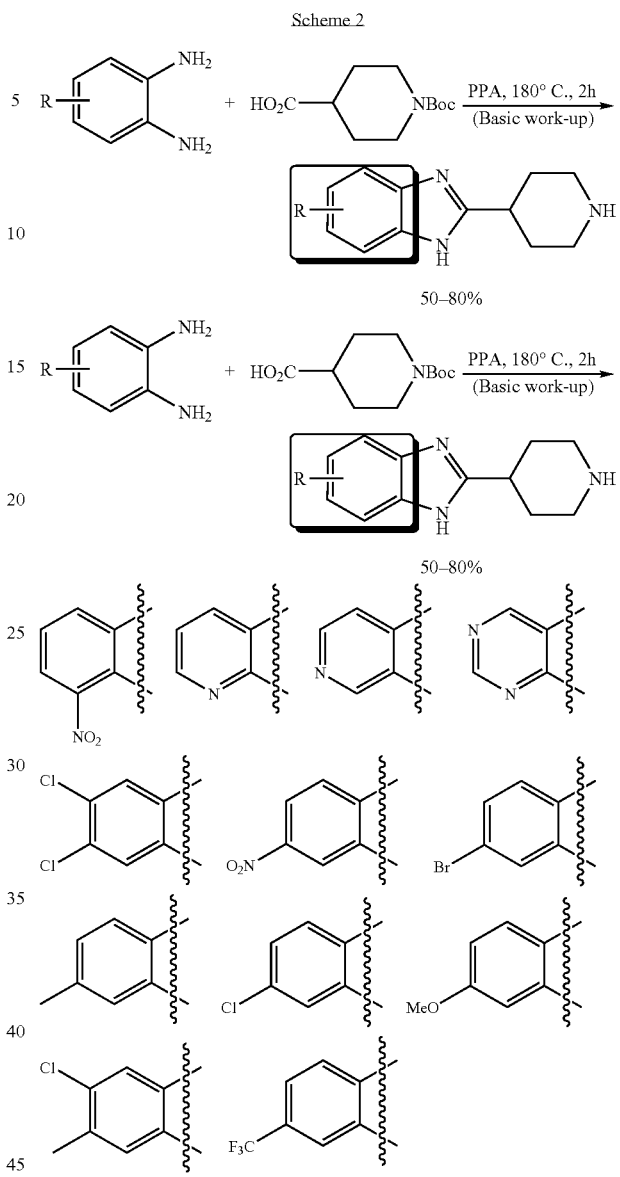

Aryl diamines (1.0 mmol) and isonipecotic acid (129 mg, 1.2 mmol) were grounded into powder and well mixed. Polyphosphoric acid (PPA, 1.0 g) was then added. The mixture was heated in an oil-bath at 180° C. for two hours. The syrup was cooled to room temperature, and saturated sodium hydroxide was added to make the resulting mixture basic. The mixture was extracted with 30% isopropanol in chloroform (5×30 mL), and the combined organic solution was dried over magnesium sulfate and concentrated. The crude product was then purified by silica gel chromatography using methanol in chloroform (5%, 10% and 15%).

Rf=0.15 (2% $NH_3 \blacksquare H_2O$ and 20% $^i$PrOH in $CHCl_3$)

LC/MS: $M+H^{3o}$=202 (2 G column)

$^1$H NMR (200 MHz, $CDCl_3$): 7.55–7.44 (m, 2 H), 7.23–7.13 (m 2H), 3.34–2.98 (m, 3H), 2.83–2.66 (m, 2H), 2.14–2.00 (m, 2H), 1.96–1.72 (m, 2H).

Scheme 3

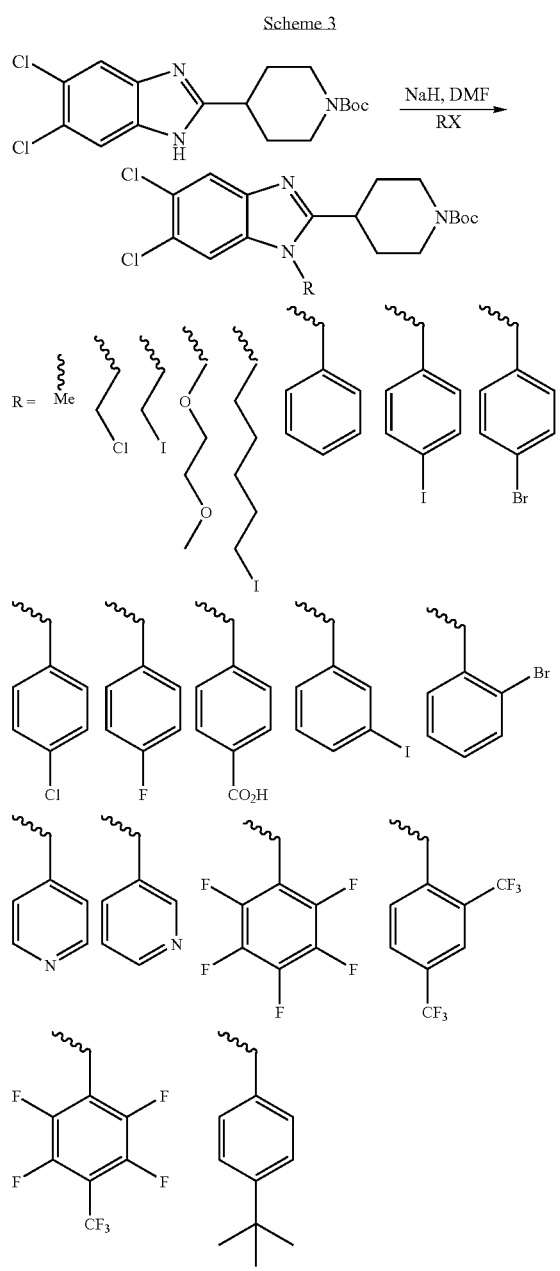

(1) Sodium hydride (24 mg, 60%, 1 mmol) was washed with hexane (3×1 mL). Anhydrous CH$_3$CN (2.0 mL) was added, followed by N-Boc4,5-dichlorobenzimidazole (37 mg, 0.1 mmol) portion wise under argon. After the slurry was stirred at room temperature for 30 minutes, the alkylating halide (0.15 mmol) was added, and the reaction mixture was stirred at room temperature for another 30 minutes (The reaction progress was monitored by TLC). The reaction was cooled with an ice bath, and ice water (2.0 mL) was carefully added. The resulting crude mixture was extracted with ethyl acetate (3×10 mL), the combined organic solution was washed with brine (2×2 mL) and dried over magnesium sulfate and concentrated. The crude product was then purified by silica gel chromatography using ethyl acetate in hexane (10%, 20% and 30%).

Yield: 95%

Rf=0.15 (2% NH$_3$■H$_2$O and 20% $^i$PrOH in CHCl$_3$)

LC/MS: M+H$^{30}$=516 (2 CN column)

$^1$H NMR (200 MHz, CD$_3$OD): 7.29 (s, 1H), 7.62 (s, 1H), 7.42–7.40 (m, 2H), 7.05–6.85 (m, 2H), 5.5 (s, 2H), 4.20–4.02 (m, 2H), 3.25–3.10 (m, 1H), 2.92–2.72 (m, 2H), 1.45 (s, 9H), 1.28 (s, 3H).

(2) N-Boc compound (0.02 mmol) was placed in a 2-drum vial with a stirbar, and hydrochloric acid in dioxane (6.0 M, 500 L) was added. The mixture was stirred at room temperature for 30 minutes to give the corresponding product as precipitate (hydrochloride salt). The mixture was centrifuged, the solution removed using a pipette, and the solid salt was dried under vacuum over night.

Yield: 90%

LC/MS: M+H$^{30}$=202 (2 G column)

Example 4

General Procedure for Preparation of Benzimidazole Derivatives via Solid Phase Synthesis The general procedure for preparation of benzimidazole derivatives via solid phase synthesis is shown in Scheme 4, below:

Scheme 4

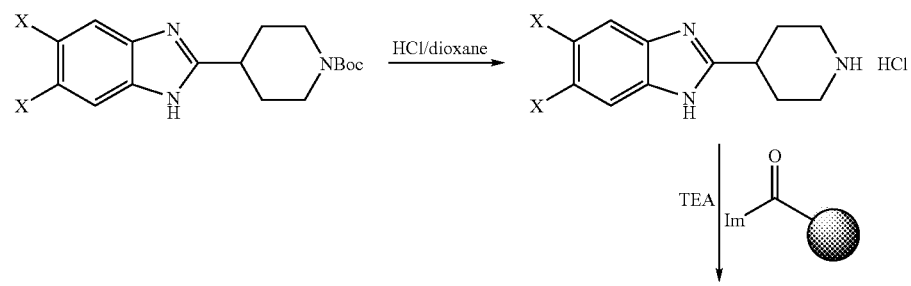

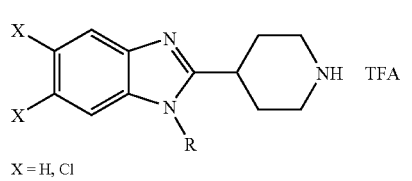
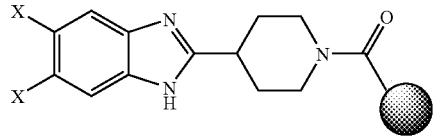

X = H, Cl (1) N-Boc-4,5-dichlorobenzimidazole (3.0 mg, 10.7 mmol) was powdered and treated with hydrogen chloride in dioxane (6 N) for 2 h. Dioxane was then evaporated and the corresponding hydrochloride salt was dried under vacuum overnight, which was directly used to attach to the Wang resin (2) Wang resin (15.0 g, 5.70 mmol) (Sigma-Aldrich 2000–2001 Catalog, item #47,703-6) was swollen in DMF (120 mL), and carbonyl diimidazole (1.84 g, 11.4 mmol) was added and the resulting mixture stirred at room temperature overnight. The resin was filtered off and washed successively with DMF (3×30 mL), dichloromethane (3×30 mL), diethyl ether (3×30 mL) and dried overnight. The resulting resin was again suspended in DMF (200 mL), all the benzimidazole hydrochloride salt obtained in step (1) was added, followed by triethylamine (3.0 mL, 21.6 mmol). The resulting mixture was stirred at room temperature overnight. The resin was filtered off and washed successively with DMF (3×30 mL), dichloromethane (3×30 mL), methanol (3×30 mL), diethyl ether (3×30 mL) and dried overnight.

(3) Benzimidazole on Wang resin obtained in step (2) (100 mg, ~0.0324 mmol) was suspended in DMF (2.0 mL), sodium hydride (60%, 50 mg, 1.250 mmol) was added and the mixture stirred for 15 minutes at room temperature. Alkylating halide (0.0972 mmol) was added, and the mixture was stirred for 2 hours at room temperature. The reaction flask was then cooled with ice bath, and water (100 L) was carefully added to react with the excess sodium hydride. The resin was filtered off and washed successively with water ((3×1.0 mL), DMF (3×1.0 mL), dichloromethane (3×3=1.0 mL), methanol (3×1.0 mL), diethyl ether (3×1.0 mL) and dried overnight.

(4) The resin obtained in step (3) was suspended in dichloromethane (1.4 mL), trifluoroacetic acid (600 L) was added and the mixture was gently stirred for 30 minutes at room temperature. The resin was then filtered off and washed with dichloromethane (5×1.0 mL). The dichloromethane solution was dried to give the benzimidazoles as trifluoroacetic acid salt.

Example 5

General Procedure for Preparation of Xylene-1-yl Benzimidazole Derivatives via Solid Phase Synthesis The general procedure for preparation of xylene-1-yl benzimidazole derivatives via solid phase synthesis is shown in Scheme 5, below:

Scheme 5

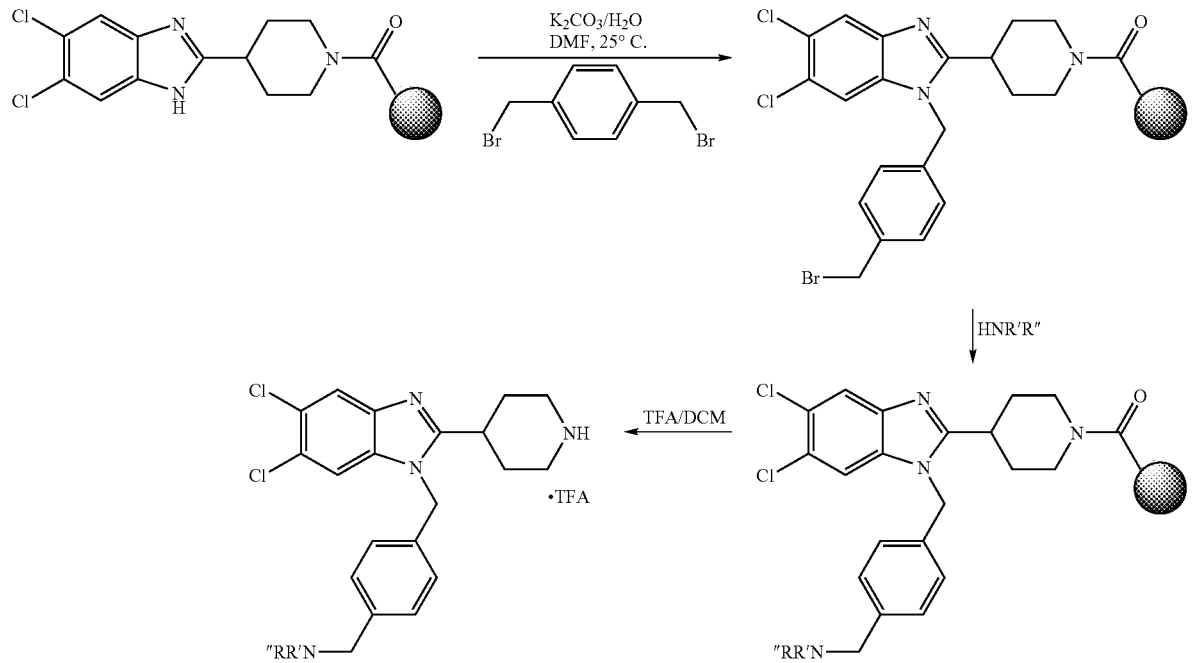

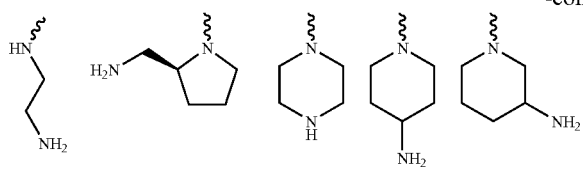

(1) Benzimidazole on Wang resin (2.0 g, ~0.65 mmol) was suspended in DMF (20.0 mL), saturated potassium carbonate (2.0 mL) was added, followed by α,α'-dibromo-p-xylene (860 mg, 3.25 mmol), and the resulting mixture was gently stirred at room temperature for 5 hours. The resin was filtered off and washed successively with water ((3×0.0 mL), DMF (3×10.0 mL), dichloromethane (3×3=10.0 mL), methanol (3×10.0 mL), diethyl ether (3×10.0 mL) and dried overnight.

(2) Benzyl bromide on resin obtained in step (1) (100 mg, 0.0324 mmol) was suspended in DMF (2.0 mL), and amine (0.324 mmol) was added. The reaction mixture was gently stirred at room for six hours. The resin was filtered off and washed successively with DMF (3×1.0 mL), dichloromethane (3×3=1.0 mL), methanol (3×1.0 mL), diethyl ether (3×1.0 mL) and dried overnight.

(3) The resin obtained in step (1) was suspended in dichloromethane (1.4 mL), trifluoroacetic acid (600 L) was added and the mixture was gently stirred for 30 minutes at room temperature. The resin was then filtered off and washed with dichloromethane (5×1.0 mL). The dichloromethane solution was dried to give the benzimidazoles as trifluoroacetic acid salt.

Example 6

General Procedure for Preparation of Benzimidazole Derivatives Having Urea or Thiourea Functionality The general procedure for preparation of benzimidazole derivatives having urea or thiourea functionality is shown below in Scheme 6:

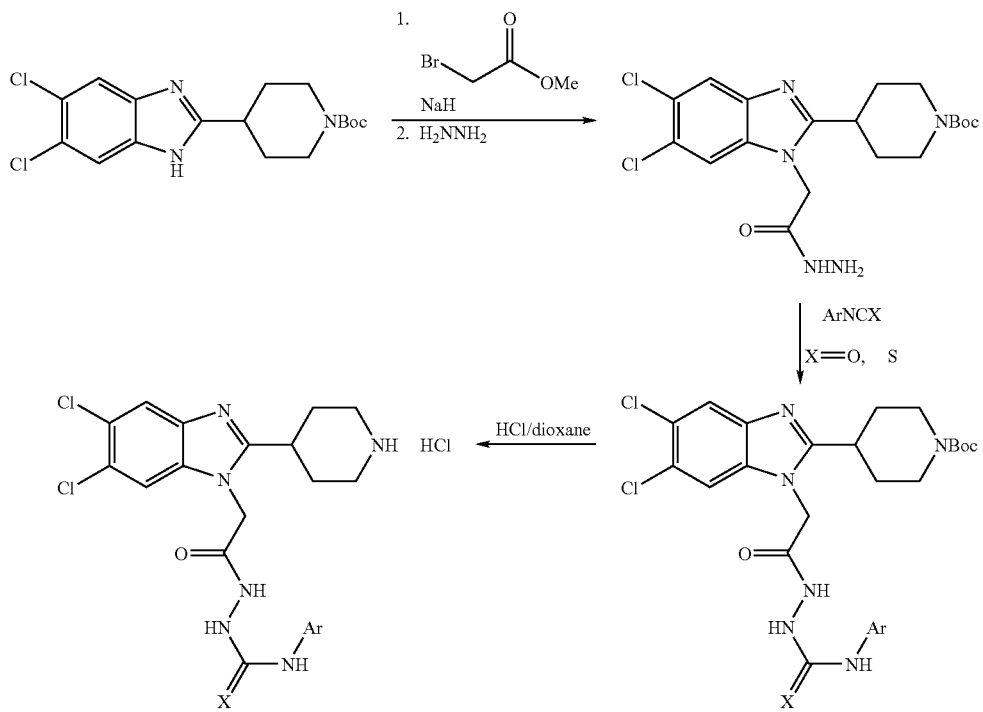

Scheme 6

(1) To a solution of N-Boc benzimidazole (200 mg, 0.54 mmol) in DMF (2.0 mL) was added sodium hydride (60%, 65 mg, 1.40 mmol) portion-wise, and the resulting mixture was stirred for 20 minutes. Methyl bromoacetate (214 mg, 1.40 mmol) was then added and the reaction mixture was stirred at room temperature for 2 hours. The reaction flask was then cooled with ice bath, and water (100 μL) was carefully added to react with the excess sodium hydride. The resulting mixture was then diluted with ethyl acetate (30 mL), washed with brine (5×2 mL) and dried over magnesium sulfate. The crude product was purified on silica gel with 50% ethyl acetate in hexane to give 210 mg (88%) of the desired methyl ester. (1815–41)

Rf=0.40 (AcOEt:Hexane=1:1)

LC/MS: M+H$^+$=442 (2CN column)

$^1$H NMR (200 MHz, CDCl$_3$): 7.80 (s, 1H), 7.38 (s, 1H), 4.95 (s, 2H), 4.40–4.15 (m, 3H), 3.78 (s, 3H), 3.00–2.78 (m, 2H), 2.10–1.80 (m, 6 H).

(2) To the solution of methyl ester (160 mg, 0.36 mmol) obtained form step 1) in methanol (5.0 mL) was added hydrazine (46.0 mg, 1.44 mmol), and the resulting mixture was stirred at room temperature for three hours. The reaction was then concentrated and the crude product purified on silica gel with 10% methanol in chloroform to give the corresponding acyl hydrazine (152 mg, 92%) Rf=0.15 (MeOH:CHCl$_3$=1:1)

(3) To the solution of acyl hydrazine (30 mg, 0.068 mmol) obtained from step 2) in chloroform (2.0 mL) was added isocynate or isothiocynate (0.068 mmol) at 0 C., and the reaction was warmed up and stirred at room temperature for one hour. TLC and LC/MS indicated complete conversion of the starting material and the product has more than 90% purity.

(4) Urea or thiourea (0.02 mmol) obtained in step 3) was powdered and treated with hydrogen chloride in dioxane (6 N) for 2 h. Dioxane was then evaporated and the corresponding hydrochloride salt was dried under vacuum overnight. LC/MS indicated complete conversion of starting material and desired product has over 90% purity.

Example 7

General Procedure for Preparation of Benzimidazole Derivatives Having Hydrazone Functionality The general procedure for preparation of benzimidazole derivatives having hydrazone functionality si shown below in Scheme 7:

(1) To the solution of acyl hydrazine (20 mg, 0.045 mmol) and aldehyde (0.0475 mmol) in THF (1.0 mL) was added catalytic amount of p-tolunesulfonic acid. The reaction mixture was stirred at room temperature for two hours, and dried. TLC and LC/MS indicated complete conversion of starting material and desired product has over 90% purity.

(2) Half of the N-Boc hydrazone obtained above (0.023 mmol) was powdered and treated with hydrogen chloride in dioxane (6 N) for 30 min. Dioxane was then evaporated and the corresponding hydrochloride salt was dried under vacuum overnight. LC/MS indicated complete conversion of starting material and desired product has over 90% purity.

Example 8

General Procedure for Preparation of Benzimidazole Derivatives Having Sulfonamide Functionality The general procedure for preparation of benzimidazole derivatives having sulfonamide functionality si shown below in Scheme 7:

Scheme 8

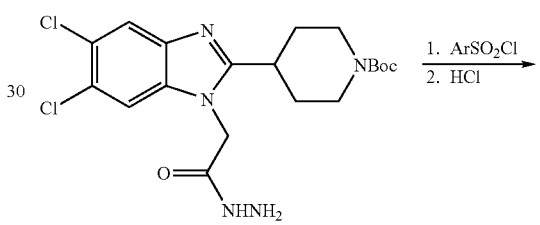

Scheme 7

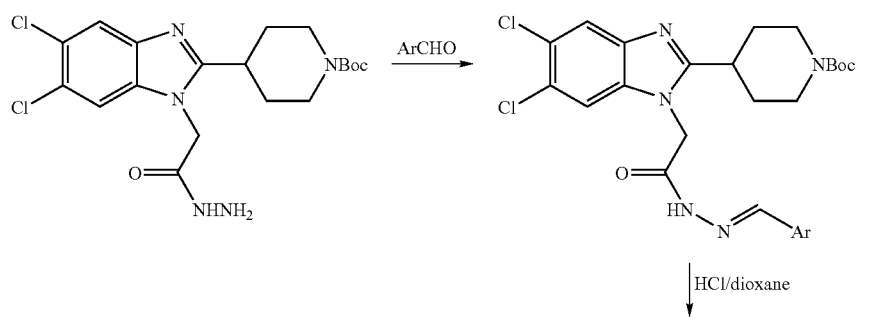

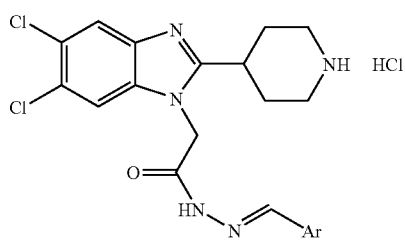

-continued

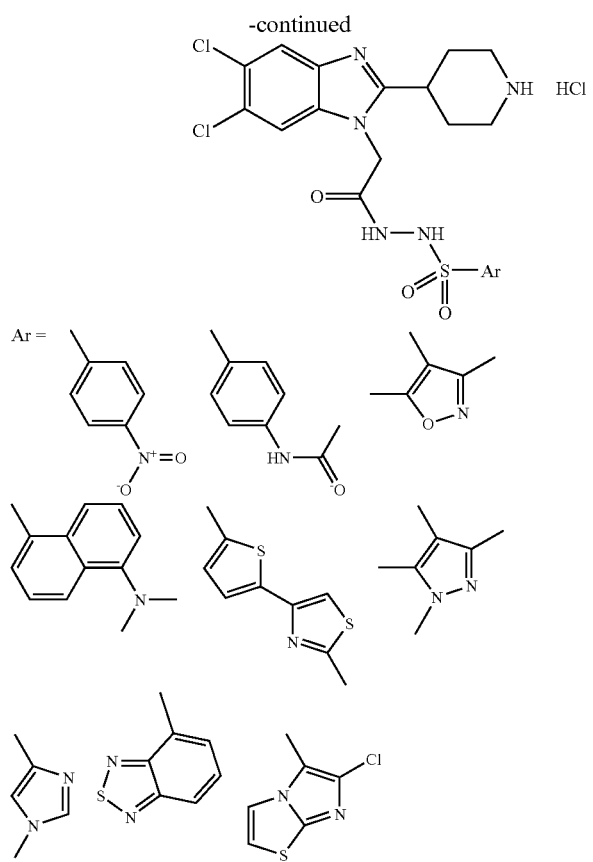

(1) To the solution of acyl hydrazine (20 mg, 0.045 mmol) and pyridine (6.0 mg, 0.072 mmol) and DMAP (catalytic) in 30% THF in CH₂Cl₂ was added sulfonyl chloride (0.0475 mmol). The reaction mixture was stirred at room temperature overnight, and dried. TLC and LC/MS indicated complete conversion of starting material and desired product has over 90% purity.

(2) Half of the N-Boc sulfonamide obtained above (0.023 mmol) was powdered and treated with hydrogen chloride in dioxane (6 N) for 2 h. Dioxane was then evaporated and the corresponding hydrochloride salt was dried under vacuum overnight. LC/MS indicated complete conversion of starting material and desired product has over 90% purity.

Example 9

General Procedure for Preparation of Benzimidazole Derivatives Having Substituted Alkyl Functionality The general procedure for preparation of benzimidazole derivatives having substitutued alkyl functionality is shown below in Scheme 9. While the procedure is illustrated for phthalimidyl-alkyl functionalization, the procedure is generally applicable to to the preparation of benzimidazoles having a wide variety of heterocycles attached through alkyl spacers.

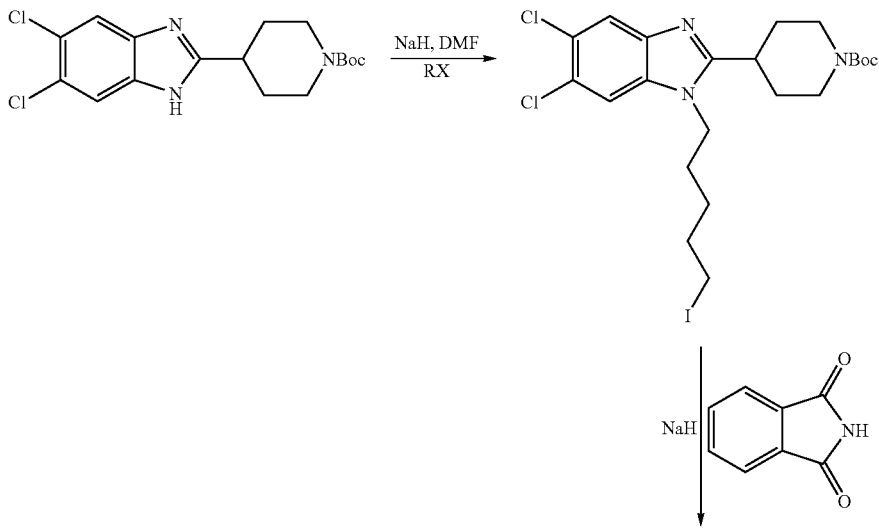

Scheme 9

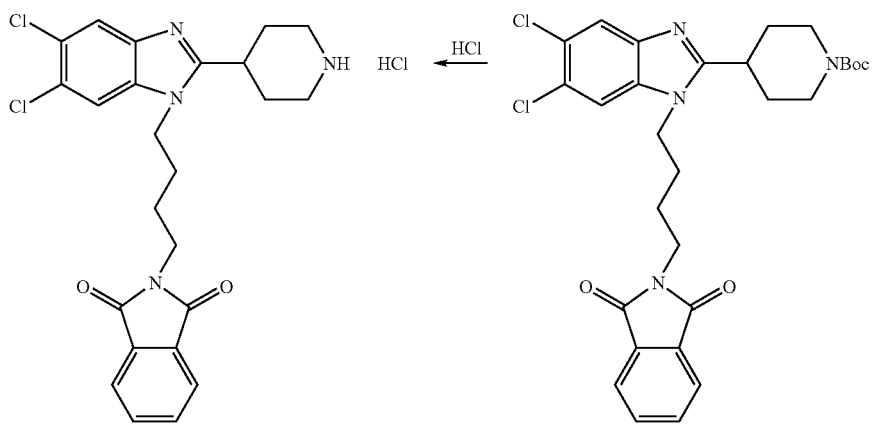

(1) To the solution of N-Boc benzimidazole (110 mg, 0.30 mmol), and diiodide (1.50 mmol) in DMF (3.0 mL) was added sodium hydride (60%, 120 mg, 3.0 mmol) portionwise. After the reaction mixture was stirred at room temperature for 20 minutes, the reaction flask was then cooled with ice bath, and water (100 mL) was carefully added to react with the excess sodium hydride. The resulting mixture was then extracted with ethyl acetate (3×10 mL) and the combined organic solution was Washed with brine and dried over magnesium sulfate. The crude product was purified on silica gel with 50% ethyl acetate in hexane.

Rf=0.55 (AcOEt:Hexane=1:1)

LC/MS: M+H$^+$=567 (2CN column)

$^1$H NMR (200 MHz, CDCl$_3$): 7.75 (s, 1H), 7.35 (s, 1H), 4.35–4.15 (m, 1H), 4.20–3.95(m, 2H), 3.20–3.00 (m, 2H), 2.00–1.20 (m, 12 H).

(2) To the solution of iodo benzimidazole obtained in step 1) (0.044 mmol), phthalimide or amide (0.066 mmol) in DMF (1.5 mL) was added potassium carbonate (11 mg, 0.066 mmol). After being stirred at room temperature overnight, the reaction mixture was diluted with 50 mL of ethyl acetate, washed with brine (5×2 mL), dried over magnesium sulfate and concentrated. The crude product was purified on silica gel with 50% ethyl acetate in hexane.

Rf=0.40 (AcOEt:Hexane=1:1)

LC/MS: M+H$^+$=631 (2CN column)

$^1$H NMR (200 MHz, CDCl$_3$): 8.70–8.55 (m, 3H), 8.10–8.00 (m, 1H), 7.78 (s, 1H), 7.41 (s, 1H), 4.40–4:00 (m, 3H), 3.82–3.70 (m, 2H), 3.08–2.80 (m, 2H), 2.00–1.20 (m, 12H).

Example 10

Biological Evaluation of Compounds

Compounds were evaluated for in vitro antibacterial activity (referred to MIC, the minimum concentration inhibiting fungal cell growth) against S. aureus and E. coli. Table 2 shows the in vitro inhibitorial activity of selected benzimidazoles against additional pathogenic strains of bacteria (four Gram positive strains, four gram negative strains and one yeast strain). The assays are carried out in 150 mL volume in duplicate in 96-well clear flat-bottom plates. The bacterial or yeast suspension from an overnight culture growth in appropriate medium is added to a solution of test compound in 2.5% DMSO in water. Final bacterial or yeast inoculum is approximately $10^2$–$10^3$ CFU/well. The percentage growth of the bacteria or yeast in test wells relative to that observed for a control well containing no compound is determined by measuring absorbance at 595 nm ($A_{595}$) after 20–24 hours at 37° C. (bacteria) or 40–48 hours (yeast) at 25° C. The MIC is determined as a range of concentration where complete inhibition of growth is observed at the higher concentration and bacterial/yeast cells are viable at the lower concentration. Ampicillin and tetracycline are used as antibiotic positive controls for bacterial MIC assays. Amphotericin B is used as a positive control for yeast MIC assay.

Example 11

Preparation of 5,6-dichloro-2-piperidin-4-yl Benzimidazole Derivatives

Using the procedures described above, the following 5,6-dichloro-2-piperidin-4-yl benzimidazole derivatives prepared according to Scheme 11 as described below:

Scheme 11

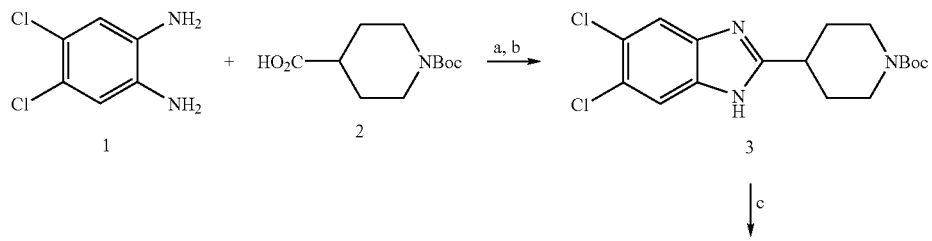

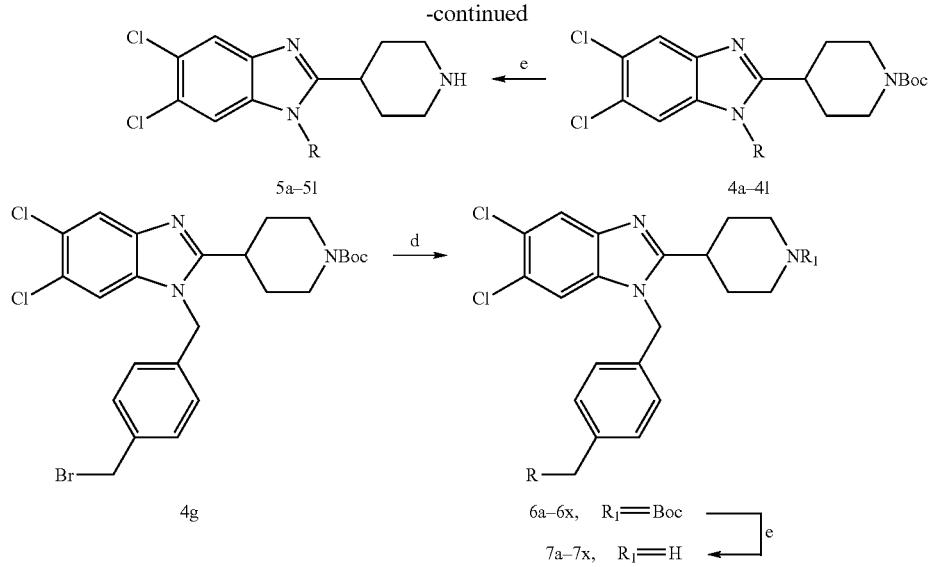

Treatment of commercially available 4,5,-dichloro-1,2-phenylenediamine(1) and N-Boc-isonipecotic acid (2) with EDC in the presence of catalytic amount of DMAP led to the formation of the corresponding amide. The crude mixture was then refluxed in aqueous sodium hydroxide solution to give cyclized itermediate 3, which was reacted with various alkyl, benzyl and aryl halides to give 4a–4l. Treatment of compound 4g with various amines or nitrogen-containing heterocykles provided 6a–x. Deprotection of the Boc group with anhydrous hydrogen chloride (HCL, 4.0 M) in dioxane at room temperature for 30 minutes to form benzimidazoles 5a–i.

This procedure was employed to prepare the following compounds:

| | |
|---|---|
| R═H | 5a |
| R═Et | 5b |
| R═4-PyCH2 | 5c |
| R═3-PyCH2 | 5d |
| R═4-F-Bn | 5e |
| R═4-NO2-Bn | 5f |
| R═4-(BrCH2)Bn | 5g |
| R═2-Pyrimidine | 5h |
| R═2,4-(NO2)2Ph | 5i |

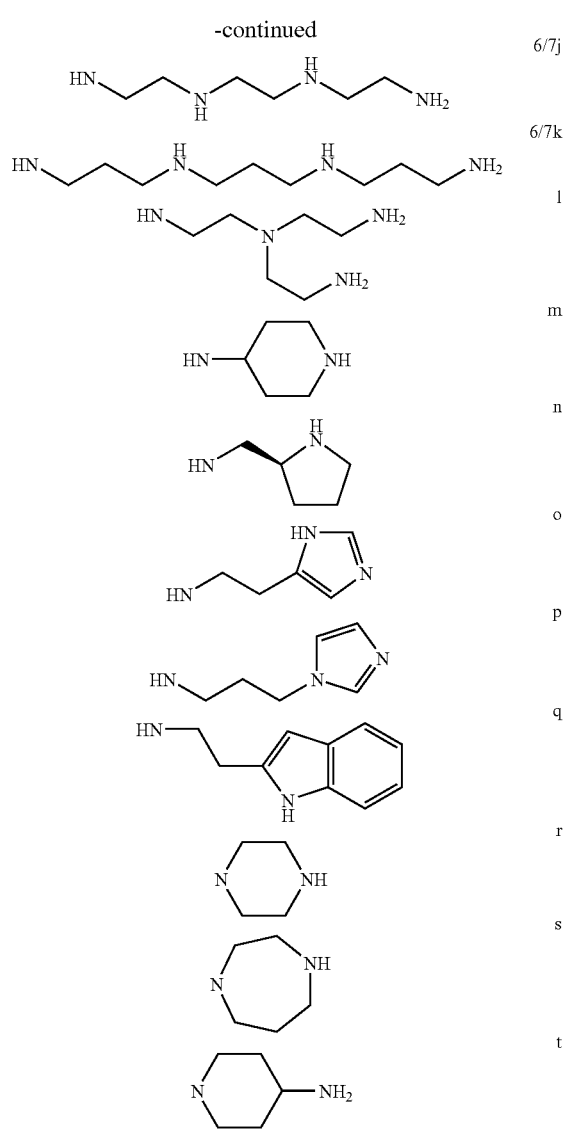

-continued

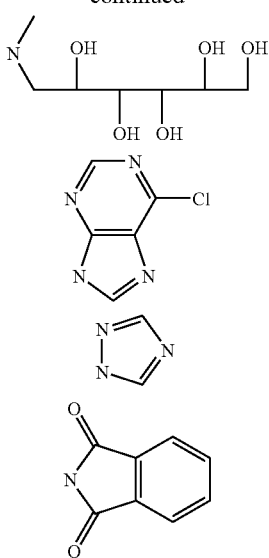

u v w x

These compounds were evaluated for their ability to inhibit *S. aureus* and *E. coli* growth and Bacterial Transcription/Translation according to the procedures described herein. In addition, all benzimidazoles were also screened for their ability to inhibit bacterial translation and transcription using a combined assay. Several compounds (7c, 7d, 7j–l, 10a–b) were found to posses low micromolar IC50. Since most of the IC50 value are much higher than the corresponding MICs for *S. aeures* and *E. coli.*, it's unlikely that the antibacterial activities are the direct results of bacterial transcription/translation inhibition. However they could be a result from the combination of multiple mechanismns of actions including transcription/translation inhibition. The results are presented in Table 1 below:

TABLE 1

Inhibitory Effects of Benzimidazoles on *S. aureus* and *E. coli* Growth and Bacterial Transcription/Translation.

| Compounds | S. aureus MIC (μM) | E. coli MIC (μM) | T/T IC50 MIC (μM) |
| --- | --- | --- | --- |
| (5a) | >100 | >100 | >100 |
| (5b) | >100 | >100 | >100 |

TABLE 1-continued

Inhibitory Effects of Benzimidazoles on *S. aureus* and *E. coli* Growth and Bacterial Transcription/Translation.

| Compounds | S. aureus MIC (μM) | E. coli MIC (μM) | T/T IC50 MIC (μM) |
| --- | --- | --- | --- |
| (5c) | 75.00 | 94 | >100 |
| (5d) | 75.00 | 86 | >100 |
| (5e) | >100 | >100 | >100 |
| (5f) | >100 | >100 | >100 |
| (4g) | 52.00 | >100 | >100 |
| (5h) | >100 | >100 | >100 |
| (5i) | >100 | >100 | >100 |
| (7a) | 6–12 | 12–25 | 100 |
| (7b) | 3–6 | 6–12 | >100 |
| (7c) | 6–12 | 12–25 | 12 |
| (7d) | 12–25 | 50–100 | 20 |
| (7e) | 6–12 | 25–50 | 50 |
| (7f) | 12–25 | 25–50 | >100 |
| (7g) | 6–12 | 12–25 | 100 |
| (7h) | 12–25 | 50–100 | >100 |
| (7i) | 6–12 | 6–12 | >100 |
| (7j) | 6–12 | 50–100 | 10 |
| (7k) | 3–6 | 25–50 | 10 |
| (7l) | 3–6 | 12–25 | 10 |
| (7m) | 6–12 | 12–25 | >100 |
| (7n) | 12–25 | 12–25 | >100 |
| (7o) | 6–12 | 12–25 | 25 |
| (7p) | 12–25 | 12–25 | >100 |
| (7q) | — | — | — |
| (7r) | 6–12 | 12–25 | >100 |
| (7s) | 6–12 | 12–25 | >100 |
| (7t) | 6–12 | 50–100 | 60 |
| (7u) | 6–12 | 25–50 | >100 |
| (7v) | >100 | >100 | 12–25 |
| (7w) | 12–25 | 12–25 | >100 |
| (7x) | 6–12 | 6–12 | >100 |
| (10a) | 25–50 | 25–50 | 25 |
| (10b) | 12–25 | 12–25 | 35 |
| (10c) | 6–12 | 12–25 | >100 |
| (12) | 3–6 | 6–12 | >100 |

Example 12

Preparation of Benzimidazole Dimers

Several benzimidazole dimers were prepared according to the procedures of Schemes 12 and 13, below, and evaluated for their antibacterial activity.

Scheme 12

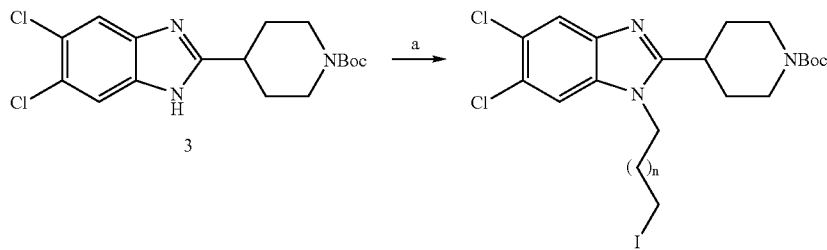

8a: n=1, 54%
8b: n=3, 66%
8c: n=4, 70%

↓b

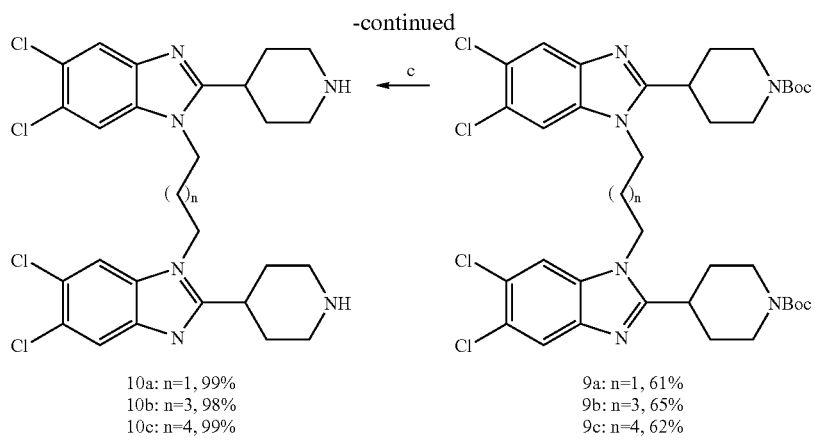

10a: n=1, 99%
10b: n=3, 98%
10c: n=4, 99%

9a: n=1, 61%
9b: n=3, 65%
9c: n=4, 62%

Synthesis of Benzimidazole Dimers 10a–c

Reagents and conditions: a) NaH, DMF, 0° C., 2 h, 1,3-diiodopropane, 8a, 54%; 1,5-diodopentane, 8b, 66%; 1,6-diodohexane, 8c, 70%; (b) 3, NaH, DMF, 0° C., 2 h, 61% for 9a, 65% for 9b, 62% for 9c; (c) 6 MHCl/dioxane, 25° C., 2 h.

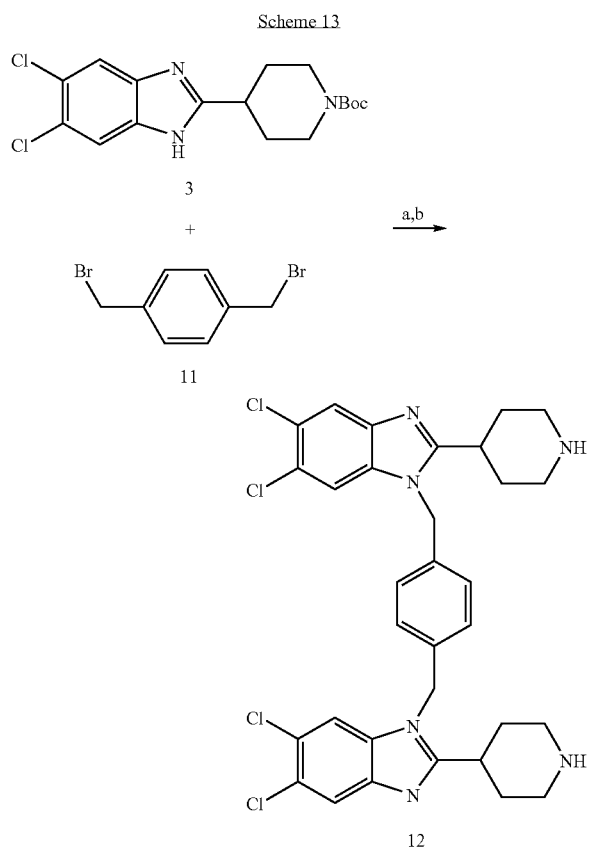

Synthesis of Benzimidazole Dimer 12

Reagents and conditions: a) 0.5 equiv. α,α-dibromo-p-xylene, NaH, DMF, 0° C., 2 h, 56%; (b) 4 M HCl/dioxane, RT, 2 h, 98%.

Mono alkylation of benzimidazole with diiodo alkanes provided intermediates 8a–c, which were then reacted again with 3 to provide the corresponding dimers 9a–c. The Boc protecting groups were cleanly removed using hydrogen chloride in dioxane to give the final dimer analogs 10a, 10b and 10c in almost quantitative yield (Scheme 12). The xylene-spaced dimer 12 was prepared from intermediate 3 by first reactirig 0.5 equivalents of α,α-dibromo-p-xylene (11), followed by deprotection using hydrogen chloride (Scheme 13).

The inhibitory effects of benzimidazole dimers on S. aureus and E. coli growth and bacterial transcription/translation are shown in Table 2 below.

TABLE 2

Inhibitory Effects of Benzimidazole Dimers on S. aureus and E. coli Growth and Bacterial Transcription/Translation.

| Compounds | S. aureus MIC (μM) | E. coli MIC (μM) | T/T IC50 MIC (μM) |
| --- | --- | --- | --- |
| (10a) | 25–50 | 25–50 | 25 |
| (10b) | 12–25 | 12–25 | 35 |
| (10c) | 6–12 | 12–25 | >100 |
| (12) | 3–6 | 6–12 | >100 |

To test effectiveness of benzimidazoles of Examples 11 and 12 against other bacteria, the active compounds from the preliminary screening were screened against additional four strains of Gram positive and four strains of gram negative bacteria, and the results are shown in FIG. 1. These compounds exhibited higher potencies against Gram position bacteria (S. aureus 13709, E. hirae 29121, S pyogenes 49399, and S. pneumoniae 6303) as compared to Gram-negative bacteria (E. coli 25922, P. vulgaris 8427, K. pneumoniae 1338, P. aeruginosa 25416). Several benzimidazoles (7b, 7g–k, 12) showed particularly strong activity against E. hirae. To study the selectivity, these compounds were also screened against yeast cell line C. albicans 10231. These compounds are clearly much less effective as compared to their inhibition of bacterial growth.

Since entercocccus infection is upcoming, and presents a major threat to the human health, compounds were screened against seven additional clinically important strains of entercocccus and the results are shown in FIG. 2. As mentioned previously, all these selected compounds are very effective against E. Hirae_ATCC_29212 and less potent against other strains with some exceptions that six of them (7a, 7b, 7x, 10b, 10c, 12) exhibited strong inhibitory activities against all eight strains.

Example 13

Preparation of Alkyl Spaced Benzimidazole Derivatives

Several alkyl spaced benzimidazole derivatives were prepared according to the procedures of Scheme 14, below:

Alkyl Spaced Benzimidazole Derivatives

Reagents and conditions: a) EDC, DMAP; b). NaOH, H$_2$O, 65% over 2 steps; c) ICH$_n$(CH$_n$)$_n$CH$_n$I, NaH or K$_2$CO$_3$; d) ArH, NaH or K$_2$CO$_3$; e) 4.0 M HCl/dioxane, CH$_2$Cl$_2$, 25° C., 0.5 h, >95%.

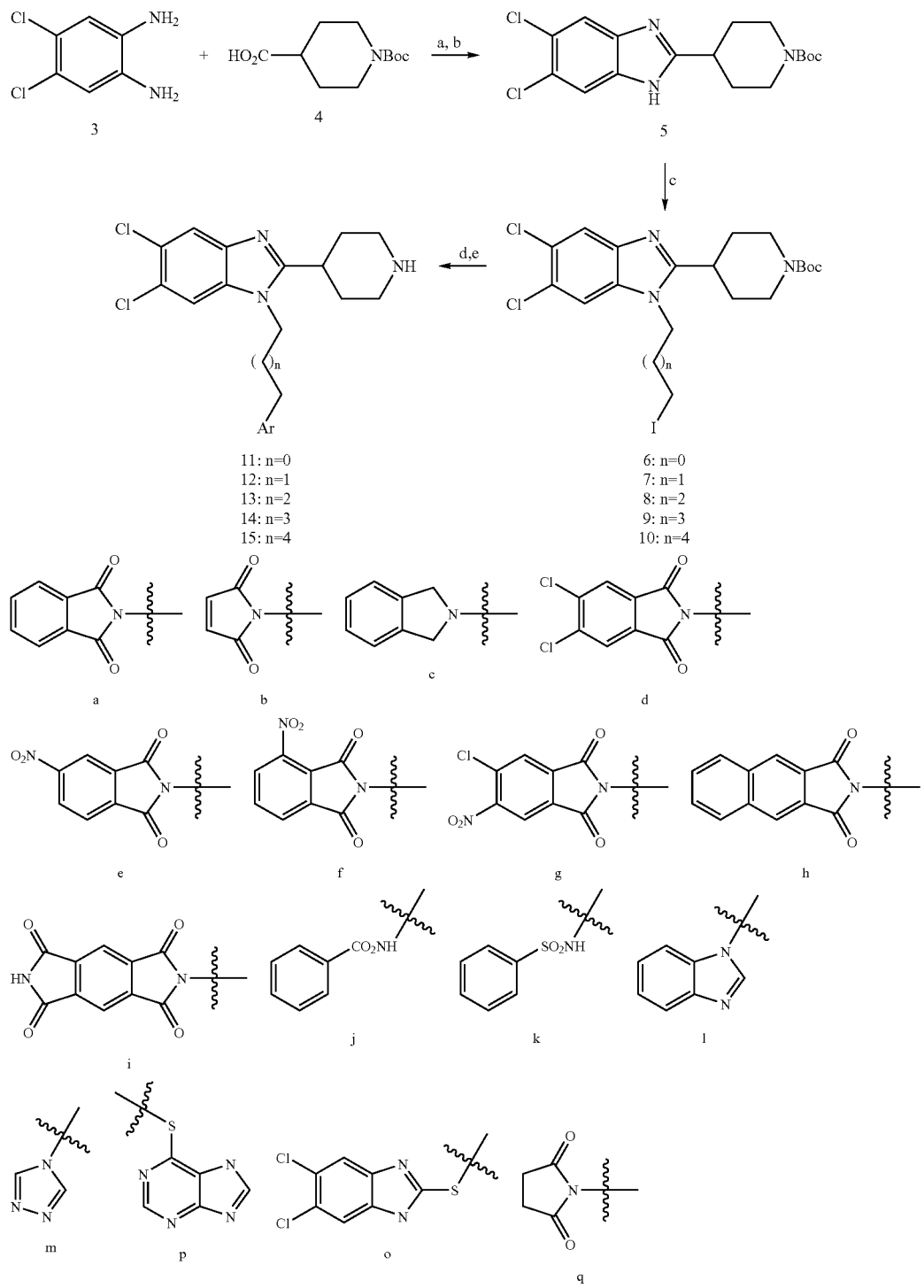

4,5-dichloro-1,2-dianiline (1) reacted smoothly with N-Boc-isonipecotic acid to give the corresponding amide, which cyclized upon treatment with sodium hydroxide to give benzimidazole 5. Reaction of 5 with different diiodides funished 6–10 in good yields. A variety of nitrogen-containing heterocylces were then introduced by simple alkylation to give the target molecules 11–15.

Example 14

Preparation of Hydrazone Benzimidazole Derivatives

Several hydrazone benzimidazole derivatives were prepared according to the procedures of Scheme 15 below:

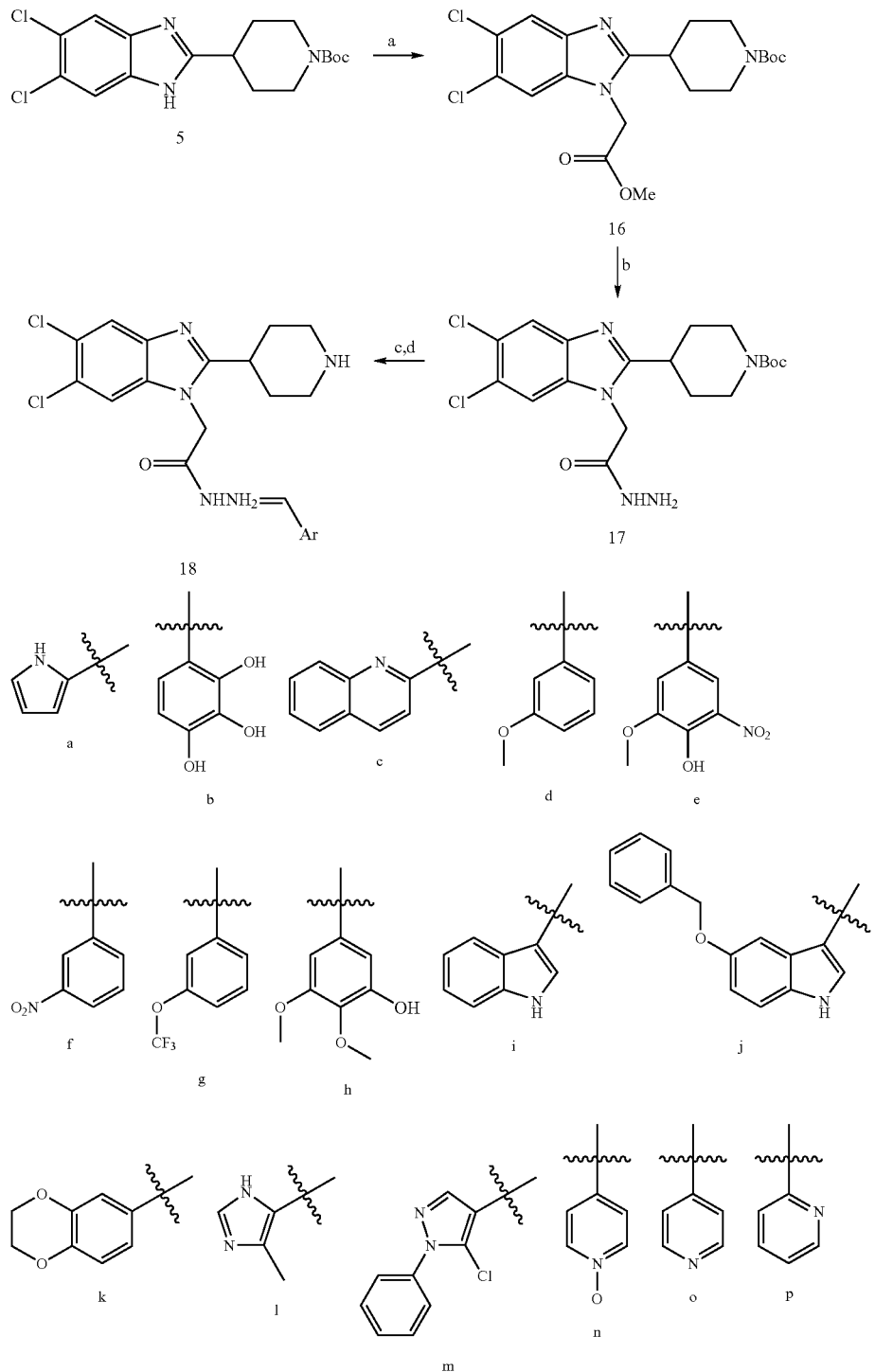

Preparation of Hydrazone Benzimidazole Derivatives

Reagents and conditions: a). NaH (3.0 equiv), BrCH$_2$CO$_2$Me (1.2 equiv), DMF, 25° C., 0.5 h, 92%; B). H$_2$NNH$_2$ (5.0 equiv), DMF, 25° C., 2.0 h, 98%; c). ArCHO (1.02 equiv.), CH$_2$Cl$_2$, 25° C., 0.5 h, >95%; d). 4.0 M HCl/dioxane, CH$_2$Cl$_2$, 25° C., 0.5 h, >95%.

Acylhydrazide 17 was synthesized as a key intermediate for the combinatorial generation of benzimidazoles. Since the acyl hydrazide could serve as both a hydrogen donor and acceptor to add additional contacts with the target, analogs based on 17 could be potentially more potent than the parent benzimidazoles. Acycl hydrazide 17 was easily prepared from 3 in gram quantity in excellent overall yield from 5 by alklylation with methyl α-bromoacetate followed by a nucleophilic displacement of the methoxy group. Many derivatives could be easily synthesized form 17 without the need of vigorous purification. The first series of analogs has the general structure 18 and was prepared by simply reacting 17 with different aldehydes followed by the removal of the Boc protecting group with hydrogen chloride. All the benzimidazole analogs obtained this way have more than 95% purity based on TLC and LC/MS analysis and were used directly for our MS-based screening and antibacterial assays.

Example 15

Preparation of Hydrazine Benzimidazole Derivatives

Several hydrazine benzimidazole derivatives were prepared according to the procedures of Scheme 16 below:

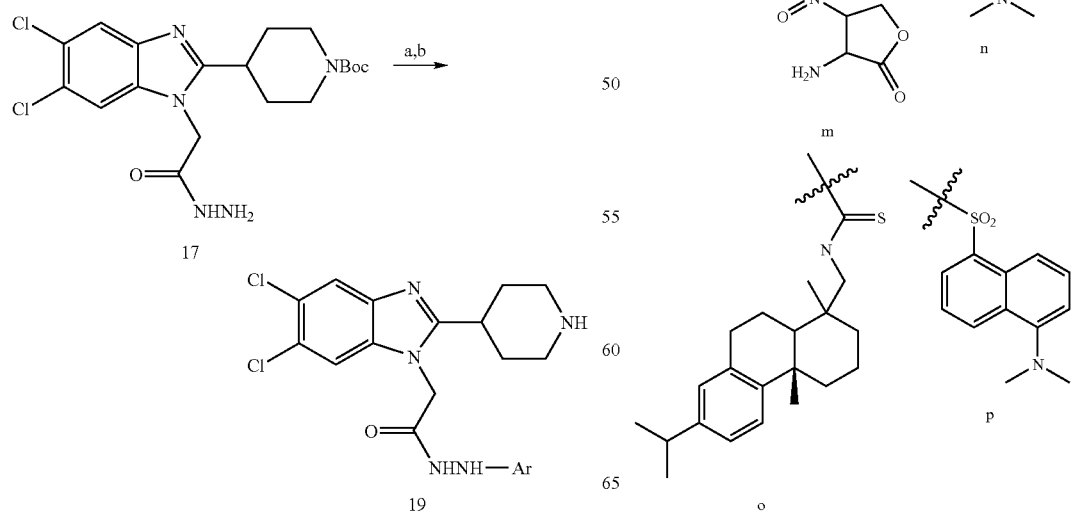

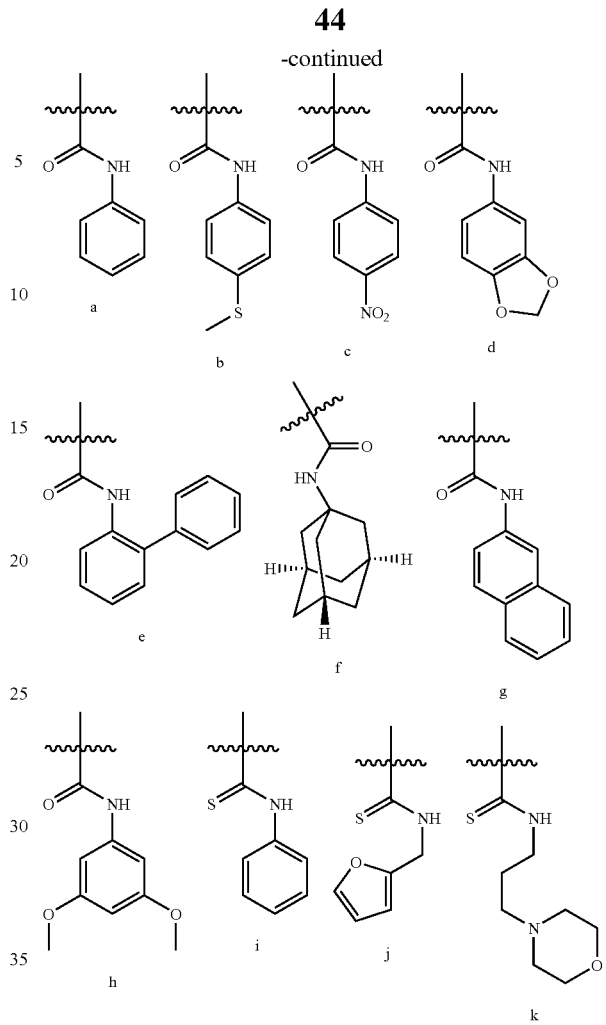

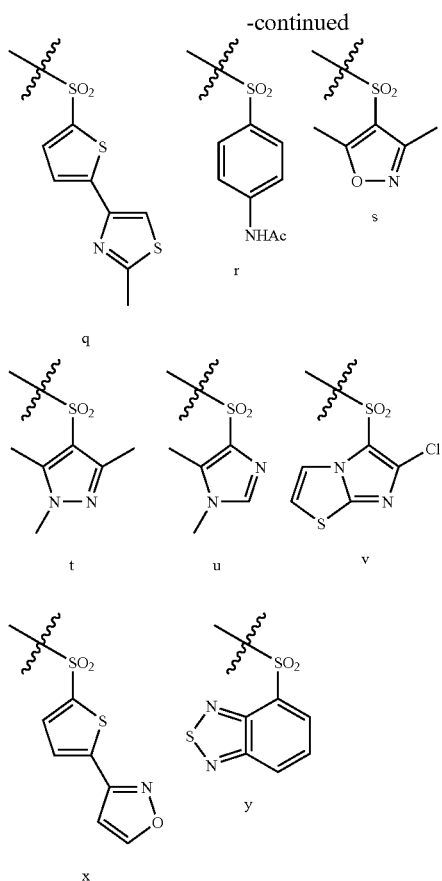

Hydrazine Benzimidazole Derivatives

Synthesis of Benzimidazoles 19a–19y. Reagents and conditions: a) For 19a–o, RNCO or RNCS (1.05 equiv), CH$_2$CH$_2$, 25° C., 0.5 h, >95%; for 19p–y, RSO$_2$Cl (1.05 equiv), Et$_3$N (1.5 equiv), DMAP (cat.), >95%; b) 4.0 M HCl/dioxane, CH$_2$Cl$_2$, 25° C., 0.5 h, >95%.

A variety of isocynates, isothiocyanates and sulfonyl chlorides were reacted with acyl hydrazide 17, and the corresponding ureas, thioureas and sulfonates were obtained in excellent yields and purity as shown in Scheme 16. The resulting N-Boc protected intermediates were treated with hydrogen chloride to give the corresponding products of general structure 19 in almost quantitative yields and more than 95% purity. These products were used directly for antibacterial assays.

Example 16

Inhibitory Effects of Benzimidazoles on *S. aureus* and *E. coli* Growth and Bacterial Transcription/Translation For Compounds of Examples 13–15

Table 3 shows the in vitro antibacterial activity (referred to as MIC, the minimum concentration inhibiting fungal cell growth) of the benzimidazoles against *S. aureus* and *E. coli*. FIG. 3 shows the in vitro inhibitorial activity of selected benzimidazoles against additional pathogenic strains of bacteria (four Gramn positive strains, four gram negative strains and one yeast strain). The assays are carried out in 150 μL volume in duplicate in 96-well clear flat-bottom plates. The bacterial or yeast suspension from an overnight culture growth in appropriate medium is added to a solution of test compound in 2.5% DMSO in water. Final bacterial or yeast inoculum is approximately 10$^2$–10$^3$ CFU/well. The percentage growth of the bacteria or yeast in test wells relative to that observed for a control well containing no compound is determined by measuring absorbance at 595 nm (A$_{595}$) after 20–24 hours at 37° C. (bacteria) or 40–48 hours (yeast) at 25° C. The MIC is determined as a range of concentration where complete inhibition of growth is observed at the higher concentration and bacterial/yeast cells are viable at the lower concentration. Ampicillin and tetracycline are used as antibiotic positive controls for bacterial MIC assays. Amphotericin B is used as a positive control for yeast MIC assay,

TABLE 3

Inhibitory Effects of Benzimidazoles on *S. aureus* and *E. coli* Growth and Bacterial Transcription Translation.

| Compound | *S. aureus* MIC (mM) | *E. coli* MIC (mM) |
|---|---|---|
| 6 | >100 | >100 |
| 11 | >100 | >100 |
| 12 | >100 | >100 |
| 13a | >100 | >100 |
| 13o | >100 | >100 |
| 13p | >100 | >100 |
| 14a | 12–50 | 25–50 |
| 14b | 6–12 | >100 |
| 14c | 50–100 | 25–50 |
| 14d | 12–25 | 50–100 |
| 14e | >100 | 50–100 |
| 14f | >100 | >100 |
| 14g | 25–50 | 50–100 |
| 14h | >100 | >100 |
| 14i | >100 | >100 |
| 14j | >100 | >100 |
| 14k | >100 | >100 |
| 14l | >100 | >100 |
| 14l | 50–100 | 50–100 |
| 14q | >100 | >100 |
| 15a | >100 | >100 |
| 18a | 12–25 | >100 |
| 18b | 12–25 | >100 |
| 18c | 25–50 | >100 |
| 18d | 25–50 | >100 |
| 18e | 25–50 | >100 |
| 18f | 25–50 | >100 |
| 18h | 25–50 | >100 |
| 18i | 25–50 | >100 |
| 18j | 3–6 | >100 |
| 18k | 50–100 | >100 |
| 18l | 50–100 | >100 |
| 18m | 6–12 | >100 |
| 18n | >100 | >100 |
| 18o | >100 | >100 |
| 18p | >100 | >100 |
| 18q | 25–50 | >100 |
| 19b | 12–25 | 25–50 |
| 19c | 25–50 | >100 |
| 19c | 12–25 | 25–50 |
| 19d | 25–50 | 50–100 |
| 19e | 50–100 | >100 |
| 19f | 6–12 | 12–25 |
| 19g | 6–12 | 12–25 |
| 19h | 6–12 | 25–50 |
| 19h | 50–100 | >100 |
| 19i | 25–50 | 50–100 |
| 19j | 50–100 | >100 |
| 19k | >100 | >100 |
| 19l | >100 | >100 |
| 19m | >100 | >100 |
| 19o | 25–50 | 25–50 |
| 19p | 12–25 | >100 |
| 19q | 50–100 | >100 |
| 19r | >100 | >100 |
| 19s | >100 | >100 |
| 19t | >100 | >100 |
| 19u | >100 | >100 |
| 19v | >100 | >100 |
| 19w | >100 | >100 |
| 19x | >100 | >100 |
| 19y | >100 | >100 |

Example 17

Synthesis of Piperidine Modified Benzimidazoles and Their Binding Affinities For *E. coli* 16S A-site It has been established that the 16S A-site is involved in bacterial translation, and the aminoglycosides are known to bind to the region. Thus, the bacterial 16S A-site represents a prime target for discovering antibacterial agents, and much work has focused on the modification of the natural aminoglycosides. In accordance with the present invention, several small molecules were synthesized that were shown to bind to the 16S A-site of *E. coli* ribosome RNA. These are shown below in Scheme 17.

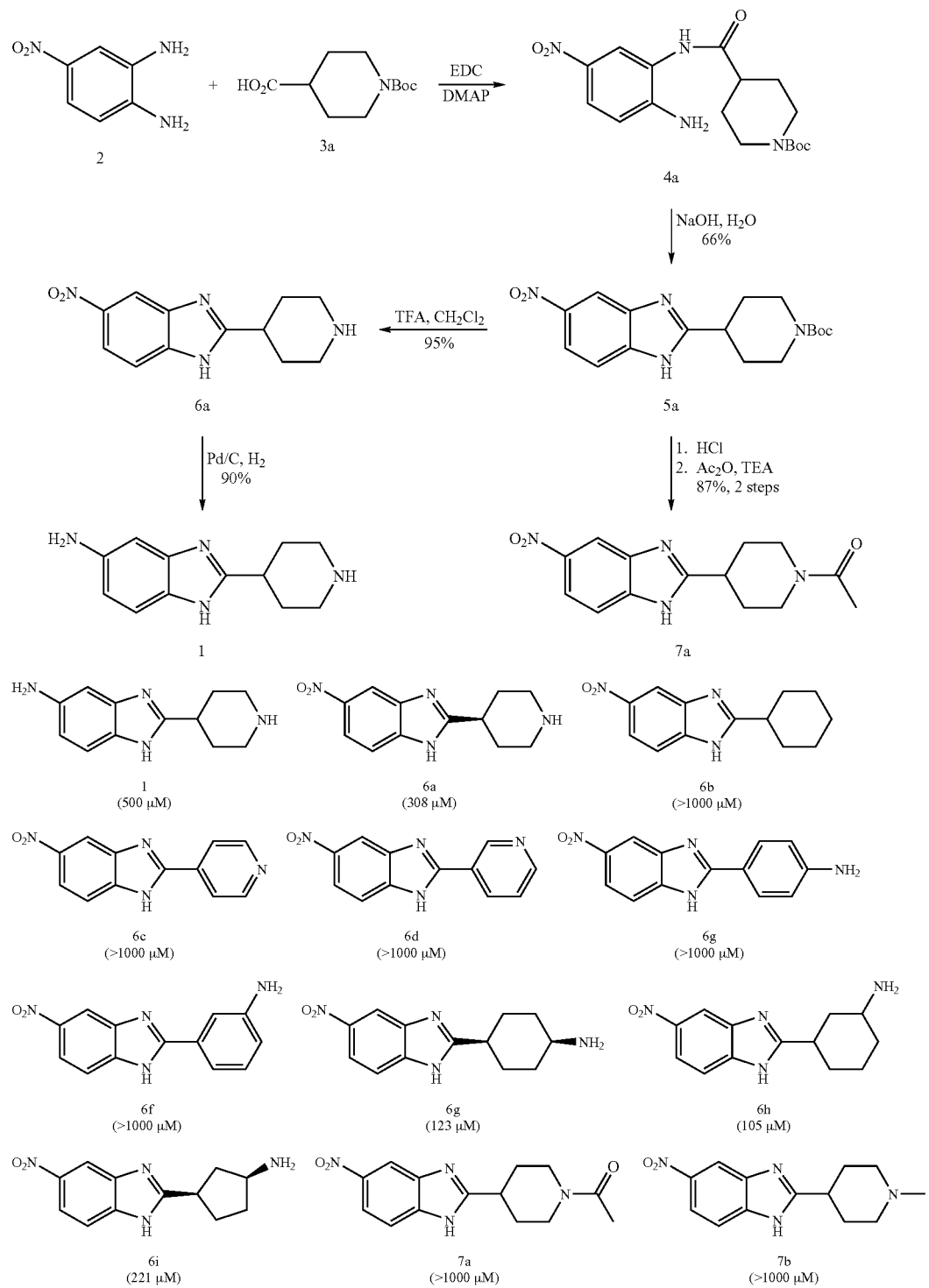

Synthesis of Piperidine-modified Benzimidazoles and Their Binding Affinities for *E. coli* 16S A-site MS-based competition experiments were used to determine the binding location of 1 to the target RNA. Glucosamine is the A-ring of paromomycin that is known to bind to the target RNA and inhibits bacterial translation. Data suggest that 1 and glucosamine compete for the same binding site on the target RNA. Since glucosamine binds to the target RNA at the same location as it is in paromomycin binding, while not wishing to be bound by any particular theory, it is believed the 1 binds to the desired RNA decoding region and could potentially inhibit bacterial translations.

After establishing the binding of 1 to the correct location on the target RNA, systematic chemical modifications were carried out to study the structure activity relationship (SAR) around the benzimidazole. The synthesis of compound 1 and piperidine-modified benzimidazoles are shown above in Scheme 17. Treatment of commercially available 5-nitro-1,2-dianiline (2) and N-Boc-isonipecotic acid (3) with EDC in the presence of catalytic amount of DMAP led to the formation of the corresponding amide as a mixture of two regioisomers (4a,b). The crude mixture was then refluxed in aqueous sodium hydroxide solution for ?? hours gave the cyclized intermediate 6a. Treatment of compound 5 with 20% TFA in dichloromethane at room temperature for 30 minutes led to the formation of compound 6, which was then hydrogenated over Pd/C to give 1. MS-based assay suggested that an electron withdrawing nitro group at C5 position (6) is preferred over the corresponding amino group (1), and almost doubled the binding affinity for the target 16S RNA A-site. Thus, in order to establish the SAR of the benzimidazoles, a series of piperidine-modified analogs with a nitro substitution at 5 position (6a–7b) were synthesized by following the same synthetic route and all these compounds were screened against 16S RNA A-site. A basic NH group with the correct orientation in this region is required to maintain the affinity, since acetylation (7a), methylation (7b), removal (6b) of the free NH group and unsaturation of the piperidine ring (6c) all diminished the binding affinity. The NH group is critical, presumably because it forms a hydrogen bond with the negatively charged phosphate in the RNA backbone. The extended piperidine analogs (6g–6t) showed improved affinities, which, while not wishing to be bound by any particular theory, are believed to better orient the NH groups to contact the phosphate backbone.

Example 18

One-Pot Synthesis of Benzimidazoles and Their Binding Affinities for *E. coli* 16S A-site A series of piperidine substituted benzimidazoles were prepared according to the one-pot procedure of Scheme 18:

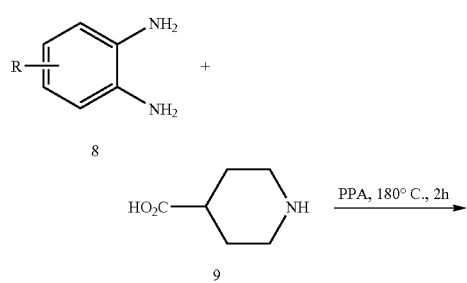

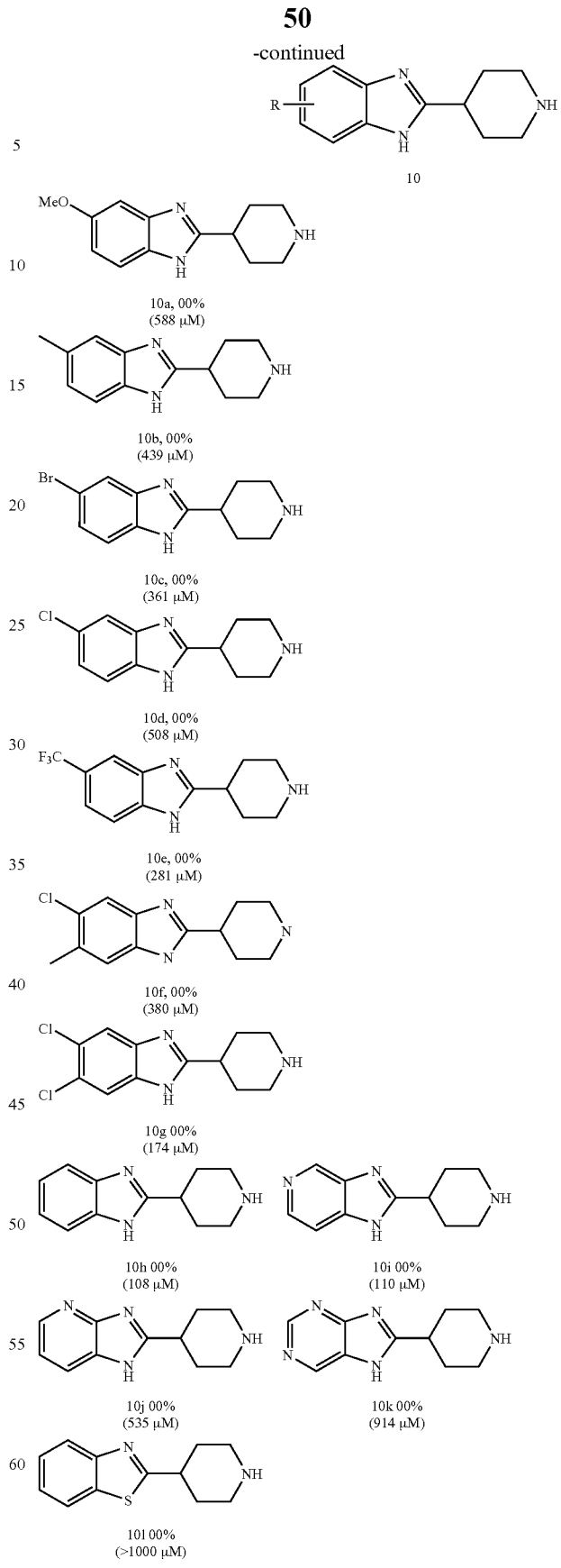

A series of benzimidazole-modified analogs were prepared as shown above. The procedure required the simple heating of a suitable 1,2-dianiline (8) with isonipecotic acid (9) in the presence of polyphosphoric acid. The free benzimidazoles were then isolated in good to excellent yields after basic work-up. From a MS-based assay, it was established that 1) An electron donating groups such as, $NH_2$ and OMe reduced the affinities (1, 10a); 2) Certain hydrophobic substitutions such as a methyl (10b), bromo (10c) and chloro (10d) are tolerated; 3) Insertion of nitrogen atoms into the aromatic moiety (10i–10k), particularly at the C4 position (10j) reduced activities; and 4) Electron-withdrawing groups enhanced the affinities (10e–10g).

Example 19

Synthesis of Additional N-1 Substituted Benzimidazoles and Their Binding Affinities for *E. coli* 16S A-site A further series of N-1 benzimidazole analogs were prepared according to Scheme 19 below:

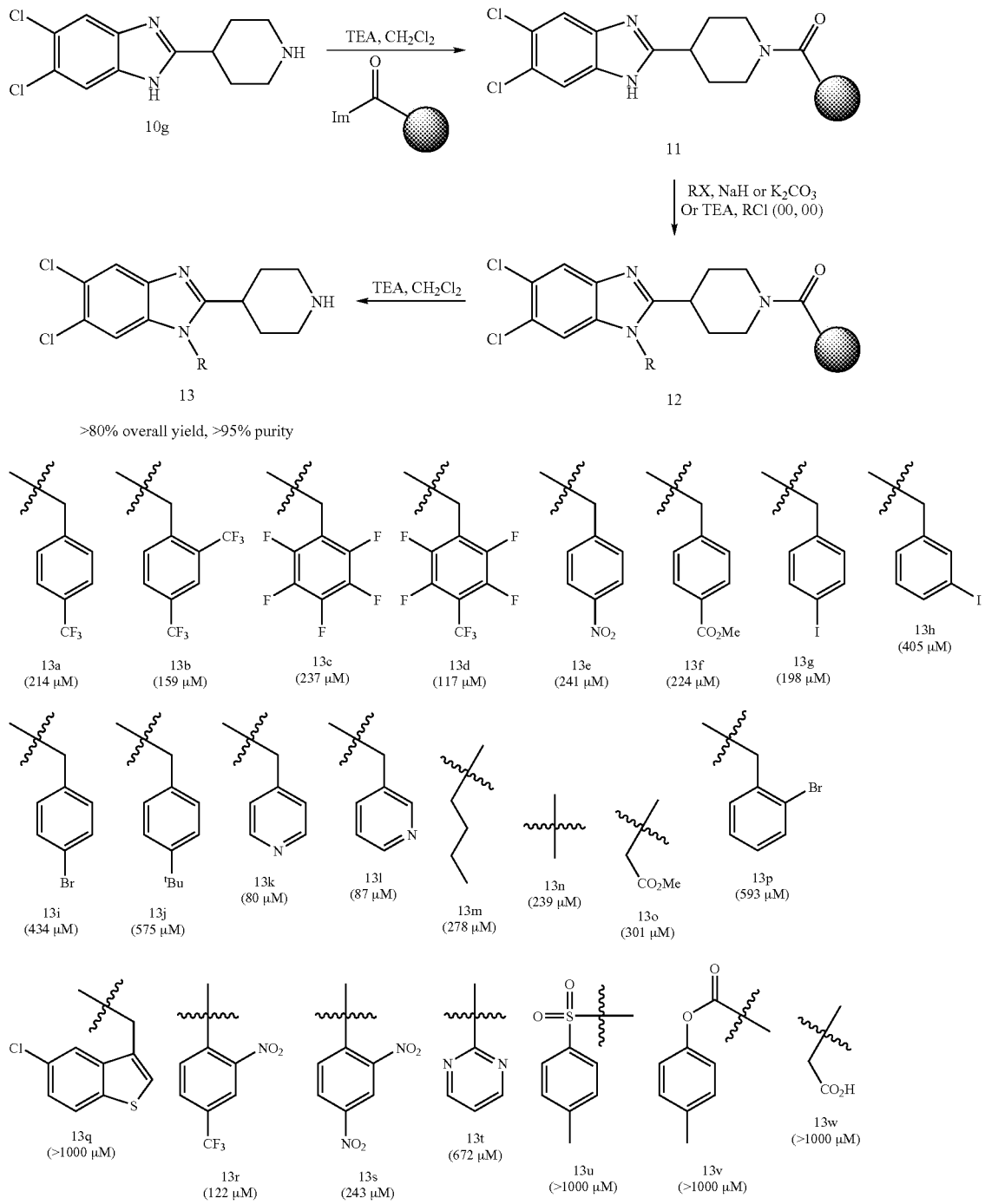

Solid-phase synthesis of N1 Substituted Benzimidazoles and Their Binding Affinities for *E. coli* 16S A-site This series of compounds were efficiently synthesized by employing the solid-phase chemistry shown in Scheme 19. Wang resin was first converted into imidazole carbonyl derivative, which was then allowed to react with compound 10g to give common intermediate 32. Compound 11 reacted readily with a variety of alkylating or acylating reagents to give the corresponding alkyl or acyl products, which after removal of Boc group with 50% TFA in dichloromethane led to the desired N-1 substituted analogs in excellent yields and purity.

Example 20

Synthesis of Additional Benzimidazole Dimers and MIC and Their Transcription/Translation Activity This series of assays is known to those of skill in the art, and other assays may be substituted therefore without deviating from the spirit and scope hereof. The DNA template, pBestLuc™ (Promega), is a plasmid containing a reporter gene for firefly luciferase fused to a strong tac promoter and ribosome binding site. Messenger RNA from 1 µg pBestLuc is transcribed and translated in *E. coli* S30 bacterial extract in the presence or absence of test compound. Compounds are tested in a black 96 well microtiter plate with an assay volume of 35 µL. Each test well contains: 5 µL test compound, 13 µL S30 premix (Promega), 4 µL 10× complete amino acid mix (1 mM each), 5 µL *E. coli* S30 extract and 8 µL of 0.125 µg/µL pBestLuc™. The transcription/translation reaction is incubated for 35 minutes at 37° C. followed by detection of functional luciferase with the addition of 30 µL LucLite™ (Packard). Light output is quantitated on a Packard TopCount.

The assays are carried out in 150 µL volume in duplicate in 96-well clear flat-bottom bottom plates. The bacterial suspension from an overnight culture growth in appropriate medium is added to a solution of test compound in 4% DMSO in water. Final bacterial inoculum is approximately $10^5$–$10^6$ CFU/well. The percent growth of the bacteria in test wells relative to that observed for a well containing no compound is determined by measuring absorbance at 595 nm ($A_{595}$) after 24 h. The MIC is determined as a range of single compound where the complete inhibition of growth is observed at the higher concentration and cells are viable at the lower concentrations. Both ampicillin and tetracycline are used as antibiotic-positive controls in each screening assay for *S. pyogenes, E. coli, S. aureus, E. faecalis, K. pneumoniae* and *P. vulgaris*; . Ciprofloxacin is used as an antibiotic positive control in each screening assay for *P. aeruginosa*.

Biological activity of selected compounds according to the present invention were assayed according to techniques known in the art.

A series of 2-aminobenzimidazole dimers were synthesized according to the procedure described in Example 11. A series of 5- and 6-substituted-2-aminobenzimidazoles also were synthesized, and all were evaluated for biological activity. Tables 4–7 report MIC and transcription/translation activity for the dimer compounds By the outlined procedure. Tables 8 and 9 report the MASS screening of 2-aminobenzimidazoles against the AgIIa HCV-IRES target. The reported selectivity was determined by mass spectral analysis of any associations and provides information about the relative binding affinities.

TABLE 4

| Structure | MIC, *E. coli* (µM) | MIC, *S. aureus* (µM) | Transcription/ Translation, IC$_{50}$ (µM) |
|---|---|---|---|
| 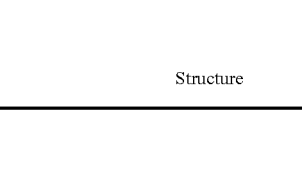 | 12–25 | 12–25 | >100 |

TABLE 4-continued

| Structure | MIC, E. coli (μM) | MIC, S. aureus (μM) | Transcription/ Translation, IC$_{50}$ (μM) |
|---|---|---|---|
| (bis-benzimidazole structure with 2-amino groups) | 25–50 | 75–100 | 25 |
| (bis-benzimidazole structure with Br substituents and 2-amino groups) | 25–50 | 25–50 | >100 |
| (bis-benzimidazole structure with methyl substituents and 2-amino groups) | >100 | >100 | 6–12 |

TABLE 4-continued
| Structure | MIC, E. coli (μM) | MIC, S. aureus (μM) | Transcription/ Translation, IC$_{50}$ (μM) |
| --- | --- | --- | --- |
| 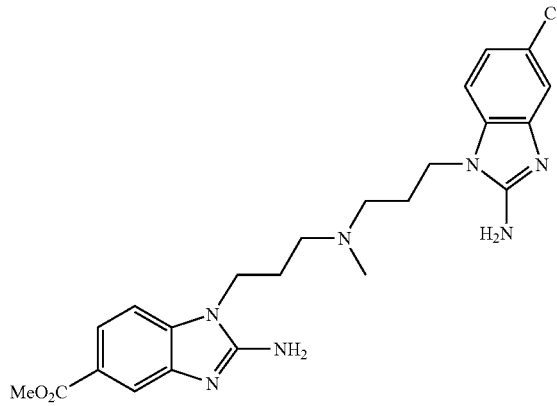 | >200 | >200 | >100 |
| 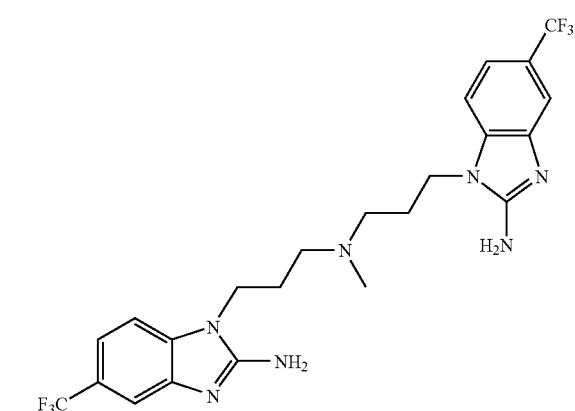 | 25–50 | 50–100 | >100 |
| 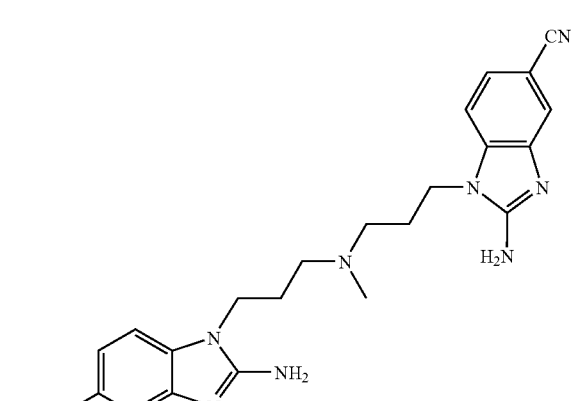 | >200 | >200 | >200 |
| 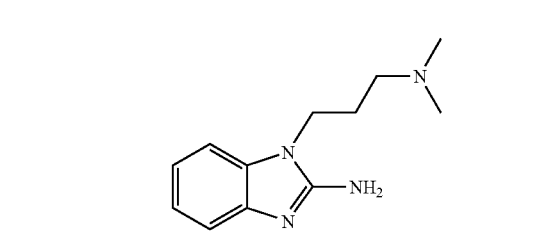 | >50 | >50 | >100 |

TABLE 5

[Structure image]

| Structure | MIC, E. coli (µM) | MIC, S. aureus (µM) | Transcription/ Translation, IC$_{50}$ (µM) |
|---|---|---|---|
| X = N(CH$_3$)$_2$ | 50–75 | 25–50 | 20 |
| X = CH$_2$ | >100 | >100 | >100 |
| X = O | >100 | >100 | >100 |

TABLE 6

[Structure image]

| Structure | MIC, E. coli (µM) | MIC, S. aureus (µM) | Transcription/ Translation, IC$_{50}$ (µM) |
|---|---|---|---|
| X = N—Me | 25–50 | 75–100 | 25 |
| X = CH$_2$ | >100 | >100 | >100 |
| X = O | 6–12 | >100 | >100 |

TABLE 7

[Structure image]

| Structure | MIC, E. coli (µM) | MIC, S. aureus (µM) | Transcription/ Translation, IC$_{50}$ (µM) |
|---|---|---|---|
| X = H | >100 | >100 | >100 |
| X = Cl | >100 | >100 | >100 |

TABLE 8

MASS Screening of 6-Substituted-2-aminobenzimidazoles against Ag IIa HCV IRES Target

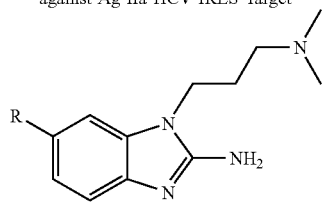

| R | Target conc. (µM) | Ligand conc. (µM) | % Complex | % Dimer | Selectivity |
|---|---|---|---|---|---|
| H | 2.5 | 50 | 125 | 35 | 4.30 |
| H | 2.5 | 7.5 | 33 | 3 | 7.49 |
| CH$_3$ | 2.5 | 50 | 136 | 31 | 6.55 |
| CH$_3$ | 2.5 | 7.5 | 26 | 0 | 8.44 |
| OCH$_3$ | 2.5 | 50 | 286 | 39 | 10.67 |
| OCH$_3$ | 2.5 | 7.5 | 52 | 4 | 12.89 |
| O(CH$_2$)$_3$N(CH$_3$)$_2$ | 2.5 | 50 | 862 | 72 | 96.88 |
| O(CH$_2$)$_3$N(CH$_3$)$_2$ | 2.5 | 7.5 | 46 | 0 | 34.53 |

TABLE 9

MASS screening of 5-substituted-2-aminobenzimidazoles against Ag IIa HCV IRES Target

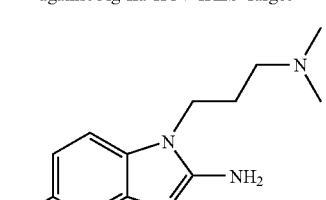

| R | Target conc. (µM) | Ligand conc. (µM) | % Complex | % Dimer | Selectivity |
|---|---|---|---|---|---|
| H | 2.5 | 50 | 125 | 35 | 4.30 |
| H | 2.5 | 7.5 | 33 | 3 | 7.49 |
| CH$_2$NH$_2$ | 2.5 | 7.5 | 14.7 | 0 | 2.0 |
| CH$_2$NH$_2$ | 2.5 | 50 | 109 | 80 | 2.3 |

It is intended that each of the patents, applications, and printed publications including books mentioned in this patent document be hereby incorporated by reference in their entirety.

As those skilled in the art will appreciate, numerous changes and modifications may be made to the preferred embodiments of the invention without departing from the spirit of the invention. It is intended that all such variations fall within the scope of the invention.

What is claimed is:

1. A compound having the Formula I:

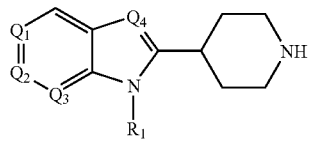

wherein:
$R_1$ is aryl, arylalkyl, heteroaryl, heteroarylalkyl, heterocycloalkyl, arylsulfonyl, aryloxycarbonyl, alkoxyalkoxyalkyl, alkyl-S—$R_7$, alkyl-NH—C(=O)—$R_8$ or —$R_9$—X—$R_{10}$-$R_{11}$)H;

wherein each of the alkyl, aryl, arylalkyl heteroaryl, heteroarylalkyl, heterocycloalkyl, arylsulfonyl, aryloxycarbonyl and alkoxyalkoxyalkyl moieties in each of the foregoing $R_1$ groups can be optionally substituted with up to 5 groups independently selected from the group consisting of $C_1$–$C_6$ alkyl, OH, hydroxyalkyl, —C(=O)—$R_5$; CN, aryl, alkoxycarbonyl, alkylaryl, arylalkyl, heteroaryl, S-heteroaryl optionally substituted with halogen, heteroarylalkyl optionally substituted with halogen, heterocycloalkyl optionally substituted with amino, $NO_2$, halogen, monohaloalkyl, dihaloalkyl, trihaloalkyl, perhaloaryl, perhaloalkylaryl, alkyl-$NR_{15}R_{16}$ and $NR_{15}R_{16}$;

or one of said alkyl, aryl, arylalkyl heteroaryl, heteroarylalkyl, heterocycloalkyl, arylsulfonyl, aryloxycarbonyl or alkoxyalkoxyalkyl moieties of one of said $R_1$ groups can be attached to a compound of Formula I at position $R_1$ thereof;

$R_3$ and $R_4$ are independently each halogen, $C_1$–$C_6$ alkyl, trihaloalkyl, alkoxycarbonyl, alkoxy, $NR_{15}R_{16}$, and $NO_2$, wherein said $C_1$–$C_6$ alkyl, alkoxycarbonyl, and alkoxy groups can each be optionally substituted with $NR_{15}R_{16}$;

$R_5$ is H, —NHNH$R_6$, —NHN=CH—$R_6$, heteroaryl, heterocycloalkyl, wherein said hereteroaryl group can be optionally substituted with an aryl or heteroaryl group, $R_6$ is aryl, heteroaryl; arylsulfonyl, heteroarylsulfonyl, —C(=S)—NH-aryl, —C(=S)—NH-arylcarbonyl, —C(=S)—NH-heteroarylcarbonyl, —C(=S)—NH-alkylene-$R_{21}$, —C(=O)—NHaryl, —C(=O)—NH-arylcarbonyl, —C(=O)—NH-heteroarylcarbonyl, or —C(=O)—NH-alkylene-$R_{21}$ where $R_{21}$ is carboxy, alkoxycarbonyl, aryl, heteroaryl, heterocycloalkyl, arylaminocarbonyl, cycloalkylaminocarbonyl, or a saturated hydrocarbon fused ring system optionally having an aryl ring fused thereto, said ring system being optionally substituted with up to three alkyl groups on the alkyl or aryl rings thereof;

wherein any of said $R_6$ groups can be optionally substituted with up to 3 groups selected from $NR_{15}R_{16}$, alkyl, hydroxy, halogen, aryl, alkoxy, trihaloalkoxy, arylalkyloxy, $NO_2$, —SH, —S-alkyl, heteroarylcarbonyl, heteroaryl, alkylheteroaryl, or a moiety of formula —OC$_2$CH$_2$—O— attached to adjacent atoms of said $R_6$ group;

$R_7$ is heteroaryl or heterocycloalkyl;

$R_8$ is aryl;

$R_9$ and $R_{10}$ are each independently alkylene having from 1 to about 20 carbons;

X is —N($R_{12}$)—, —C($R_{13}$)($R_{14}$)— or O;

$R_{11}$ is H, heteroaryl, or alkoxy, wherein said heteroaryl, or alkoxy group can be optionally substituted with up to four groups independently selected from halogen, amino, trihaloalkyl, alkoxycarbonyl, and CN;

$R_{12}$ is H or $C_1$–$C_6$ alkyl; and $R_{13}$ and $R_{14}$ are each independently H or $C_1$–$C_6$ alkyl, $R_{15}$ is H, halogen, $C_{1-12}$ alkyl, methylcarbonyl, heterocycloalkyl, arylsulfonyl, heteroarylalkyl, aminoalkyl, arylcarbonyl, branched and straight chain polyaminoalkyl, or a group of formula CH$_2$(CHOH)$_4$CH$_2$OH, wherein said methylcarbonyl, heterocycloalkyl, arylsulfonyl, heteroarylalkyl, aminoalkyl, arylcarbonyl, and branched and straight chain polyaminoalkyl groups can be substituted by up to 3 OH groups;

$R_{16}$ is H, halogen, or $C_1$–$C_6$ alkyl;

or $R_{15}$ and $R_{16}$ together with the nitrogen atom to which they are attached can form a succinimido or phthalimido group or a fused ring derivative thereof, wherein said succinimido or phthalimido group or fused ring derivative thereof can be optionally substituted by up to three substituents independently selected from $NO_2$ and halogen, or a group of Formula I at position $R_1$ thereof;

or $R_{15}$ and $R_{16}$ together with the nitrogen atom to which they are attached can form a group of Formula I wherein said nitrogen atom is Q4 thereof.

2. The compound of claim 1 wherein $R_3$ and $R_4$ are each independently halogen, amino, $NO_2$, CN, $C_{1-6}$ alkoxy or $C_{1-6}$ alkyl optionally substituted with up to 3 halogen atoms.

3. The compound of claim 1 wherein $R_3$ and $R_4$ are each independently halogen, amino, or $NO_2$.

4. The compound of claim 1 wherein $R_3$ and $R_4$ are each independently halogen.

5. The compound of claim 1 wherein $R_3$ and $R_4$ are each chlorine.

6. The compound of claim 1 wherein $R_1$ is alkyl substituted with alkoxycarbonyl, alkyl substituted with carboxy, or aralkyl where said aryl portion of said aralkyl is phenyl, pyridinyl, or pyrimidinyl, and where said phenyl, pyridinyl, or pyrimidinyl portion of said arylalkyl group is optionally substituted with up to 5 substituents selected from halogen, monohaloalkyl, dihaloalkyl, trihaloalkyl, $NO_2$, alkoxycarbonyl, and alkyl.

7. The compound of claim 5 wherein $R_1$ is alkyl substituted with alkoxycarbonyl, alkyl substituted with carboxy, or aralkyl where said aryl portion of said aralkyl is phenyl, pyridinyl, or pyrimidinyl, and where said phenyl, pyridinyl, or pyrimidinyl portion of said arylalkyl group is optionally substituted with up to 5 substituents selected from halogen, monohaloalkyl, dihaloalkyl, trihaloalkyl, $NO_2$, alkoxycarbonyl, and alkyl.

8. The compound of claim 6 wherein said phenyl, pyridinyl, or pyrimidinyl portion of said arylalkyl group is optionally substituted with up to 5 substituents selected from CF₃, F, Cl, NO₂, COOCH₃, I, Br, and t-butyl.

9. The compound of claim 7 wherein said phenyl, pyridinyl, or pyrimidinyl portion of said arylalkyl group is optionally substituted with up to 5 substituents selected from CF₃, F, Cl, NO₂, COOCH₃, I, Br, and t-butyl.

10. The compound of claim 1 wherein said R₁ is selected from the radicals consisting of:

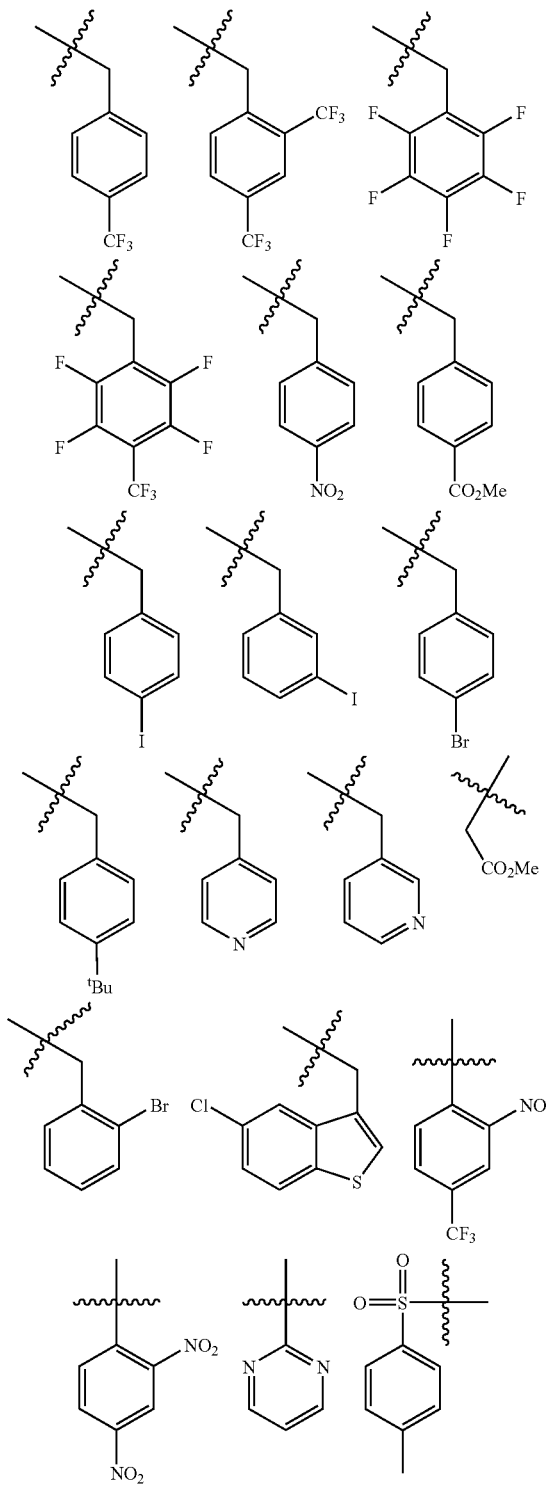

-continued

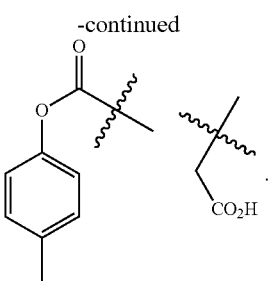

11. The compound of claim 1 wherein R₁ is alkyl substituted with —C(=O)—R₅.

12. The compound of claim 11 wherein R₅ is —NHNHR₆, or —NHN=CH—R₆.

13. The compound of claim 12 wherein R₅ is —NHNHR₆.

14. The compound of claim 12 wherein R₅ is —NHN=CH—R₆.

15. The compound of claim 13 wherein R₆ is —C(=O)—NH-aryl, —C(=O)—NHcycloalkyl, —C(=S)—NH-aryl, arylsulfonyl, heteroarylsulfonyl, heterocycloalkyl, arylaminocarbonyl, cycloalkylaminocarbonyl, —C(=S)—NH-alkylene-R₂₁ where R₂₁ is heteroaryl, or a saturated hydrocarbon fused ring system optionally having an aryl ring based thereto, said ring system being optionally substituted with up to three alkyl groups on the alkyl or aryl rings thereof, wherein any of said R₆ groups can be optionally substituted with up to 3 groups selected from NR₁₅R₁₆, NO₂, a moiety of formula —OC₂CH₂—O— attached to adjacent atoms of said R₆ group, aryl, C₁₋₆ alkoxy, carboxy, or C₁₋₆ trihaloalkoxy.

16. The compound of claim 14 wherein R₆ is aryl or heteroaryl optionally selected from up to 3 groups selected from OH, C₁₋₆ alkoxy, NO₂, C₁₋₆ trihaloalkoxy, C₁₋₆ trihaloalkyl, aryl, arylalkyloxy, and a moiety of formula —OC₂CH₂—O— attached to adjacent atoms of said R₆ group.

17. The compound of claim 13 wherein said R₆ is any of the radicals from the group consisting of:

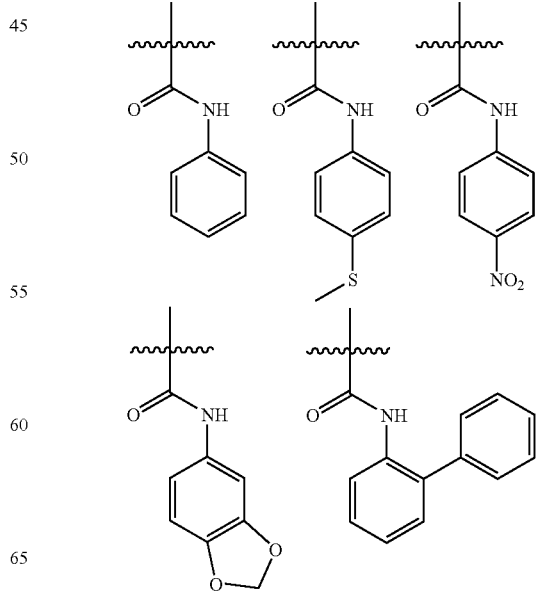

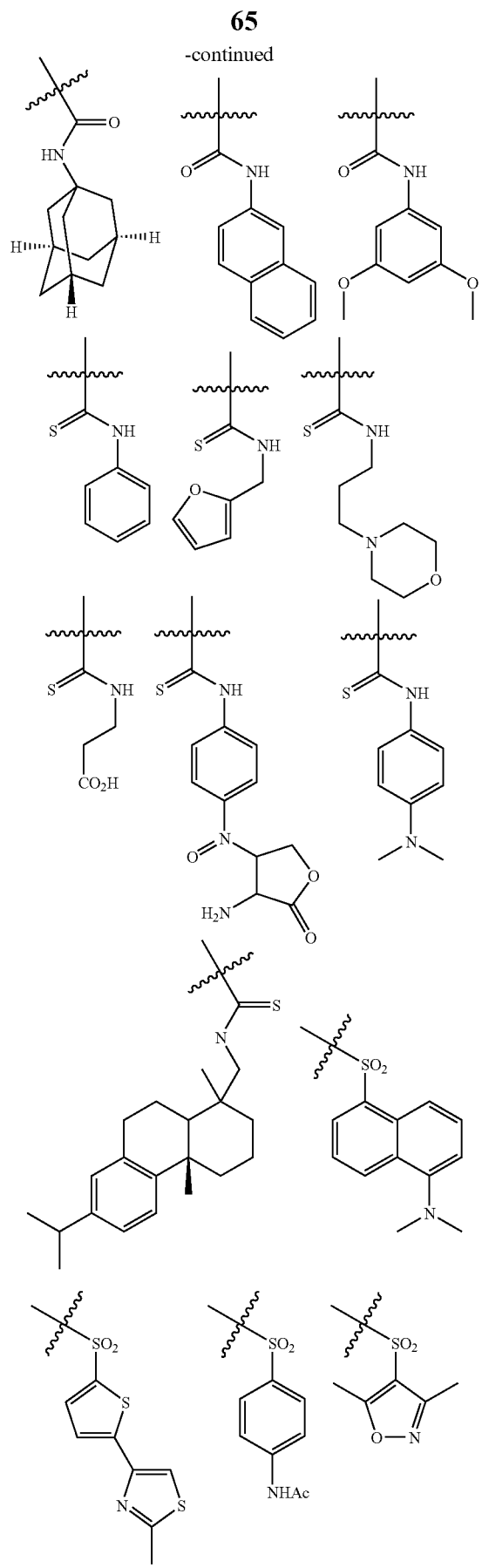
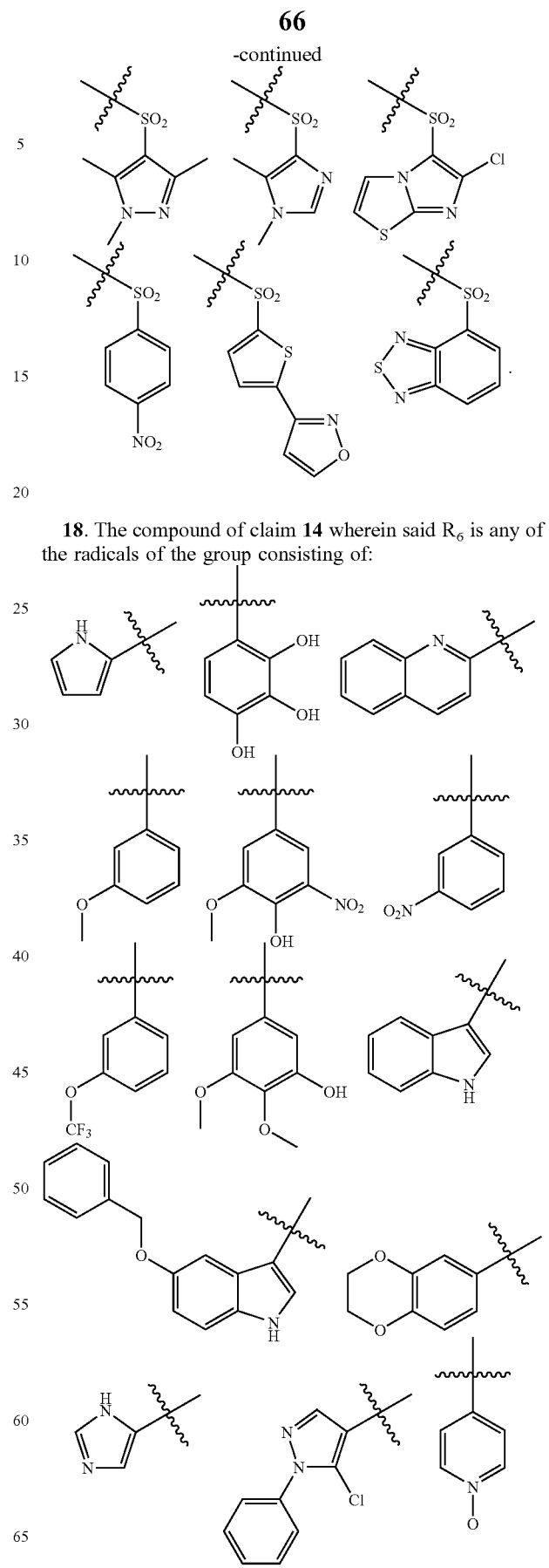
18. The compound of claim 14 wherein said $R_6$ is any of the radicals of the group consisting of:

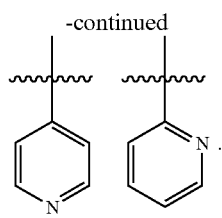

19. The compound of claim 5 wherein $R_1$ has the formula $-(CH_2)_q-L_4$ where q is 0 to 6 and $L_4$ is aryl, heteroaryl or heterocycloalkyl, arylsulfonamino, arylcarboxyamino or —S-heteroaryl, where each of said $L_4$ is optionally substituted with up to three substituents selected from halogen and $NO_2$.

20. The compound of claim 19 wherein said $L_4$ is N-maleimidyl, Nsuccinimidyl, N-phthalimidyl, N-naphthalimidyl, N-pyromellitic diimidyl, phenylsulfonamidyl, phenylcarboxamidyl, N-benzopyrrolidinyl, benzimidazol-1-yl; benzimidazol-2-yl, 1,2,4-triazolyl-4-yl, or purinyl, each of said $L_4$ groups being optionally substituted with 1 or 2 substituents selected from halogen, trihaloalkyl, trihaloalkoxy and $NO_2$.

21. A compound of formula:

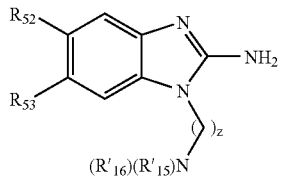

wherein:

$R_{52}$ and $R_{53}$ are each independently selected from H, halogen, $C_1$–$C_6$ alkyl, trihaloalkyl, alkoxycarbonyl, alkoxy;

or $R'_{15}$ and $R'_{16}$ together with the nitrogen atom to which they are attached can form a succinimido or phthalimido group or a fused ring derivative thereof, wherein said succinimido or phthalimido group or fused ring derivative thereof can be optionally substituted by up to three substituents independently selected from $NO_2$ and halogen; and z is 1 to 6.

22. The compound of claim 21 wherein z is 2 or 3.

23. The compound of claim 22 wherein $R_{52}$ and $R_{53}$ are each independently H, $C_{1-6}$ alkyl, alkoxy optionally substituted with dialkylamino, or alkylamino.

24. The compound of claim 23 wherein $R_{52}$ is H.

25. The compound of claim 24 wherein $R_{53}$ is methyl, methoxy, alkoxy optionally substituted with dialkylamino, or alkylamino.

26. The compound of claim 24 wherein $R_{53}$ is $OCH_3$ or $O(CH_2)_3N(CH_3)_2$.

27. The compound of claim 23 wherein $R_{53}$ is H.

28. The compound of claim 27 wherein $R_{52}$ is methyl, methoxy, alkoxy optionally substituted with dialkylamino, or alkylamino.

29. The compound of claim 27 wherein $R_{52}$ is $OCH_3$ or $O(CH_2)_3N(CH_3)_2$.

* * * * *

UNITED STATES PATENT AND TRADEMARK OFFICE
CERTIFICATE OF CORRECTION

PATENT NO.          : 7,244,847 B2                                   Page 1 of 9
APPLICATION NO. : 10/071978
DATED                 : July 17, 2007
INVENTOR(S)        : Eric E. Swayze et al.

It is certified that error appears in the above-identified patent and that said Letters Patent is hereby corrected as shown below:

1) Title Page:
Item [54], and Column 1, line 1 Title, please insert --Novel-- before "Benzimidazole";

2) Item [56], References Cited, OTHER PUBLICATIONS, "Freter" reference, please delete "n-(4-idolylpiperidinoalkyl)" and insert therefor --n-(4-indolylpiperidinoalkyl)--;

3) "Fonquerna" reference, please delete "Capluse" and insert therefor --Caplus--;

4) "Agai" reference, please delete "1,3,5,-triazepines, III" and insert therefor --1,3,5,-triazepines. III.--;

5) Column 61, Claim 1, lines 14-18, please delete " 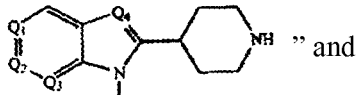 " and insert therefor -- 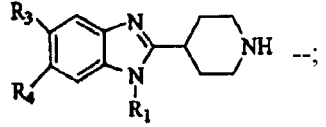 --;

6) Column 61, Claim 1, line 22, please insert --alkyl,-- between "is" and "aryl,";

7) Column 61, Claim 1, line 25, please delete "-$R_9$-X-$R_{10}$-$R_{11}$)H;" and insert therefor -- -$R_9$-X-$R_{10}$-($R_{11}$)H;--;

8) Column 61, Claim 1, line 32, please delete ";" and insert therefor --,--;

9) Column 61, Claim 1, line 49, please delete "heteroaryl," and insert therefor --heteroaryl or--;

10) Column 61, Claim 1, line 50, please delete "hereteroaryl" and insert therefor --heteroaryl--;

11) Column 61, Claim 1, line 52, please delete "," and insert therefor --;--;

12) Column 61, Claim 1, line 54, please delete ";" and insert therefor --,--;

13) Column 61, Claim 1, line 58, please delete "," after "-C(=O)-NH-heteroarylcarbonyl";

UNITED STATES PATENT AND TRADEMARK OFFICE
CERTIFICATE OF CORRECTION

PATENT NO. : 7,244,847 B2
APPLICATION NO. : 10/071978
DATED : July 17, 2007
INVENTOR(S) : Eric E. Swayze et al.

It is certified that error appears in the above-identified patent and that said Letters Patent is hereby corrected as shown below:

14) Column 61, Claim 1, line 61, please delete "," after "cycloalkylaminocarbonyl";

15) Column 62, Claim 1, line 3, please delete "," after "alkylheteroaryl";

16) Column 62, Claim 1, line 12, please delete "," after both "heteroaryl";

17) Column 62, Claim 1, line 26, please delete "," after "arylcarbonyl";

18) Column 62, Claim 1, line 26, please delete the second "and" and insert therefor --or--;

19) Column 62, Claim 1, lines 36-37, please delete ", or a group of Formula I at position $R_1$ thereof";

20) Column 62, Claim 1, line 39, please delete "group" and insert therefor --radical of a compound--;

21) Column 62, Claim 1, line 40, please delete "nitrogen atom is Q4" and insert therefor --radical is $R^1$--;

22) Column 63, Claim 10, lines 39-43, please delete

" 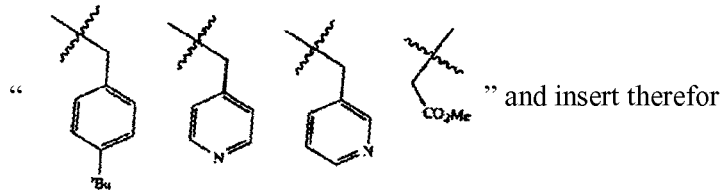 " and insert therefor

-- 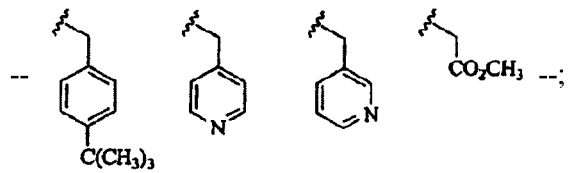 --;

UNITED STATES PATENT AND TRADEMARK OFFICE
CERTIFICATE OF CORRECTION

PATENT NO. : 7,244,847 B2
APPLICATION NO. : 10/071978
DATED : July 17, 2007
INVENTOR(S) : Eric E. Swayze et al.

It is certified that error appears in the above-identified patent and that said Letters Patent is hereby corrected as shown below:

23) Column 63, Claim 10, lines 58-66, please delete " 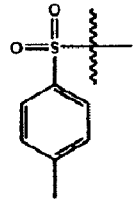 " and insert therefor -- 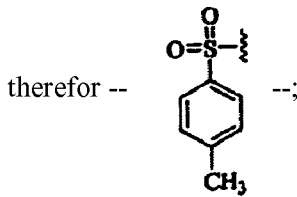 --;

24) Column 64, Claim 10, lines 1-11, please delete " 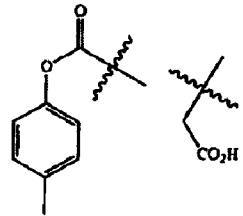 " and insert therefor -- 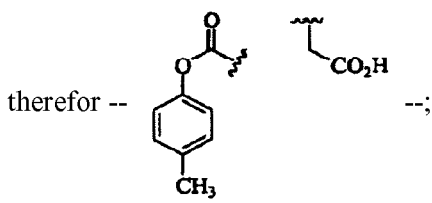 --;

25) Column 64, Claim 12, line 15, please delete ",";

26) Column 64, Claim 15, line 24, please delete ",";

27) Column 64, Claim 16, line 36, please delete "selected from" and insert therefor --substituted with--;

28) Column 64, Claim 17, lines 45-55, please delete " 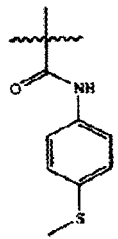 " and insert therefor -- 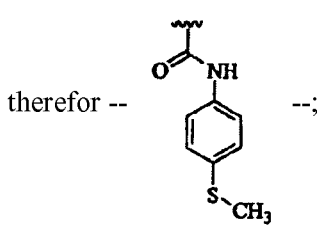 --;

UNITED STATES PATENT AND TRADEMARK OFFICE
CERTIFICATE OF CORRECTION

PATENT NO. : 7,244,847 B2
APPLICATION NO. : 10/071978
DATED : July 17, 2007
INVENTOR(S) : Eric E. Swayze et al.

It is certified that error appears in the above-identified patent and that said Letters Patent is hereby corrected as shown below:

29) Column 65, Claim 17, lines 1-13, please delete

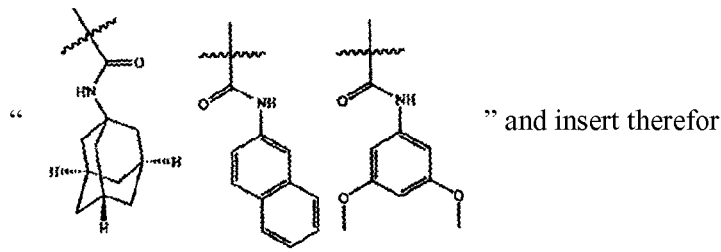 " and insert therefor

-- 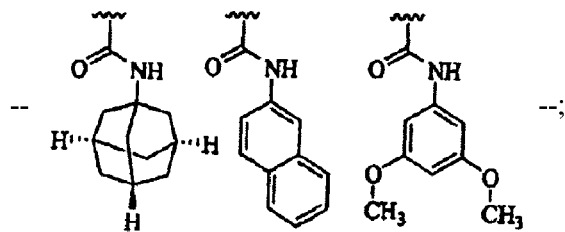 --;

UNITED STATES PATENT AND TRADEMARK OFFICE
CERTIFICATE OF CORRECTION

PATENT NO.         : 7,244,847 B2
APPLICATION NO. : 10/071978
DATED                  : July 17, 2007
INVENTOR(S)         : Eric E. Swayze et al.

It is certified that error appears in the above-identified patent and that said Letters Patent is hereby corrected as shown below:

30) Column 65, Claim 17, lines 25-26, please delete

"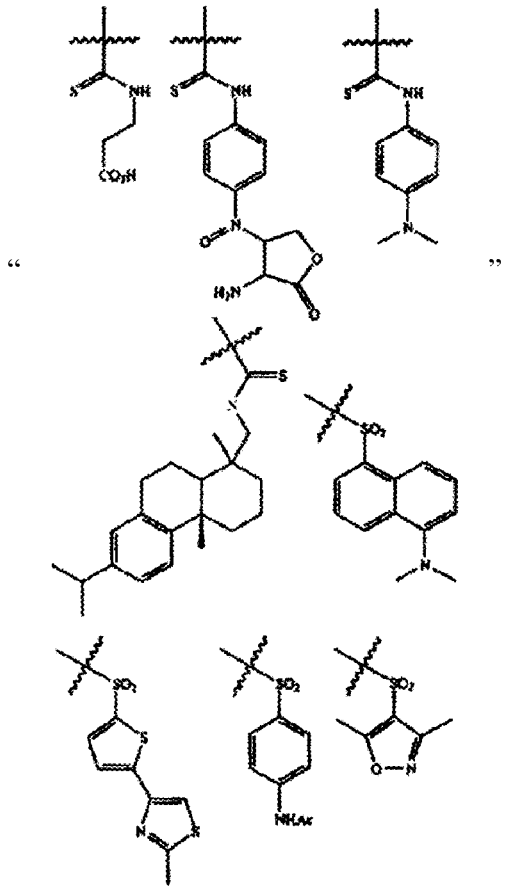"

UNITED STATES PATENT AND TRADEMARK OFFICE
CERTIFICATE OF CORRECTION

PATENT NO.       : 7,244,847 B2
APPLICATION NO.  : 10/071978
DATED            : July 17, 2007
INVENTOR(S)      : Eric E. Swayze et al.

Page 6 of 9

It is certified that error appears in the above-identified patent and that said Letters Patent is hereby corrected as shown below:

and insert therefor

-- 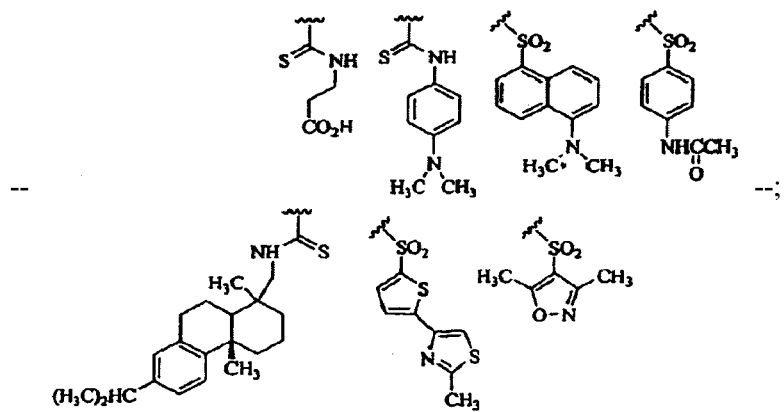 --;

31) Column 66, Claim 17, lines 1-19, please delete

" 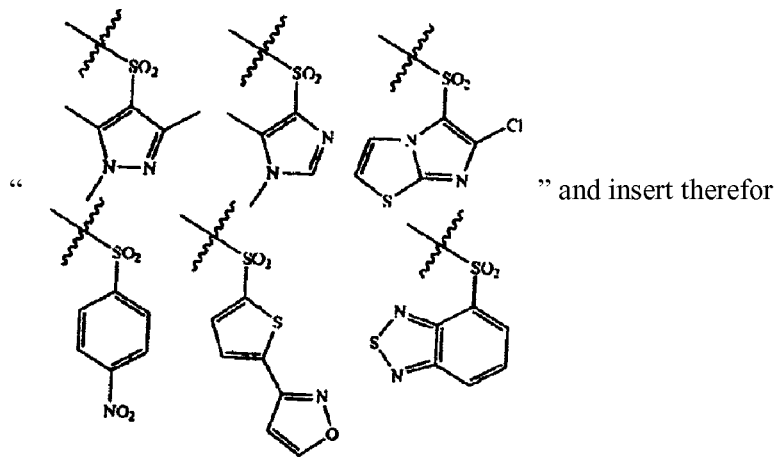 " and insert therefor

-- 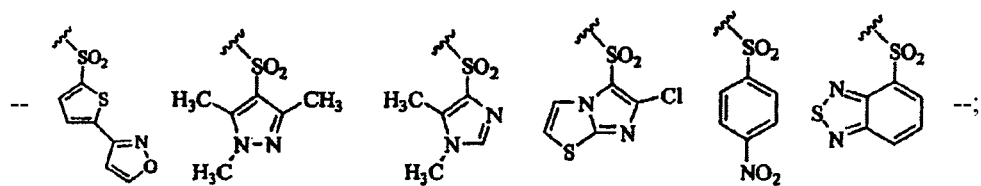 --;

UNITED STATES PATENT AND TRADEMARK OFFICE
CERTIFICATE OF CORRECTION

PATENT NO. : 7,244,847 B2
APPLICATION NO. : 10/071978
DATED : July 17, 2007
INVENTOR(S) : Eric E. Swayze et al.

It is certified that error appears in the above-identified patent and that said Letters Patent is hereby corrected as shown below:

32) Column 66, Claim 18, lines 32-47, please delete

"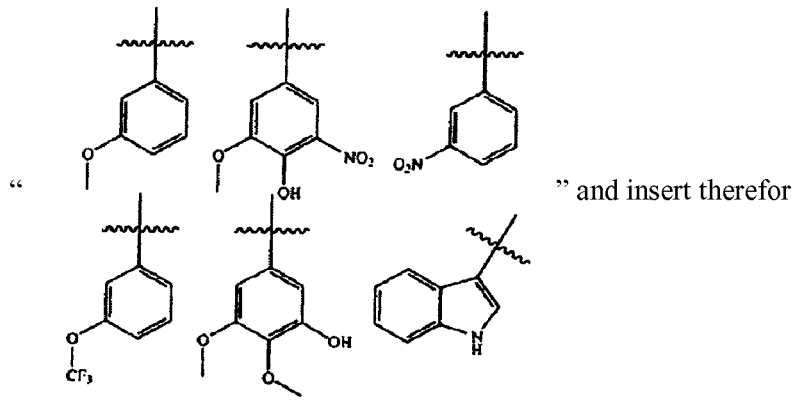" and insert therefor

--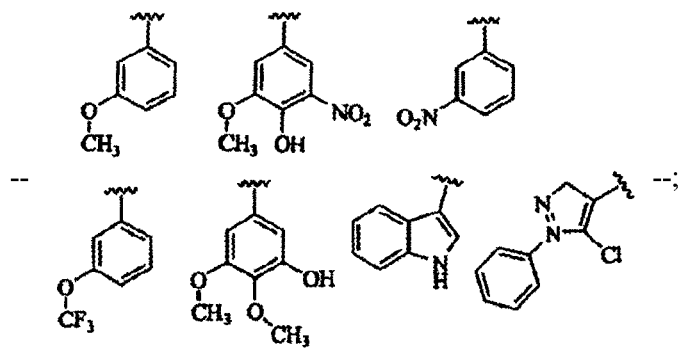--;

UNITED STATES PATENT AND TRADEMARK OFFICE
CERTIFICATE OF CORRECTION

PATENT NO. : 7,244,847 B2  
APPLICATION NO. : 10/071978  
DATED : July 17, 2007  
INVENTOR(S) : Eric E. Swayze et al.

It is certified that error appears in the above-identified patent and that said Letters Patent is hereby corrected as shown below:

33) Column 66, Claim 18, lines 57-66, please delete

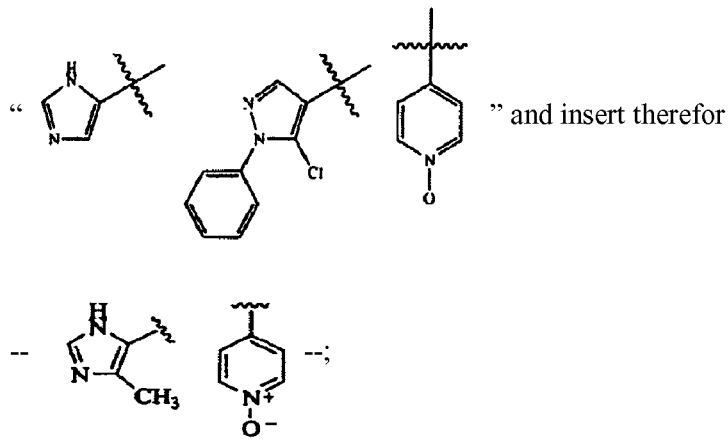

" and insert therefor

34) Column 67, Claim 20, line 17, please delete "Nsuccinimidyl" and insert therefor --N-succinimidyl--;

35) Column 67, Claim 20, line 20, please delete ";" and insert therefor --,--;

36) Column 67, Claim 21, lines 24-30, please delete " 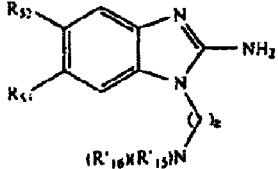 "

and insert therefor -- 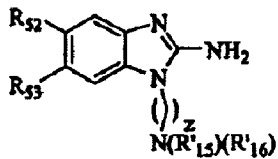 --;

UNITED STATES PATENT AND TRADEMARK OFFICE
CERTIFICATE OF CORRECTION

PATENT NO. : 7,244,847 B2
APPLICATION NO. : 10/071978
DATED : July 17, 2007
INVENTOR(S) : Eric E. Swayze et al.

It is certified that error appears in the above-identified patent and that said Letters Patent is hereby corrected as shown below:

37) Column 68, Claim 21, lines 7-8, please delete "can form a succinimido or phthalimido" and insert therefor --form a N-succinimidyl, N-phthalimidyl, N-maleimidyl, N-napthalimidyl, N-pyromellitic diimidyl, N-benzopyrrolidinyl or N-benzimidazol-l-yl--;

38) Column 68, Claim 21, line 8, please delete "or a fused ring derivative thereof,";

39) Column 68, Claim 21, lines 9-10, please delete "succinimido or phthalimido" and "or fused ring derivative thereof".

Signed and Sealed this

Twenty-first Day of October, 2008

JON W. DUDAS
*Director of the United States Patent and Trademark Office*

UNITED STATES PATENT AND TRADEMARK OFFICE
CERTIFICATE OF CORRECTION

PATENT NO.        : 7,244,847 B2                                             Page 1 of 1
APPLICATION NO. : 10/071978
DATED             : July 17, 2007
INVENTOR(S)       : Eric E. Swayze et al.

It is certified that error appears in the above-identified patent and that said Letters Patent is hereby corrected as shown below:

1) Column 1, line 10 insert the following:

--This invention was made with United States Government support under USAMRAA contract DAMD17-02-2-0023. The United States Government has certain rights in the invention.--

Signed and Sealed this

Tenth Day of November, 2009

David J. Kappos
*Director of the United States Patent and Trademark Office*